(12) United States Patent
Masuda et al.

(10) Patent No.: US 7,598,244 B2
(45) Date of Patent: Oct. 6, 2009

(54) [1,2,4]TRIAZOLO[1,5,A]PYRIMIDIN-2-YLUREA DERIVATIVE AND USE THEREOF

(75) Inventors: Akira Masuda, Saitama (JP); Yoshitaka Satoh, Yoshikawa (JP); Yuji Akiyama, Saitama (JP); Kan Saiga, Tokyo (JP); Eriko Toyoda, Kawasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 247 days.

(21) Appl. No.: 10/559,198

(22) PCT Filed: Jun. 2, 2004

(86) PCT No.: PCT/JP2004/007623

§ 371 (c)(1),
(2), (4) Date: Jan. 30, 2006

(87) PCT Pub. No.: WO2004/108729

PCT Pub. Date: Dec. 16, 2004

(65) Prior Publication Data

US 2007/0010515 A1    Jan. 11, 2007

(30) Foreign Application Priority Data

Jun. 3, 2003 (JP) ............................. 2003-157663

(51) Int. Cl.
| A61K 31/535 | (2006.01) |
| A61K 31/497 | (2006.01) |
| A01N 43/90 | (2006.01) |
| A61K 31/519 | (2006.01) |
| C07D 413/00 | (2006.01) |
| C07D 487/00 | (2006.01) |

(52) U.S. Cl. ............... 514/234.5; 514/252.16; 514/259.31; 544/114; 544/262

(58) Field of Classification Search .......... None
See application file for complete search history.

(56) References Cited

U.S. PATENT DOCUMENTS 5,484,760 A    1/1996    Bussler et al.

6,737,085 B2 *   5/2004  Nishibe et al. ............. 424/725

FOREIGN PATENT DOCUMENTS

| JP | 62-108882 | 5/1987 |
| WO | 92/10098 | 6/1992 |
| WO | 01/30778 | 5/2001 |
| WO | WO02/20495 | * 3/2002 |

OTHER PUBLICATIONS

Dorwald F. A. Side Reactions in Organic Synthesis, 2005, Wiley: VCH, Weinheim p. IX of Preface.*
The International Search Report dated Sep. 14, 2004.
Ludewig, B. et al., Current Opinion in Immunology, vol. 13, p. 657 (2001).
Thomas, R. et al., Journal of Leukocytes Biology, vol. 66, p. 286 (1999).
Menekigaku Illustrated (5th edition), Roitt, I. et al., edited and translated by Fujio Tada, Nankodo Co., Ltd., (2000), pp. 128-131 and pp. 355-358.
Ralph, M. S. et al., Proceedings of the National Academy of Sciences of the United States of America, vol. 99, 351 (2002).
The European communication dated Oct. 23, 2007.

* cited by examiner

*Primary Examiner*—James O Wilson
*Assistant Examiner*—Jeffrey H Murray
(74) *Attorney, Agent, or Firm*—Nields, Lemack & Frame, LLC

(57) ABSTRACT

Novel [1,2,4]triazolo[1,5-a]pyrimidine derivative of the general formula (1): (1) its prodrug or a pharmaceutically acceptable salt thereof, which exhibits an antigen presentation inhibiting activity and is useful as a preventive and/or therapeutic agent for immunological rejection and/or graft versus host reaction in organ/bone marrow transplant, autoimmune disease, allergic disease and/or inflammatory disease and also useful as an anticancer drug or as an immunological tolerance inducer for transplanted organ/transplanted bone marrow.

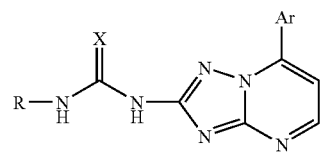

(1)

5 Claims, No Drawings

[1,2,4]TRIAZOLO[1,5,A]PYRIMIDIN-2-YLUREA DERIVATIVE AND USE THEREOF

TECHNICAL FIELD

The present invention relates to a [1,2,4]triazolo[1,5-a]pyrimidin-2-ylurea derivative or a pharmacologically acceptable salt thereof, and an immunosuppressive agent or an immune tolerance inducer using the above derivative or a salt thereof. Such an immunosuppressive agent can be used to treat or prevent autoimmune diseases, allergic diseases, diseases associated with tissue inflammation, rejection and graft versus host reaction in organ or bone marrow transplantation, and other diseases. Such an immune tolerance inducer can be used for engraftment of transplanted organ or bone marrow to a patient who undergoes organ or bone marrow transplantation. In addition, it can also be used as an anticancer drug.

BACKGROUND ART

Currently, immunosuppressive agents such as steroids, cyclosporin A, tacrolimus, mycophenolate mofetil, mizoribine, or deoxyspergualin have been used to treat or prevent graft rejection reaction, autoimmune diseases, allergic diseases, and various types of autoimmune diseases.

In recent years, it has been known that when a steroid drug that has been used as an anti-inflammatory agent for a long time is administered in a large amount, it acts on macrophages and lymphocytes to exhibit immunosuppressive activity.

Cyclosporin A and tacrolimus suppress production of cytokines acting as a lymphocytes controlling factor to exhibit immunosuppressive activity.

Cyclosporin A is administered to suppress rejection occurring after kidney, liver, bone marrow, or cardiac transplantation, or to treat Behcet's disease, psoriasis, aplastic anemia, and nephrotic syndrome.

Tacrolimus is used as a more potent cytokine production-suppressive agent, and is administered to suppress rejection occurring after kidney, liver, bone marrow, or cardiac transplantation, or to treat atopic dermatitis and myasthenia gravis.

Mycophenolate mofetil and mizoribine exhibit immunosuppressive activity as a result of a nucleic acid antimetabolite-effect on lymphocytes.

Mycophenolate mofetil is used to suppress rejection occurring after kidney transplantation. Mizoribine is used to suppress rejection occurring after kidney transplantation and to treat nephrotic syndrome, lupus nephritis, and chronic rheumatoid arthritis.

Deoxyspergualin inhibits production of antibodies and the functions of lymphocytes to exhibit immunosuppressive activity. It is used to treat rejection occurring after kidney transplantation.

Such an immunosuppressive agent is also useful for autoimmune diseases other than the aforementioned diseases. Cyclosporin A, for example, has been reported useful for diseases such as atopic dermatitis, autoimmune hepatitis, Crohn's disease, ulcerative colitis, myasthenia gravis, multiple sclerosis, rheumatoid arthritis, and insulin dependent diabetes mellitus, in addition to the aforementioned diseases.

By the way, in the aforementioned diseases, an immune phenomenon that has a harmful effect on a patient him/herself takes place via antigen presentation, causing pathological conditions. In the case of autoimmune disease, for example, an autoantigen or a foreign antigen similar to the autoantigen is presented to an immunocompetent cell by a dendritic cell that is one of antigen-presenting cells. It is considered that an immune response to the autoantigen is thereby induced, and that disruption of autotissues takes place.

Also, in rheumatism that is an inflammatory disease, accumulation of dendritic cells acting as antigen-presenting cells is observed in the affected region of the joint of a patient, and thus it is considered that such antigen presentation is associated with the development and the deterioration of the disease.

When T cells recognize cells expressing a target antigen, such recognition is conducted via MHC (major histocompatibility (gene) complex). Thus, for autoimmune diseases and inflammatory disease also, it is considered that antigen presentation is associated with activation of T cells in affected regions and tissue injury. Based on these facts, autoimmune diseases and the like can be treated or prevented by inhibiting the presentation of an autoantigen or a foreign antigen similar to the autoantigen.

Moreover, it has been reported that immune tolerance is induced by the difference in maturation stages of dendritic cells presenting antigens. Mature dendritic cells induce effector T lymphocytes having cytotoxicity and cytokine producing ability. In contrast, it is considered that immature dendritic cells induce regulatory or suppressive T cells, thereby playing an important role in inducing and maintaining immune tolerance. Accordingly, it is considered that if the maturation of cells presenting antigens (hereinafter referred to as antigen-presenting cells) is suppressed, immature dendritic cells increase, and that immune tolerance is thereby induced.

[Non-Patent Document 1] Ludewig, B. et al., Current Opinion in Immunology, vol. 13, p. 657 (2001)

[Non-Patent Document 2] Thomas, R. et al., Journal of Leukocytes Biology, vol. 66, p. 286 (1999)

[Non-Patent Document 3] *Menekigaku* Illustrated (5$^{th}$ edition), Roitt, I. et al., edited and translated by Fujio Tada, Nankodo Co., Ltd., (2000), pp. 128-131 and pp. 355-358

[Non-Patent Document 4] Ralph, M. S. et al., Proceedings of the National Academy of Sciences of the United States of America, vol. 99, 351 (2002)

DISCLOSURE OF THE INVENTION

As stated above, antigen presentation causing pathological conditions due to antigen-presenting cells is associated with autoimmune diseases, allergic diseases, tissue inflammatory diseases, rejection occurring after organ or bone marrow transplantation, and the like. Thus, it is considered that abnormal or excessive immune response can be suppressed by inhibiting the expression of antigen-presenting molecules or by modifying such antigen presentation by antigen-presenting cells. However, at present, such a compound has not yet been known.

It is considered that antigen presentation is a function specific to an immune system, and that a substance specifically inhibiting the aforementioned action to inhibit/modify antigen presentation does not exhibit action on systems other than the immune system, namely, the side effects of currently known immunosuppressive agents.

Moreover, it is considered that when the maturation of dendritic cells that present antigens is suppressed, immature dendritic cells increase and immune tolerance is thereby induced. However, such a compound has not yet been known.

It is an object of the present invention to provide an immunosuppressive agent or an immune tolerance inducer for suppressing harmful immune response with few side effects, by inhibiting/modifying antigen presentation.

As a result of intensive studies directed towards achieving the aforementioned object, the present inventors have found that a [1,2,4]triazolo[1,5-a]pyrimidin-2-ylurea derivative inhibits antigen presentation caused by antigen-presenting cells and has immunosuppressive activity. The inventors have also found that since the above compound suppresses lymphocyte proliferation response, it can be used as a therapeutic or preventive agent for immunological diseases, thereby completing the present invention.

Moreover, the inventors have also found that since the above compound suppresses the expression of antigen-presenting conjugated molecules associated with antigen presentation, it can be used as an immune tolerance inducer, thereby completing present invention. Furthermore, they have found that since the above compound has cytotoxic activity on cells of a lymphoma cell line, it can be used as an anticancer drug, thereby completing the present invention.

That is to say, the present invention relates to:
1) A [1,2,4]triazolo[1,5-a]pyrimidin-2-ylurea derivative represented by the following general formula (1), or a pharmacologically acceptable salt thereof:

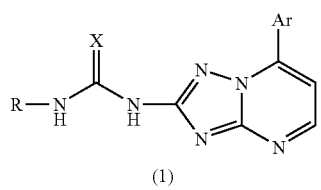

[Formula 1]

(1)

[wherein Ar represents an aromatic hydrocarbon group or an aromatic heterocyclic group containing 1 to 4 heteroatoms, which may have a substituent; X represents O, S, NH, N—CH₃, or N—CN; and R represents a hydrogen atom, a cyano group, a linear, branched, or cyclic alkyl group, which may have a substituent, an aromatic hydrocarbon group, which may have a substituent, or a 5- to 7-membered heterocyclic group containing 1 to 4 heteroatoms independently selected from among N, O, and S, which may have a substituent].

2) The [1,2,4]triazolo[1,5-a]pyrimidin-2-ylurea derivative according to 1) above, or a pharmacologically acceptable salt thereof, wherein a substituent for Ar in the general formula (1) is 1 to 4 identical or different groups selected from substituent group [B] consisting of: a halogeno group; a hydroxyl group; an oxo group; a cyano group; a trifluoromethyl group; a nitro group; a (C1-C6) alkyl group; an alkoxy group represented by the formula O—R1 {wherein, R1 represents a (C1-C6) alkyl group, which may be substituted with 1 to 4 identical or different groups selected from substituent group [A] consisting of a halogeno group, a hydroxyl group, an oxo group, a cyano group, a trifluoromethyl group, a trifluoromethoxy group, a (C1-C6) alkoxyl group, a (C1-C4) alkoxy (C1-C4) alkoxyl group, a 2-[2-(C1-C4) alkoxyethoxy]ethoxy group, a 2-{2-[2-(C1-C4) alkoxyethoxy]ethoxy}ethoxy group, a (C1-C7) acyl group, a (C1-C7) acyloxy group, a (C1-C6) akylsulfanyl group, a (C1-C6) alkylsulfinyl group, a (C1-C6) alkylsulfonyl group, a carboxyl group, a (C1-C6) alkoxycarbonyl group, a carbamoyl group, an N-(C1-C6) alkylcarbamoyl group, an N,N-di(C1-C6) alkylcarbamoyl group, a pyrrolidin-1-ylcarbonyl group, a piperidin-1-yl carbonyl group, a morpholin-4-ylcarbonyl group, a 4-methylpiperazin-1-ylcarbonyl group, an amino group represented by the formula NR2R3 (wherein each of R2 and R3 independently represents a hydrogen atom, a (C1-C6) alkyl group, a (C1-C7) acyl group, a (C1-C6) alkoxycarbonyl group, or a benzyloxycarbonyl group), an aromatic hydrocarbon group, and a 5- to 7-membered saturated or unsaturated heterocyclic ring wherein an oxo group or a (C1-C6) alkyl group may be substituted and which contains 1 to 4 heteroatoms independently selected from among N, O, and S; an amino group represented by the formula NR2R3 {wherein R2 and R3 have the same meanings as described above}; a 5- to 7-membered saturated cyclic amino group, which may be substituted with a (C1-C6) alkyl group, and which may contain 1 to 4 heteroatoms independently selected from among N, O, and S; an ethyleneoxy group; and a (C1-C2) alkylenedioxy group; and wherein the linear, branched, or cyclic alkyl group, which may have a substituent, the aromatic hydrocarbon group, which may have a substituent, or the 5- to 7-membered heterocyclic group containing 1 to 4 heteroatoms independently selected from among N, O, and S, which may have a substituent, the group being represented by R, is a group represented by any one of the following formulas (2) to (6):

[Formula 2]

(2)

[wherein R4 represents a hydrogen atom, a (C1-C6) alkyl group, a (C2-C10) alkenyl group, a (C2-C10) alkynyl group, a (C1-C4) alkoxymethyl group, a cyano group, or a trifluoromethyl group;

R5 represents a hydrogen atom or a methyl group; and

R6 represents a hydrogen atom, a (C1-C10) alkyl group {wherein the above alkyl group may be substituted with 1 to 4 identical or different substituents selected from substituent group [C] consisting of a halogeno group, a hydroxyl group, an oxo group, a (C1-C6) alkoxyl group, a (C1-C4) alkoxy (C1-C4) alkoxyl group, a halogeno (C1-C3) alkyl group, a (C1-C7) acyl group, a (C1-C7) acyloxy group, a trifluoromethyl group, a cyano group, a (C1-C6) alkylsulfanyl group, a phenylsulfanyl group, a toluene-4-sulfanyl group, a (C1-C6) alkylsulfinyl group, a phenylsulfinyl group, a toluene-4-sulfinyl group, a (C1-C6) alkylsulfonyl group, a phenylsulfonyl group, a toluene-4-sulfonyl group, a carboxyl group, a (C1-C6) alkoxycarbonyl group, a carbamoyl group, an N-(C1-C6) alkylcarbamoyl group, an N,N-di(C1-C6) alkylcarbamoyl group, a pyrrolidin-1-ylcarbonylgroup, a piperidin-1-yl carbonyl group, a morpholin-4-ylcarbonyl group, a 4-methylpiperazin-1-ylcarbonyl group, an amino group represented by the formula NR13R14 (wherein each of R13 and R14 independently represents a hydrogen atom, a (C1-C6) alkyl group, a (C1-C7) acyl group, an acetoxyisobutyryl group, a (C1-C6) alkoxycarbonyl group, or a benzyloxycarbonyl group), an aromatic hydrocarbon group, and a 5- to 7-membered saturated or unsaturated heterocyclic group containing 1 to 4 heteroatoms independently selected from among N, O, and S, which may be substituted with an oxo group or a (C1-C6) alkyl group}, a (C2-C10) alkenyl group (wherein the above alkenyl group may have 1 to 4 substituents selected from the above described substituent group [C]), a (C2-C10) alkynyl group (wherein the above alkynyl group may have 1 to 4 substituents selected from the above described substituent group [C]), or a 5- to 7-membered heterocyclic group containing 1 to 4 heteroatoms independently selected from among N, O, and S],

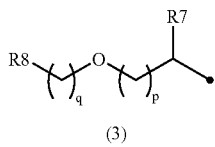

[Formula 3]

(3)

[wherein R7 represents a hydrogen atom, a (C1-C6) alkyl group, a (C1-C4) alkoxymethyl group, a cyano group, or a trifluoromethyl group;
R8 represents a 5- to 7-membered saturated or unsaturated heterocyclic group containing 1 to 4 heteroatoms independently selected from among N, O, and
S, which may be substituted with an oxo group or a (C1-C6) alkyl group;
p represents an integer between 1 and 3; and
q represents an integer between 0 and 3],

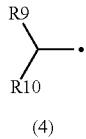

[Formula 4]

(4)

[wherein R9 represents a hydrogen atom, a (C1-C6) alkyl group, a (C2-C10) alkenyl group, a (C2-C10) alkynyl group, a (C1-C4) alkoxymethyl group, a cyano group, or a trifluoromethyl group; and
R10 represents an aromatic hydrocarbon group, which may have 1 to 4 substituents selected from substituent group [D] consisting of a halogeno group, hydroxyl group, (C1-C6) alkyl group, (C1-C6) alkoxyl group, (C1-C4) alkoxy (C1-C4) alkoxyl group, (C1-C4) alkoxy (C1-C4) alkoxy (C1-C4) alkoxyl group, tetrahydrofuran-2-ylmethoxy group, tetrahydropyran-4-ylmethoxy group, benzyloxy group, methylenedioxy group, (C1-C7) acyl group, trifluoromethyl group, trifluoromethoxy group, cyano group, nitro group, (C1-C6) alkylsulfanyl group, (C1-C6) alkylsulfinyl group, (C1-C6) alkylsulfonyl group, (C1-C6) alkylsulfonyloxy group, (C1-C6) alkoxycarbonyloxy group, benzyloxycarbonyloxy group, (C1-C6) alkoxycarbonylmethoxy group, carboxyl group, (C1-C6) alkoxycarbonyl group, carbamoyl group, N-(C1-C6) alkylcarbamoyl group, N,N-di(C1-C6) alkylcarbamoyl group, pyrrolidin-1-ylcarbonyl group, piperidin-1-ylcarbonyl group, morpholin-4-ylcarbonyl group, 4-methylpiperazin-1-ylcarbonyl group, pyridin-2-ylmethoxy group, pyridin-3-ylmethoxy group, pyridin-4-ylmethoxy group, and an amino group represented by the formula NR2R3 (wherein R2 and R3 have the same meanings as described above)],

[Formula 5]

(5)

[wherein Cy represents a phenyl group, a (C3-C10) cycloalkyl group, a 1,2,3,4-tetrahydronaphthalen-1-yl group, or a 5- to 7-membered heterocyclic group containing 1 to 4 heteroatoms independently selected from among N, O, and S, which may be substituted with 1 to 4 identical or different groups selected from substituent group [E] consisting of a halogeno group, a hydroxyl group, a carboxyl group, a (C1-C6) alkyl group, a phenyl group, a benzyl group, a (C1-C6) alkoxyl group, a (C1-C7) acyl group, a (C1-C7) acyloxy group, a trifluoromethyl group, a trifluoromethoxy group, a cyano group, a (C1-C6) alkoxycarbonyl group, a carbamoyl group, an N—(C1-C6) alkylcarbamoyl group, an N,N-di(C1-C6) alkylcarbamoyl group, a pyrrolidin-1-ylcarbonyl group, a piperidin-1-yl carbonyl group, a morpholin-4-ylcarbonyl group, a 4-methylpiperazin-1-ylcarbonyl group, and an amino group represented by the formula NR2R3 (wherein R2 and R3 have the same meanings as described above)], and

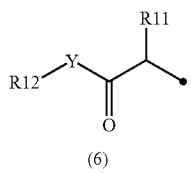

[Formula 6]

(6)

[wherein Y represents a single bond, or an α-amino acid residue, the side chain of which may be protected;
R11 represents an amino acid side chain, which may be protected by a protecting group; and
R12 represents a hydroxyl group, a (C1-C6) alkoxyl group, a benzyloxy group, an amino group, a hydroxylamino group, a (C1-C6) alkylamino group, which may be substituted with 1 to 2 identical or different substituents selected from the above described substituent group [C], a di(C1-C6) alkylamino group, which may be substituted with 1 to 2 identical or different substituents selected from the above described substituent group [C], a cyclohexylmethylamino group, a phenylamino group, which may be substituted with 1 to 2 identical or different substituents selected from the above described substituent group [C], or a 5- to 7-membered saturated or unsaturated heterocyclic group containing 1 to 4 heteroatoms independently selected from among N, O, and S, which may be substituted with 1 to 4 identical or different groups selected from substituent group [F] consisting of an oxo group, a (C1-C6) alkyl group, a phenyl group, and a benzyl group].

3) The [1,2,4]triazolo[1,5-a]pyrimidin-2-ylurea derivative according to 2) above, or a pharmaceutically acceptable salt thereof, wherein, in the above described general formula (1), Ar represents a phenyl group, which may have 1 to 4 identical or different substituents selected from substituent group [G] consisting of a fluoro group, chloro group, hydroxyl group, methyl group, cyano group, trifluoromethyl group, methoxy group, ethoxy group, isopropoxy group, cyclopropoxy group, isobutoxy group, benzyloxy group, 2-methoxyethoxy group, 2-(2-methoxyethoxy)ethoxy group, 2-[2-(2-methoxyethoxy)ethoxy]ethoxy group, tetrahydrofuran-2-ylmethoxy group, tetrahydropyran-4-ylmethoxy group, 2-[1,3]dioxan-2-ylethoxy group, 2-dimethylaminoethoxy group, 3-dimethylaminopropyl group, 2-diethylaminoethoxy group, 3-diethylaminopropyl group, 2-morpholin-4-yl-2-oxoethoxy group, 2-piperidin-1-ylethoxy group, 3-piperidin-1-ylpropoxy group, 2-morpholin-4-ylethoxy group, 3-morpholin-4-ylpropoxy group, 2-(1-methylpiperidin-4-yl)ethoxy group, 3-(1-methylpiperidin-4-yl)propoxy group, pyridin-2-ylmethoxy group, pyridin-3-ylmethoxy group, pyridin-4-ylmethoxy group, amino group, dimethylamino group, diethylamino group, acetylamino group, pyrrolidin-1-yl group, piperidin-1-yl group, 4-methylpiperazin-1-yl group, morpholin-4-yl group, and methylenedioxy group, a 2,3-dihydrobenzofuran-5-yl group, a pyridin-3-yl group, a pyridin-4-yl group, a 1-oxypyridin-3-yl group, a 1-oxypyridin-4-yl group, a thiophen-2-yl group, or a thiophen-3-yl group;

X represents O or S; and with regard to R, in the formula (2), R4 represents a hydrogen atom, a methyl group, an ethyl group, an isopropyl group, a methoxymethyl group, or a trifluoromethyl group, R5 represents a hydrogen atom, and R6 represents a (C1-C6) alkyl group, which may have 1 to 2 identical or different substituents selected from substituent group [H] consisting of a fluoro group, a trifluoromethyl group, a hydroxyl group, a methoxy group, an ethoxy group, a propoxy group, an isopropoxy group, an isobutoxy group, a tert-butoxy group, a 2-methoxyethoxy group, a fluoromethoxy group, a difluoromethoxy group, a trifluoromethoxy group, a 2,2,2-trifluoroethoxy group, a 1,1,2,2-tetrafluoroethoxy group, an acetyl group, a propionyl group, a cyano group, a methanesulfonyl group, an ethanesulfonyl group, an N,N-dimethylcarbamoyl group, a pyrrolidin-1-ylcarbonyl group, a piperidin-1-yl carbonyl group, a morpholin-4-ylcarbonyl group, a tetrahydrofuran-2-yl group, a tetrahydropyran-4-yl group, and a 2-methyl[1,3]dioxolan-2-yl group, in the formula (3), R7 represents a hydrogen atom, a methyl group, an ethyl group, an isopropyl group, a methoxymethyl group, or a trifluoromethyl group, R8 represents a tetrahydrofuran-2-yl group, a tetrahydropyran-4-yl group, or a 2-methyl[1,3]dioxolan-2-yl group, and the sum of p and q is an integer of 4 or less, or in the formula (4), R9 represents a hydrogen atom, a methyl group, an ethyl group, an isopropyl group, a methoxymethyl group, or a trifluoromethyl group, and R10 represents a phenyl group having 1 to 4 substituents selected from the group consisting of a hydroxyl group, a methoxy group, a trifluoromethoxy group, a methylenedioxy group, and a methanesulfonyloxy group.

4) The [1,2,4]triazolo[1,5-a]pyrimidin-2-ylurea derivative according to any one of 1) to 3) above, or a pharmaceutically acceptable salt thereof, wherein, in the above described general formula (1), Ar represents a 3-hydroxyphenyl group, a 3-methoxyphenyl group, a 4-hydroxyphenyl group, a 4-methoxyphenyl group, a 3,4-methylenedioxyphenyl group, a 3-(pyridin-3-ylmethoxy)phenyl group, a 4-(tetrahydropyran-4-ylmethoxy)phenyl group, or a thiophen-2-yl group;

X represents O; and

R represents an isopropyl group, 2-methoxy-1-methylethyl group, 2-ethoxy-1-methylethyl group, 2-propoxy-1-methylethyl group, 3-methoxy-1-methylpropyl group, 3-ethoxy-1-methylpropyl group, 4-methoxy-1-methylbutyl group, 1-methyl-2-trifluoromethoxyethyl group, 1-methyl-2-(2,2,2-trifluoroethoxy)ethyl group, 1-methyl-3-trifluoromethoxypropyl group, 4-hydroxy-1,4-dimethylpentyl group, 5-hydroxy-1,5-dimethylhexyl group, 5-methoxy-1,5-dimethylhexyl group, 1-methyl-3-(tetrahydropyran-4-yl)propyl group, 1-methyl-2-(tetrahydropyran-4-yloxy)ethyl group, 1-methyl-2-(tetrahydropyran-4-ylmethoxy)ethyl group, 1-methyl-3-(2-methyl[1,3]dioxolan-2-yl)propyl group, 1-methyl-4-oxopentyl group, 1-(3-hydroxyphenyl)ethyl group, 1-(3-methoxyphenyl)ethyl group, 1-(3,4-methylenedioxyphenyl)ethyl group, 1-(3,4,5-trimethoxyphenyl)ethyl group, or 1-(3-methanesulfonyloxyphenyl)ethyl group.

5) The [1,2,4]triazolo[1,5-a]pyrimidin-2-ylurea derivative according to 4) above, or a pharmaceutically acceptable salt thereof, wherein, R in the above described general formula (1) represents an isopropyl group, an (S)-2-methoxy-1-methylethyl group, an (S)-3-methoxy-1-methylpropyl group, an (S)-3-ethoxy-1-methylpropyl group, an (S)-4-methoxy-1-methylbutyl group, an (S)-4-hydroxy-1,4-dimethylpentyl group, an (S)-5-hydroxy-1,5-dimethylhexyl group, an (S)-1-(3-methoxyphenyl)ethyl group, an (S)-1-(3,4-methylenedioxyphenyl)ethyl group, or an (S)-1-(3,4,5-trimethoxyphenyl)ethyl group.

6) 1-isopropyl-3-(7-thiophen-2-yl[1,2,4]triazolo[1,5-a]pyrimidin-2-yl)urea;
(S)-1-(3-ethoxy-1-methylpropyl)-3-[7-(3,4-methylenedioxyphenyl)-[1,2,4]triazolo[1,5-a]pyrimidin-2-yl]urea;
(S)-1-(4-methoxy-1-methylbutyl)-3-[7-(4-methoxyphenyl)-[1,2,4]triazolo[1,5-a]pyrimidin-2-yl]urea;
(S)-1-(4-hydroxy-1,4-dimethylpentyl)-3-[7-(4-methoxyphenyl)-[1,2,4]triazolo[1,5-a]pyrimidin-2-yl]urea;
(S)-1-(5-hydroxy-1,5-dimethylhexyl)-3-[7-(4-methoxyphenyl)-[1,2,4]triazolo[1,5-a]pyrimidin-2-yl]urea;
(S)-1-(5-hydroxy-1,5-dimethylhexyl)-3-{7-[3-(pyridin-3-ylmethoxy)phenyl]-[1,2,4]triazolo[1,5-a]pyrimidin-2-yl}urea;
(S)-1-(5-hydroxy-1,5-dimethylhexyl)-3-[(7-thiophen-2-yl)-[1,2,4]triazolo[1,5-a]pyrimidin-2-yl]urea;
(S)-1-[1-(3-methoxyphenyl)ethyl]-3-[7-(4-methoxyphenyl)-[1,2,4]triazolo[1,5-a]pyrimidin-2-yl]urea;
(S)-1-[7-(3,4-methylenedioxyphenyl)-[1,2,4]triazolo[1,5-a]pyrimidin-2-yl]-3-[1-(3-methoxyphenyl)ethyl]urea;
(S)-1-[7-(3,4-methylenedioxyphenyl)-[1,2,4]triazolo[1,5-a]pyrimidin-2-yl]-3-[1-(3,4,5-trimethoxyphenyl)ethyl]urea;
(S)-1-(7-thiophen-2-yl[1,2,4]triazolo[1,5-a]pyrimidin-2-yl)-3-[1-(3,4,5-trimethoxyphenyl)ethyl]urea;
(S)-1-[1-(3,4-methylenedioxyphenyl)ethyl]-3-{7-[3-(pyridin-3-ylmethoxy)phenyl]-[1,2,4]triazolo[1,5-a]pyrimidin-2-yl}urea;, or a pharmaceutically acceptable salt thereof.

7) A pharmaceutical, which comprises, as an active ingredient, the [1,2,4]triazolo[1,5-a]pyrimidin-2-ylurea derivative according to any one of 1) to 6) above, or a pharmaceutically acceptable salt thereof.

8) An antigen presentation inhibitor, which comprises, as an active ingredient, the [1,2,4]triazolo[1,5-a]pyrimidin-2-ylurea derivative according to any one of 1) to 6) above, or a pharmaceutically acceptable salt thereof.

9) An immunosuppressive agent, which comprises, as an active ingredient, the [1,2,4]triazolo[1,5-a]pyrimidin-2-ylurea derivative according to any one of 1) to 6) above, or a pharmaceutically acceptable salt thereof.

10) A lymphocyte proliferation inhibitor, which comprises, as an active ingredient, the [1,2,4]triazolo[1,5-a]pyrimidin-2-ylurea derivative according to any one of 1) to 6) above, or a pharmaceutically acceptable salt thereof.

11) An inhibitor for cell growth/maturation, which comprises, as an active ingredient, the [1,2,4]triazolo[1,5-a]pyrimidin-2-ylurea derivative according to any one of 1) to 6) above, or a pharmaceutically acceptable salt thereof.

12) A therapeutic or preventive agent for graft rejection reaction or graft versus host reaction disease, which comprises, as an active ingredient, the [1,2,4]triazolo[1,5-a]pyrimidin-2-ylurea derivative according to any one of 1) to 6) above, or a pharmaceutically acceptable salt thereof.

13) An immune tolerance inducer, which comprises, as an active ingredient, the [1,2,4]triazolo[1,5-a]pyrimidin-2-ylurea derivative according to any one of 1) to 6) above, or a pharmaceutically acceptable salt thereof.

14) A therapeutic or preventive agent for autoimmune disease, which comprises, as an active ingredient, the [1,2,4]triazolo[1,5-a]pyrimidin-2-ylurea derivative according to any one of 1) to 6) above, or a pharmaceutically acceptable salt thereof.

15) A therapeutic or preventive agent for rheumatoid arthritis, multiple sclerosis, systemic lupus erythematosus, discoid lupus erythematosus, Sjogren's syndrome, Crohn's disease, ulcerative colitis, idiopathic thrombocythemia, aplastic anemia, autoimmune hepatitis, insulin dependent diabetes mellitus, myasthenia gravis, polymyositis, scleroderma, mixed connective tissue disease, ankylosing spondylitis, or chronic thyroiditis, which comprises, as an active ingredient, the [1,2,4]triazolo[1,5-a]pyrimidin-2-ylurea derivative according to any one of 1) to 6) above, or a pharmaceutically acceptable salt thereof.

16) A therapeutic or preventive agent for allergic disease, which comprises, as an active ingredient, the [1,2,4]triazolo[1,5-a]pyrimidin-2-ylurea derivative according to any one of 1) to 6) above, or a pharmaceutically acceptable salt thereof.

17) A therapeutic or preventive agent for atopic dermatitis, pollinosis, contact hypersensitivity, asthma, psoriasis, or anaphylaxis, which comprises, as an active ingredient, the [1,2,4]triazolo[1,5-a]pyrimidin-2-ylurea derivative according to any one of 1) to 6) above, or a pharmaceutically acceptable salt thereof.

18) A therapeutic or preventive agent for inflammatory disease, which comprises, as an active ingredient, the [1,2,4]triazolo[1,5-a]pyrimidin-2-ylurea derivative according to any one of 1) to 6) above, or a pharmaceutically acceptable salt thereof.

19) A therapeutic or preventive agent for Behcet's disease, polyarteritis, sarcoidosis, glomerulonephritis, nephrotic syndrome, refractory angiitis, or Wegener's syndrome, which comprises, as an active ingredient, the [1,2,4]triazolo[1,5-a]pyrimidin-2-ylurea derivative according to any one of 1) to 6) above, or a pharmaceutically acceptable salt thereof.

20) An anticancer drug, which comprises, as an active ingredient, the [1,2,4]triazolo[1,5-a]pyrimidin-2-ylurea derivative according to any one of 1) to 6) above, or a pharmaceutically acceptable salt thereof.

BEST MODE FOR CARRYING OUT THE INVENTION

The [1,2,4]triazolo[1,5-a]pyrimidin-2-ylurea derivative of the present invention is represented by the above general formula (1) [wherein Ar represents an aromatic hydrocarbon group or an aromatic heterocyclic group containing 1 to 4 heteroatoms, which may have a substituent; X represents O, S, NH, N—$CH_3$, or N—CN; and R represents a hydrogen atom, a cyano group, a linear, branched, or cyclic alkyl group, which may have a substituent, an aromatic hydrocarbon group, which may have a substituent, or a 5- to 7-membered heterocyclic group containing 1 to 4 heteroatoms independently selected from among N, O, and S, which may have a substituent].

The "aromatic hydrocarbon group" is not particularly limited in the present invention, and an aromatic heterocyclic ring containing an atom selected from among N, O, and S, may be condensed. A preferred example of such an aromatic hydrocarbon group may be a (C6-C14) aromatic hydrocarbon group. Specific examples may include a phenyl group, a naphthalen-1-yl group, and a naphthalen-2-yl group. Particularly preferred examples may include a phenyl group and a naphthalen-1-yl group. The most preferred example is a phenyl group.

The "aromatic heterocyclic group containing 1 to 4 heteroatoms" represented by Ar in the general formula (1) of the present invention is not particularly limited. Preferably, it is a 5- or 6-membered aromatic heterocyclic group independently selected from among N, O, and S. Specific examples may include a furan-2-yl group, a furan-3-yl group, a thiophen-2-yl group, a thiophen-3-yl group, an oxazol-5-yl group, an isoxazol-5-yl group, a thiazol-5-yl group, a pyridin-2-yl group, a pyridin-3-yl group, a pyridin-4-yl group, a pyridimin-4-yl group, a pyrazin-2-yl group, and a [1,3,5]triazin-2-yl group. Particularly preferred examples may include a furan-2-yl group, a furan-3-yl group, a thiophen-2-yl group, a thiophen-3-yl group, a pyridin-3-yl group, a pyridin-4-yl group, and a pyrimidin-4-yl group. Further preferred examples may include a thiophen-2-yl group, a pyridin-3-yl group, and a pyridin-4-yl group.

Examples of a substituent used in an aromatic hydrocarbon group or an aromatic heterocyclic group containing 1 to 4 heteroatoms, which may have a substituent, represented by Ar in the general formula (1) of the present invention, may include 1 to 4 identical or different groups selected from substituent group [B] consisting of: a halogeno group; a hydroxyl group; an oxo group; a cyano group; a trifluoromethyl group; a nitro group; a (C1-C6) alkyl group; an alkoxy group represented by the formula O—R1 {wherein, R1 represents a (C1-C6) alkyl group, which may be substituted with 1 to 4 identical or different groups selected from substituent group [A] consisting of a halogeno group, a hydroxyl group, an oxo group, a cyano group, a trifluoromethyl group, a trifluoromethoxy group, a (C1-C6) alkoxyl group, a (C1-C4) alkoxy (C1-C4) alkoxyl group, a 2-(2-(C1-C4) alkoxyethoxy)ethoxy group, a 2-(2-(2-(C1-C4) alkoxyethoxy)ethoxy)ethoxy group, a (C1-C7) acyl group, a (C1-C7) acyloxy group, a (C1-C6) akylsulfanyl group, a (C1-C6) alkylsulfinyl group, a (C1-C6) alkylsulfonyl group, a carboxyl group, a (C1-C6) alkoxycarbonyl group, a carbamoyl group, an N—(C1-C6) alkylcarbamoyl group, an N,N-di(C1-C6) alkylcarbamoyl group, a pyrrolidin-1-ylcarbonyl group, a piperidin-1-yl carbonyl group, a morpholin-4-ylcarbonyl group, a 4-methylpiperazin-1-ylcarbonyl group, an amino group represented by the formula NR2R3 (wherein each of R2 and R3 independently represents a hydrogen atom, a (C1-C6) alkyl group, a (C1-C7) acyl group, a (C1-C6) alkoxycarbonyl group, or a benzyloxycarbonyl group), an aromatic hydrocarbon group, and a 5- to 7-membered saturated or unsaturated heterocyclic ring containing 1 to 4 heteroatoms independently selected from among N, O, and S, wherein an oxo group or a (C1-C6) alkyl group may be substituted}; an amino group represented by the formula NR2R3 {wherein R2 and R3 have the same meanings as described above}; a 5- to 7-membered saturated cyclic amino group, which may be substituted with a (C1-C6) alkyl group, and which may contain 1 to 2 heteroatoms independently selected from among N, O, and S; an ethyleneoxy group; and a (C1-C2) alkylenedioxy group.

The "halogeno group" is used in the present invention to mean a fluoro group, a chloro group, a bromo group, or an iodo group. It is preferably a fluoro group or a chloro group.

The "oxo group" used in the present invention forms a carbonyl group, when it is substituted with a carbon atom. It forms an oxide form such as N-oxide or sulfoxide when it is substituted with a heteroatom.

The "(C1-C6) alkyl group" is used in the present invention to mean a linear, branched, or cyclic alkyl group containing 1 to 6 carbon atoms, unless otherwise specified. Examples of such a (C1-C6) alkyl group may include a methyl group, an ethyl group, an n-propyl group, an isopropyl group, an n-butyl group, an isobutyl group, a tert-butyl group, an n-pentyl group, an isopentyl group, a 2-methylbutyl group, a neopentyl group, a 1-ethylpropyl group, an n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a cyclopropyl group, a cyclopentyl group, and a cyclohexyl group. Preferred examples may include a methyl group, an ethyl group, an n-propyl group, an isopropyl group, an n-butyl group, an isobutyl group, and a tert-butyl group. More preferred examples may include a methyl group, an ethyl group, and an isopropyl group.

The "(C1-C6) alkoxyl group" is used in the present invention to mean a group formed by binding the above described (C1-C6) alkyl group to an oxygen atom. Examples of such a (C1-C6) alkoxyl group may include a methoxy group, an ethoxy group, an n-propoxy group, an isopropoxy group, an n-butoxy group, an isobutoxy group, a tert-butoxy group, an n-pentyloxy group, an isopentyloxy group, a methylbutoxy group, a neopentyloxy group, a 1-ethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 2-ethylbutoxy group, a cyclopropoxy group, a cyclopentyloxy group, and a cyclohexyloxy group. Preferred examples may include a methoxy group, an ethoxy group, an n-propoxy group, an isopropoxy group, an n-butoxy group, an isobutoxy group, and a tert-butoxy group. More preferred examples may include a methoxy group and an ethoxy group.

The "(C1-C4) alkoxy (C1-C4) alkoxyl group" is used in the present invention to mean a linear or branched alkoxyl group containing 1 to 4 carbon atoms selected from among the above described (C1-C6) alkoxyl groups, which is substituted on the carbons of an alkoxyl group containing 1 to 4 carbon atoms selected from among the above described (C1-C6) alkoxyl groups. Examples of such a (C1-C4) alkoxy (C1-C4) alkoxyl group may include a methoxymethoxy group, an ethoxymethoxy group, an isopropoxymethoxy group, a tert-butoxymethoxy group, a 1-methoxyethoxy group, a 2-methoxyethoxy group, a 1-ethoxyethoxy group, a 2-ethoxyethoxy group, a 2-isopropoxyethoxy group, a 2-(tert-butoxy)ethoxy group, a 3-methoxypropoxy group, a 3-ethoxypropoxy group, a 3-isopropoxypropoxy group, a 3-(tert-butoxy)propoxy group, a 4-methoxybutoxy group, a 4-ethoxybutoxy group, a 4-isopropoxybutoxy group, a 4-(tert-butoxy)butoxy group, a 1-methoxy-1-methylethoxy group, a 2-methoxy-1,1-dimethylethoxy group, and a 2-methoxy-2-methylpropoxy group. Preferred examples may include a 2-methoxyethoxy group, a 2-(tert-butoxy)ethoxy group, and a 2-methoxy-2-methylpropoxy group. More preferably, it is a methoxyethoxy group.

The "2-[2-(C1-C4) alkoxyethoxy]ethoxy group" is used in the present invention to mean a group wherein a linear or branched alkoxyl group containing 1 to 4 carbon atoms is substituted on the terminal carbon of an ethoxyethoxy group described regarding the aforementioned (C1-C4) alkoxy (C1-C4) alkoxyl group. Examples of such a 2-[2-(C1-C4) alkoxyethoxy]ethoxy group may include a 2-(2-methoxyethoxy) ethoxy group, a 2-(2-ethoxyethoxy)ethoxy group, a 2-(2-isopropoxyethoxy)ethoxy group, and a 2-[2-(tert-butoxy) ethoxy]ethoxy group. Preferred examples may include a 2-(2-methoxyethoxy)ethoxy group and a 2-[2-(tert-butoxy) ethoxy]ethoxy group. More preferably, it is a 2-(2-methoxyethoxy)ethoxy group.

The "2-{2-[2-(C1-C4) alkoxyethoxy]ethoxy}ethoxy group" is used in the present invention to mean a group wherein a linear or branched alkoxyl group containing 1 to 4 carbon atoms is substituted on the terminal carbon of an ethoxyethoxy group described regarding the aforementioned 2-[2-(C1-C4) alkoxyethoxy]ethoxy group. Examples of such a 2-{2-[2-(C1-C4) alkoxyethoxy]ethoxy}ethoxy group may include a 2-[2-(2-methoxyethoxy)ethoxy]ethoxy group, a 2-[2-(2-ethoxyethoxy)ethoxy]ethoxy group, a 2-[2-(2-isopropoxyethoxy)ethoxy]ethoxy group, and a 2-{2-[2-(tert-butoxy)ethoxy]ethoxy}ethoxy group. Preferred examples may include a 2-[2-(2-methoxyethoxy)ethoxy]ethoxy group and a 2-{2-[2-(tert-butoxy)ethoxy]ethoxy}ethoxy group. More preferably, it is a 2-[2-(2-methoxyethoxy)ethoxy]ethoxy group.

Specific examples of the "(C1-C7) acyl group" used in the present invention may include a formyl group, an acetyl group, a propionyl group, a butyryl group, an isobutyryl group, a valeryl group, an isovaleryl group, a pivaloyl group, a hexanoyl group, a cyclopropylcarbonyl group, a cyclopentylcarbonyl group, and a cyclohexylcarbonyl group. Preferred examples may include an acetyl group, a propionyl group, and a pivaloyl group. More preferably, it is an acetyl group.

The "(C1-C7) acyloxy group" is used in the present invention to mean a group formed by binding the above described (C1-C7) acyl group to an oxygen atom. Examples of such a (C1-C7) acyloxy group may include a formyloxy group, an acetoxy group, a propionyloxy group, a butyryloxy group, an isobutyryloxy group, a valeryloxy group, an isovaleryloxy group, a pivaloyloxy group, a hexanoyloxy group, a cyclopropylcarbonyloxy group, a cyclopentylcarbonyloxy group, and a cyclohexylcarbonyloxy group. Preferred examples may include an acetoxy group, a propionyloxy group, and a pivaloyloxy group. More preferably, it is an acetoxy group.

The "(C1-C6) alkylsulfanyl group" is used in the present invention to mean a group formed by binding the above described (C1-C6) alkyl group to a sulfur atom. Examples of such a (C1-C6) alkylsulfanyl group may include a methylsulfanyl group, ethylsulfanyl group, n-propylsulfanyl group, isopropylsulfanyl group, n-butylsulfanyl group, isobutylsulfanyl group, tert-butylsulfanyl group, pentylsulfanyl group, isopentylsulfanyl group, 2-methylbutylsulfanyl group, neopentylsulfanyl group, 1-ethylpropylsulfanyl group, hexylsulfanyl group, 4-methylpentylsulfanyl group, 3-methylpentylsulfanyl group, 2-methylpentylsulfanyl group, 1-methylpentylsulfanyl group, 3,3-dimethylbutylsulfanyl group, 2,2-dimethylbutylsulfanyl group, 1,1-dimethylbutylsulfanyl group, 1,2-dimethylbutylsulfanyl group, 1,3-dimethylbutylsulfanyl group, 2,3-dimethylbutylsulfanyl group, 2-ethylbutylsulfanyl group, cyclopropylsulfanyl group, cyclopentylsulfanyl group, or cyclohexylsulfanyl group. Preferred examples may include a methylsulfanyl group, an ethylsulfanyl group, a propylsulfanyl group, an isopropylsulfanyl group, a butylsulfanyl group, an isobutylsulfanyl group, and a tert-butylsulfanyl group. More preferred examples may include a methylsulfanyl group and an ethylsulfanyl group.

The "(C1-C6) alkylsulfinyl group" is used in the present invention to mean a group formed by binding the above described (C1-C6) alkyl group to a sulfinyl group (S=O). Examples of such a (C1-C6) alkylsulfinyl group may include a methylsulfinyl group, ethylsulfinyl group, n-propylsulfinyl group, isopropylsulfinyl group, n-butylsulfinyl group, isobutylsulfinyl group, tert-butylsulfinyl group, n-pentylsulfinyl group, isopentylsulfinyl group, 2-methylbutylsulfinyl group, neopentylsulfinyl group, 1-ethylpropylsulfinyl group, n-hexylsulfinyl group, 4-methylpentylsulfinyl group, 3-methylpentylsulfinyl group, 2-methylpentylsulfinyl group, 1-methylpentylsulfinyl group, 3,3-dimethylbutylsulfinyl group, 2,2-dimethylbutylsulfinyl group, 1,1-dimethylbutylsulfinyl group, 1,2-dimethylbutylsulfinyl group, 1,3-dimethylbutylsulfinyl group, 2,3-dimethylbutylsulfinyl group, 2-ethylbutylsulfinyl group, cyclopropylsulfinyl group, cyclopentylsulfinyl group, or cyclohexylsulfinyl group. Preferred examples may include a methylsulfinyl group, an ethylsulfinyl group, an n-propylsulfinyl group, an isopropylsulfinyl group, an n-butylsulfinyl group, an isobutylsulfinyl group, and a tert-butylsulfinyl group. More preferred examples may include a methylsulfinyl group and an ethylsulfinyl group.

The "(C1-C6) alkylsulfonyl group" is used in the present invention to mean a group formed by binding the above described (C1-C6) alkyl group to a sulfonyl group (O=S=O). Examples of such a (C1-C6) alkylsulfonyl group may include a methylsulfonyl group, ethylsulfonyl group, n-propylsulfonyl group, isopropylsulfonyl group, n-butylsulfonyl group, isobutylsulfonyl group, tert-butylsulfonyl group, n-pentylsulfonyl group, isopentylsulfonyl group, 2-methylbutylsulfonyl group, neopentylsulfonyl group, 1-ethylpropylsulfonyl group, n-hexylsulfonyl group, 4-methylpentylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 2-ethylbutylsulfonyl group, cyclopropylsulfonyl group, cyclopentylsulfonyl group, or cyclohexylsulfonyl group. Preferred examples may include a methylsulfonyl group, an ethylsulfonyl group, an n-propylsulfonyl group, an isopropylsulfonyl group, an n-butylsulfonyl group, an isobutylsulfonyl group, and a tert-butylsulfonyl group. More preferred examples may include a methylsulfonyl group and an ethylsulfonyl group.

The "(C1-C6) alkoxycarbonyl group" is used in the present invention to mean a group formed by binding the above described (C1-C6) alkoxyl group to a carbonyl group (C=O). Specific examples of such a (C1-C6) alkoxycarbonyl group may include a methoxycarbonyl group, ethoxycarbonyl group, n-propoxycarbonyl group, isopropoxycarbonyl group, n-butoxycarbonyl group, isobutoxycarbonyl group, tert-butoxycarbonyl group, n-pentyloxycarbonyl group, isopentyloxycarbonyl group, 2-methylbutoxycarbonyl group, neopentyloxycarbonyl group, 1-ethylpropoxycarbonyl group, n-hexyloxycarbonyl group, 4-methylpentyloxycarbonyl group, 3-methylpentyloxycarbonyl group, 2-methylpentyloxycarbonyl group, 1-methylpentyloxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, 2-ethylbutoxycarbonyl group, cyclopropoxycarbonyl group, cyclopentyloxycarbonyl group, or cyclohexyloxycarbonyl group. Preferred examples may include a methoxycarbonyl group, an ethoxycarbonyl group, an n-propoxycarbonyl group, an isopropoxycarbonyl group, an n-butoxycarbonyl group, an isobutoxycarbonyl group, and a tert-butoxycarbonyl group. More preferred examples may include an ethoxycarbonyl group and a tert-butoxycarbonyl group.

The "N—(C1-C6) alkylcarbamoyl group" is used in the present invention to mean a carbamoyl group wherein the above described (C1-C6) alkyl group is monosubstituted with a nitrogen atom. Examples of such an N—(C1-C6) alkylcarbamoyl group may include a methylcarbamoyl group, ethylcarbamoyl group, n-propylcarbamoyl group, isopropylcarbamoyl group, n-butylcarbamoyl group, isobutylcarbamoyl group, tert-butylcarbamoyl group, n-pentylcarbamoyl group, isopentylcarbamoyl group, 2-methylbutylcarbamoyl group, neopentylcarbamoyl group, 1-ethylpropylcarbamoyl group, n-hexylcarbamoyl group, 4-methylpentylcarbamoyl group, 3-methylpentylcarbamoyl group, 2-methylpentylcarbamoyl group, 1-methylpentylcarbamoyl group, 3,3-dimethylbutylcarbamoyl group, 2,2-dimethylbutylcarbamoyl group, 1,1-dimethylbutylcarbamoyl group, 1,2-dimethylbutylcarbamoyl group, 1,3-dimethylbutylcarbamoyl group, 2,3-dimethylbutylcarbamoyl group, 2-ethylbutylcarbamoyl group, cyclopropylcarbamoyl group, cyclopentylcarbamoyl group, or cyclohexylcarbamoyl group. Preferred examples may include a methylcarbamoyl group, an ethylcarbamoyl group, an n-propylcarbamoyl group, an isopropylcarbamoyl group, an n-butylcarbamoyl group, an isobutylcarbamoyl group, and a tert-buylcarbamoyl group. More preferred examples may include a methylcarbamoyl group and an ethylcarbamoyl group.

The "N,N-di(C1-C6) alkylcarbamoyl group" is used in the present invention to mean a carbamoyl group wherein the above described (C1-C6) alkyl group is disubstituted with nitrogen atoms. Examples of such an N,N-di(C1-C6) alkylcarbamoyl group may include a dimethylcarbamoyl group, diethylcarbamoyl group, di(n-propyl)carbamoyl group, diisopropylcarbamoyl group, di(n-butyl)carbamoyl group, diisobutylcarbamoyl group, di(tert-butyl)carbamoyl group, di(n-pentyl)carbamoyl group, diisopentylcarbamoyl group, di(2-methylbutyl)carbamoyl group, dineopentylcarbamoyl group, di(1-ethylpropyl)carbamoyl group, di(n-hexyl)carbamoyl group, di(4-methylpentyl)carbamoyl group, di(3-methylpentyl)carbamoyl group, di(2-methylpentyl)carbamoyl group, di(1-methylpentyl)carbamoyl group, bis(3,3-dimethylbutyl)carbamoyl group, dicyclopropylcarbamoyl group, dicyclopentylcarbamoyl group, or dicyclohexylcarbamoyl group. Preferred examples may include a dimethylcarbamoyl group, a diethylcarbamoyl group, a di(n-propyl) carbamoyl group, a diisopropylcarbamoyl group, and a di(n-butyl)carbamoyl group. More preferred examples may include a dimethylcarbamoyl group and a diethylcarbamoyl group.

With regard to the expression "5- to 7-membered saturated or unsaturated heterocyclic group containing 1 to 4 heteroatoms independently selected from among N, O, and S" in the present invention, examples of such a saturated heterocyclic group may include a tetrahydrofuran-2-yl group, a tetrahydrofuran-3-yl group, a tetrahydropyran-4-yl group, a [1,3]dioxolan-2-yl group, a [1,3]dioxan-2-yl group, a pyrrolidin-1-yl group, a piperidin-1-yl group, a piperidin-4-yl group, an azepan-1-yl group, a morpholin-4-yl group, a thiomorpholin-4-yl group, an okazolidin-3-yl group, an isoxazolidin-2-yl group, a thiazolidin-3-yl group, an imidazolidin-1-yl group, and a piperazin-1-yl group. Examples of an unsaturated heterocyclic group may include a furan-2-yl group, a furan-3-yl group, a thiophen-2-yl group, a thiophen-3-yl group, an oxazol-5-yl group, an isoxazol-5-yl group, a thiazol-5-yl group, a pyrrol-1-yl group, a pyridin-2-yl group, a pyridin-3-yl group, a pyridin-4-yl group, a pyrimidin-4-yl group, a pyrazin-2-yl group, a [1,3,5]triazin-2-yl group, an imidazol-1-yl group, an imidazol-2-yl group, an imidazol-4-yl group, a [1,2,4]triazol-1-yl group, a [1,2,4]triazol-3-yl group, a tetrazol-1-yl group, and a tetrazol-5-yl group.

Specific examples of the above heterocyclic group, which has an oxo group or a (C1-C6) alkyl group as a substituent, may include a 4-methyltetrahydropyran-4-yl group, 2-methyl [1,3]dioxolan-2-yl group, 2-methyl[1,3]dioxan-2-yl group, 5,5-dimethyl[1,3]dioxan-2-yl group, 2-oxopyrrolidin-1-yl group, 2,5-dioxopyrrolidin-1-yl group, 2-oxopiperidin-1-yl group, 2,6-dioxopiperidin-1-yl group, 4-methyl-2,6-dioxopiperidin-1-yl group, 4-isopropyl-2,6-dioxopiperidin-1-yl group, 1-methylpiperidin-4-yl group, 3,5-dioxomorpholin-4-yl group, 4-methyl-piperazin-1-yl group, 5-methylfuran-2-yl group, 2,5-dioxo-2,5-dihydropyrrol-1-yl group, 2-oxo-2H-pyridin-1-yl group, or 1-methyl-1H-imidazol-2-yl group.

Specific examples of the "5- to 7-membered saturated cyclic amino group, which may contain 1 to 4 heteroatoms independently selected from among N, O, and S" in the present invention may include a pyrrolidin-1-yl group, a piperidin-1-yl group, a piperidin-4-yl group, an azepan-1-yl group, a morpholin-4-yl group, a thiomorpholin-4-yl group, an oxazolidin-3-yl group, an isoxazolidin-2-yl group, a thiazolidin-3-yl group, an imidazolidin-1-yl group, and a piperazin-1-yl group. Preferred examples may include a pyrrolidin-1-yl group, a piperidin-1-yl group, a morpholin-4-yl group, an oxazolidin-3-yl group, and a piperazin-1-yl group. More preferred examples may include a pyrrolidin-1-yl group, a piperidin-1-yl group, and a morpholin-4-yl group.

The "ethyleneoxy group" is used in the present invention to mean a substituent that forms a cyclic structure together with an aromatic hydrocarbon group or an aromatic heterocyclic group that is represented by Ar in the general formula (1), via oxygen atoms and carbon atoms at the ends.

The "(C1-C2) alkylenedioxy group" is used in the present invention to mean O—(CH$_2$)$_{1-2}$—O. This (C1-C2) alkylenedioxy group is a substituent that forms a cyclic structure together with an aromatic hydrocarbon group or an aromatic heterocyclic group that is represented by Ar in the general formula (1), via oxygen atoms at both ends. Specific examples of such a (C1-C2) alkylenedioxy group may include a methylenedioxy group and an ethylenedioxy group.

A preferred example of the "linear, branched, or cyclic alkyl group" represented by R in the compound represented by the general formula (1) of the present invention may be a (C1-C12) alkyl group. Other than the groups exemplified regarding the above described (C1-C6) alkyl group, examples of such a (C1-C12) alkyl group may include an n-heptyl group, 1-methylhexyl group, 2-methylhexyl group, 3-methylhexyl group, 4-methylhexyl group, 5-methylhexyl group, 1-propylbutyl group, 1,3-dimethylpentyl group, 1,4-dimethylpentyl group, 4,4-dimethylpentyl group, octyl group, 1-methylheptyl group, 2-methylheptyl group, 3-methylheptyl group, 4-methylheptyl group, 5-methylheptyl group, 6-methylheptyl group, 1-propylpentyl group, 2-ethylhexyl group, 1,3-dimethylhexyl group, 1,4-dimethylhexyl group, 1,5-dimethylhexyl group, 5,5-dimethylhexyl group, n-nonyl group, 3-methyloctyl group, 4-methyloctyl group, 5-methyloctyl group, 6-methyloctyl group, 1-propylhexyl group, 2-ethylheptyl group, 1,3-dimethylheptyl group, 1,4-dimethylheptyl group, 1,5-dimethylheptyl group, 1,6-dimethylheptyl group, 6,6-dimethylheptyl group, n-decyl group, 1-methylnonyl group, 3-methylnonyl group, 8-methylnonyl group, 3-ethyloctyl group, 3,7-dimethyloctyl group, 7,7-dimethyloctyl group, cyclopropyl group, cyclopentyl group, cyclohexyl group, cyclohexylethyl group, 4-methylcyclohexyl group, 2,6-dimethylcyclohexyl group, 4,4-dimethylcyclohexyl group, cycloheptyl group, adamantan-1-yl group, or adamantan-2-yl group. In addition to the groups that are given as preferred examples of the above described (C1-C6) alkyl group, a 1-methylhexyl group, a 1,4-dimethylpentyl group, a 1-methylheptyl group, a 1,4-dimethylhexyl group, a 1,5-dimethylhexyl group, and a 1,6-dimethylheptyl group are preferable. In addition to the groups that are given as more preferred examples of the above described (C1-C6) alkyl group, a 1,4-dimethylpentyl group and a 1,5-dimethylhexyl group are more preferable.

The "aromatic hydrocarbon group" and "5- to 7-membered heterocyclic group containing 1 to 4 heteroatoms independently selected from among N, O, and S" that are represented by R in the compound represented by the general formula (1) of the present invention have the same meanings as those of the aforementioned "aromatic hydrocarbon group" and "5- to 7-membered heterocyclic group containing 1 to 4 heteroatoms independently selected from among N, O, and S" in the present invention. Specific examples of these groups and preferred examples thereof are also the same as those given above.

With regard to R in the general formula (1) of the present invention, examples of the linear, branched, or cyclic alkyl group, which may have a substituent, the aromatic hydrocarbon group, which may have a substituent, or the 5- to 7-heterocyclic group containing 1 to 4 heteroatoms independently selected from among N, O, and S, which may have a substituent, may include groups represented by any one of the above described formulas (2) to (6).

In each of these formulas, the bond indicated with ● (a circle) represents a bond with a nitrogen atom.

Preferred examples of the "(C1-C6) alkyl group" represented by R4 in the formula (2) may include a methyl group, an ethyl group, a propyl group, an isopropyl group, a butyl group, an isobutyl group, an isopentyl group, a 4-methylpentyl group, and a 3,3-dimethylbutyl group. More preferred examples may include a methyl group, an ethyl group, a propyl group, an isopentyl group, and a 4-methylpentyl group.

The "C2-C10 alkenyl group" is used in the present invention to mean a linear, branched, or cyclic hydrocarbon group containing 2 to 10 carbon atoms, which has an unsaturated double bond. Examples of such a C2-C10 alkenyl group may include a vinyl group, allyl group, propen-1-yl group, buten-1-yl group, buten-2-yl group, buten-3-yl group, 2-methylpropen-1-yl group, penten-1-yl group, penten-2-yl group, penten-3-yl group, penten-4-yl group, 3-methylbuten-1-yl group, 3-methylbuten-2-yl group, hexen-1-yl group, 4-methylpenten-1-yl group, 3-methylpenten-1-yl group, 3,3-dimethylbuten-1-yl group, hepten-1-yl group, hepten-2-yl group, 5-methylhexen-1-yl group, 4,4-dimethylhexen-1-yl group, octen-1-yl group, 6-methylhepten-1-yl group, 5,5-dimethylhexen-1-yl group, nonen-1-yl group, 7-methylocten-1-yl group, 6,6-dimethylhepten-1-yl group, decen-1-yl group, cyclopenten-3-yl group, or cyclohexen-1-yl group. Preferred examples may include a vinyl group, an allyl group, a propen-1-yl group, a buten-1-yl group, penten-1-yl group, a 3-methylbuten-1-yl group, a 4-methylpenten-1-yl group, and a cyclopenten-3-yl group. More preferred examples may include a vinyl group, a propen-1-yl group, a buten-1-yl group, a 3-methylbuten-1-yl group, and a 4-methylpenten-1-yl group.

The "C2-C10 alkynyl group" is used in the present invention to mean a linear or branched hydrocarbon group containing 2 to 10 carbon atoms, which has an unsaturated triple bond. Examples of such a C2-C10 alkynyl group may include an ethynyl group, a propyn-1-yl group, a propyn-3-yl group, a butyn-1-yl group, a butyl-3-yl group, a butyn-4-yl group, a 3-methylpropyn-3-yl group, a 1-methylbutyn-3-yl group, a 1-ethylbutyn-3-yl group, a pentyn-1-yl group, a pentyn-3-yl group, a pentyn-4-yl group, a 3-methylbutyn-1-yl group, a hexyn-1-yl group, a 4-methylpentyn-1-yl group, a heptyn-1-yl group, an octyn-1-yl group, an nonyn-1-yl group, and a decyn-1-yl group. Preferred examples may include an ethynyl group, a propyn-1-yl group, a propyn-3-yl group, a butyn-1-yl group, a butyn-3-yl group, a pentyn-1-yl group, a pentyn-3-yl group, a 3-methylbutyn-1-yl group, and a 4-methylpentyn-1-yl group. More preferred examples may include an ethynyl group, a propyn-1-yl group, a butyn-1-yl group, a 3-methylbutyn-1-yl group, and a 4-methylpentyn-1-yl group.

When R in the general formula (1) of the present invention is represented by the formula (2), the "C1-4 alkoxymethyl group" represented by R6 means an alkoxyl group containing 1 to 4 carbon atoms from among the above described (C1-C6) alkoxyl groups. Examples of such a C1-4 alkoxymethyl group may include a methoxymethyl group, an ethoxymethyl group, a propoxymethyl group, an isopropoxymethyl group, a butoxymethyl group, an isobutoxymethyl group, and a tert-butoxymethyl group. Preferred examples may include a methoxymethyl group, an ethoxymethyl group, and an isopropoxymethyl group. More preferred examples may include a methoxymethyl group and an ethoxymethyl group.

When R in the general formula (1) of the present invention is represented by the formula (2), the "(C1-C10) alkyl group" represented by R6 means a linear, branched, or cyclic alkyl group containing 1 to 10 carbon atoms from among the above described (C1-C12) alkyl groups. More preferred examples of such a (C1-C10) alkyl group may include a methyl group, an ethyl group, a propyl group, an isopentyl group, a 4-methylpentyl group, and a cyclohexyl group.

The "halogeno (C1-C3) alkyl group" is used in the present invention to mean a linear or branched alkyl group containing 1 to 3 carbon atoms, which is substituted with the aforementioned 1 to 7 halogeno groups. Examples of such a halogeno (C1-C3) alkyl group may include a fluoromethyl group, a difluoromethyl group, a trifluoromethyl group, a 2-fluoroethyl group, a 2,2-difluoroethyl group, a 2,2,2-trifluoroethyl group, a 1,1,2,2-tetrafluoroethyl group, a 3-fluoropropyl group, a 2,2,3,3-tetrafluoropropyl group, a dichloromethyl group, a trichloromethyl group, and a 2,2,2-trichloroethyl group. Preferred examples may include a fluoromethyl group, a difluoromethyl group, a trifluoromethyl group, a 2,2,2-trifluoroethyl group, and a 1,1,2,2-tetrafluoroethyl group. More preferred examples may include a trifluoromethyl group and a 2,2,2-trifluoroethyl group.

When R in the general formula (1) of the present invention is represented by the formula (3) or (4), each substituent has the same meanings as those of the aforementioned each substituent in the present invention. Specific examples of such groups and preferred examples thereof are also the same as those of the aforementioned each substituent in the present invention.

When R in the general formula (1) of the present invention is represented by the formula (5), examples of the "(C3-C10) cycloalkyl group" may include a cyclopropyl group, a cyclopentyl group, a cyclohexyl group, a cycloheptyl group, a cyclooctyl group, and an adamantyl group. Preferred examples may include a cyclopropyl group, a cyclopentyl group, and a cyclohexyl group. More preferred examples may include a cyclopentyl group and a cyclohexyl group.

When R in the general formula (1) of the present invention is represented by the formula (6), examples of the "α-amino acid residue" are as follows (the side chain is described in each parenthesis): a glycine residue (hydrogen atom), an alanine residue (methyl group), a norvaline residue (ethyl group), a valine residue (isopropyl group), a leucine residue (isobutyl group), an isoleucine residue (sec-butyl group), a phenylalanine residue (benzyl group), a lysine residue (4-aminobutyl group), a serine residue (hydroxymethyl group), a threonine residue (1-hydroxyethyl group), an asparagine residue (carbamoylmethyl group), a glutamine residue (2-carbamoylethyl group), an aspartic acid residue (carboxymethyl group), a glutamic acid residue (2-carboxyethyl group), a methionine residue (2-methylsulfanylethyl group), and a histidine residue (imidazol-4-ylmethyl group). Preferred examples may include a glycine residue, an alanine residue, a norvaline residue, a valine residue, a serine residue, and a threonine residue. More preferred examples may include a glycine residue, an alanine residue, and a serine residue.

Examples of the "amino acid side chain, which may be protected by a protecting group" in the present invention may include a serine side chain protected by a methyl group (methoxymethyl group), a serine side chain protected by a tert-butyl group (tert-butoxymethyl group), a serine side chain protected by a benzyl group (benzyloxymethyl group), a threonine side chain protected by a methyl group (1-methoxyethyl group), a cysteine side chain protected by a methyl group (methylsulfanylmethyl group), a cysteine side chain protected by a tert-butyl group (tert-butylsulfanylmethyl group), a tyrosine side chain protected by a methyl group (4-methoxybenzyl group), an aspartic acid side chain protected by a methyl group (methoxycarbonylmethyl group), an aspartic acid side chain protected by a tert-butyl group (tert-butoxycarbonylmethyl group), a glutamic acid side chain protected by a methyl group (2-methoxycarbonylethyl group), a glutamic acid side chain protected by a tert-butyl group (2-tert-butoxycarbonylethyl group), and a lysine side chain protected by a tert-butoxycarbonyl group (4-(tert-butoxycarbonyl)aminobutyl group).

Preferred examples of an amino acid side chain protected by a protecting group may include a glycine side chain, an alanine side chain, a norvaline side chain, a valine side chain, a leucine side chain, an isoleucine side chain, a serine side chain protected by a methyl group, a serine side chain protected by a tert-butyl group, a threonine side chain protected by a methyl group, a cysteine side chain protected by a methyl group, and a methionine side chain. More preferred examples may include a glycine side chain, an alanine side chain, a norvaline side chain, a valine side chain, and a serine side chain protected by a methyl group.

The "(C1-C6) alkylamino group" is used in the present invention to mean the above described (C1-C6) alkyl group that is monosubstituted with an amino group. Examples of such a (C1-C6) alkylamino group may include a methylamino group, ethylamino group, n-propylamino group, isopropylamino group, n-butylamino group, isobutylamino group, tert-butylamino group, n-pentylamino group, isopentylamino group, 2-methylbutylamino group, neopentylamino group, 1-ethylpropylamino group, n-hexylamino group, 4-methylpentylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 2-ethylbutylamino group, cyclopropylamino group, cyclopentylamino group, or cyclohexylamino group. Preferred examples may include a methylamino group, an ethylamino group, an n-propylamino group, an isopropylamino group, an n-butylamino group, an isobutylamino group, and a tert-butylamino group. More preferred examples may include a methylamino group, an ethylamino group, and an isopropylamino group.

The "di(C1-C6) alkylamino group" is used in the present invention to mean the above described (C1-C6) alkyl group that is disubstituted with amino groups. Examples of such a di(C1-C6) alkylamino group may include a dimethylamino group, a diethylamino group, a di(n-propyl)amino group, a diisopropylamino group, a di(n-butyl)amino group, a diisobutylamino group, a di(n-pentyl)amino group, a di(n-hexyl)amino group, a bis(3,3-dimethylbutyl)amino group, a dicyclopropylamino group, a dicyclopentylamino group, and a dicyclohexylamino group. Preferred examples may include a dimethylamino group, a diethylamino group, a di(n-propyl) amino group, a diisopropylamino group, a di(n-butyl)amino group, and a diisobutylamino group. More preferred examples may include a dimethylamino group and a diethylamino group.

Examples of a group that does not have a substituent from among the "5- to 7-membered saturated or unsaturated heterocyclic groups containing 1 to 4 heteroatoms independently selected from among N, O, and S, which may be substituted with 1 to 4 identical or different groups selected from substituent group [F] consisting of an oxo group, a (C1-C6) alkyl group, a phenyl group, and a benzyl group" represented by R12 in the formula (6) in the general formula (1) of the present invention may include: saturated heterocyclic groups such as a tetrahydrofuran-2-yl group, a tetrahydrofuran-3-yl group, a tetrahydropyran-4-yl group, a pyrrolidin-1-yl group, a piperidin-1-yl group, a piperidin-4-yl group, an azepan-1-yl group, a morpholin-4-yl group, a thiomorpholin-4-yl group, an oxazolidin-3-yl group, an isoxazolidin-2-yl group, a thiazolidin-3-yl group, an imidazolidin-1-yl group, and a piperazin-1-yl group; and unsaturated heterocyclic groups such as a furan-2-yl group, a furan-3-yl group, a thiophen-2-yl group, a thiophen-3-yl group, an oxazol-5-yl group, an isoxazol-5-yl group, a thiazol-5-yl group, a pyrrol-1-yl group, a pyridin-2-yl group, a pyridin-3-yl group, a pyridin-4-yl group, a pyrimidin-4-yl group, a pyrazin-2-yl group, a [1,3,5]triazin-2-yl group, an imidazol-2-yl group, an imidazol-4-yl group, a [1,2,4]triazol-3-yl group, and a tetrazol-5-yl group.

Examples of the above heterocyclic group, which has a substituent, may include a 2-oxotetrahydrofuran-3-yl group, a 4-methyltetrahydropyran-4-yl group, a 2-oxopyrrolidin-1-yl group, a 2,5-dioxopyrrolidin-1-yl group, a 2-oxopiperidin-1-yl group, a 2,6-dioxopiperidin-1-yl group, a 4-methyl-2,6-dioxopiperidin-1-yl group, a 4-isopropyl-2,6-dioxopiperidin-1-yl group, a 1-methylpiperidin-4-yl group, a 3,5-dioxomorpholin-4-yl group, a 4-methyl-piperazin-1-yl group, a 5-methylfuran-2-yl group, a 2,5-dioxo-2,5-dihydropyrrol-1-yl group, a 2-oxo-2H-pyridin-1-yl group, and a 1-methyl-1H-imidazol-2-yl group. Preferred examples may include a tetrahydrofuran-2-yl group, a tetrahydrofuran-3-yl group, a tetrahydropyran-4-yl group, a pyridin-2-yl group, a pyridin-3-yl group, a pyridin-4-yl group, and a 2-oxotetrahydrofuran-3-yl group. More preferred examples may include a tetrahydropyran-4-yl group and a pyridin-3-yl group.

Examples of X in the general formula (1) of the present invention may include O, S, NH, N—CH$_3$, and N—CN. X is preferably O or S.

Specific examples of Ar in the general formula (1) of the present invention may include a phenyl group, 2-fluorophenyl group, 2-chlorophenyl group, 2-hydroxyphenyl group, 2-cyanophenyl group, 2-trifluoromethylphenyl group, 2-trifluoromethoxyphenyl group, 2-nitrophenyl group, 2-methylphenyl group, 2-ethylphenyl group, 2-methoxyphenyl group, 2-ethoxyphenyl group, 2-aminophenyl group, 2-dimethylaminophenyl group, 3-fluorophenyl group, 3-chlorophenyl group, 3-hydroxyphenyl group, 3-cyanophenyl group, 3-trifluoromethylphenyl group, 3-trifluoromethoxyphenyl group, 3-nitrophenyl group, 3-methylphenyl group, 3-ethylphenyl group, 3-propylphenyl group, 3-isopropylphenyl group, 3-butylphenyl group, 3-cyclohexylphenyl group, 3-methoxyphenyl group, 3-ethoxyphenyl group, 3-isopropoxyphenyl group, 3-isobutoxyphenyl group, 3-(2-fluoroethyl)phenyl group, 3-(2,2-difluoroethyl)phenyl group, 3-(2,2,2-trifluoroethyl)phenyl group, 3-(2-chloroethyl)phenyl group, 3-methoxymethoxyphenyl group, 3-(2-methoxyethoxy)phenyl group, 3-(2-methoxyethoxy)methoxyphenyl group, 3-[2-(2-methoxyethoxy)ethoxy]phenyl group, 3-{2-[2-(2-methoxyethoxy)ethoxy]ethoxy}phenyl group, 3-(2-oxopropoxy)phenyl group, 3-(2-acetoxyethoxy)phenyl group, 3-(2-pivaloyloxyethoxy)phenyl group, 3-(2-methylsulfanylethoxy)phenyl group, 3-(2-methylsulfenylethoxy)phenyl group, 3-(2-methylsulfonylethoxy)phenyl group, 3-(2-ethylsulfonylethoxy)phenyl group, 3-(3-methylsulfonylpropoxy)phenyl group, 3-carboxymethoxyphenyl group, 3-methoxycarbonylmethoxyphenyl group, 3-ethoxycarbonylmethoxyphenyl group, 3-tert-butoxycarbonylmethoxyphenyl group, 3-(3-methoxycarbonylpropoxy)phenyl group, 3-(3-ethoxycarbonylpropoxy)phenyl group, 3-(3-tert-butoxycarbonylpropoxy)phenyl group, 3-dimethylcarbamoylmethoxyphenyl group, 3-(2-dimethylcarbamoylethoxy)phenyl group, 3-(3-dimethylcarbamoylpropoxy)phenyl group, 3-(2-pyrrolidin-1-yl-2-oxoethoxy)phenyl group, 3-(4-pyrrolidin-1-yl-4-oxobutoxy)phenyl group, 3-(2-piperidin-1-yl-2-oxoethoxy)phenyl group, 3-(4-piperidin-1-yl-4-oxobutoxy)phenyl group, 3-(2-morpholin-4-yl-2-oxoethoxy)phenyl group, 3-(4-morpholin-4-yl-4-oxobutoxy)phenyl group, 3-[2-(4-methylpiperazin-1-yl)-2-oxoethoxy]phenyl group, 3-[4-(4-methylpiperazin-1-yl)-4-oxobutoxy]phenyl group,
3-dimethylaminoethoxyphenyl group, 3-dimethylaminopropoxyphenyl group, 3-diethylaminoethoxyphenyl group, 3-diethylaminopropoxyphenyl group, 3-(2-acetylaminoethoxy)phenyl group, 3-(3-acetylaminopropoxy)phenyl group, 3-[2-(N-acetyl-N-methylamino)ethoxy]phenyl group, 3-[3-(N-acetyl-N-methylamino)propoxy]phenyl group, 3-(2-tert-butoxycarbonylaminoethoxy)phenyl group, 3-(3-tert-butoxycarbonylaminopropoxy)phenyl group, 3-(2-benzyloxycarbonylaminoethoxy)phenyl group, 3-(3-benzyloxycarbonylaminopropoxy)phenyl group, 3-benzyloxyphenyl group, 3-(2-phenylethoxy)phenyl group, 3-(3-phenylpropoxy)phenyl group, 3-(tetrahydrofuran-2-ylmethoxy)phenyl group, 3-(tetrahydropyran-4-ylmethoxy)phenyl group, 3-[2-(tetrahydropyran-4-yl)ethoxy]phenyl group, 3-([1,3]dioxolan-2-ylmethoxy)phenyl group, 3-(2-methyl[1,3]dioxolan-2-ylmethoxy)phenyl group, 3-[2-([1,3]dioxolan-2-yl)ethoxy]phenyl group, 3-[2-(2-methyl[1,3]dioxolan-2-yl)ethoxy]phenyl group, 3-[2-([1,3]dioxan-2-yl)ethoxy]phenyl group, 3-[2-(2-methyl[1,3]dioxan-2-yl)ethoxy]phenyl group, 3-(2-pyrrolidin-1-ylethoxy)phenyl group, 3-(3-pyrrolidin-1-ylpropoxy)phenyl group, 3-(2-piperidin-1-ylethoxy)phenyl group, 3-(3-piperidin-1-ylpropoxy)phenyl group, 3-(2-morpholin-4-ylethoxy)phenyl group, 3-(3-morpholin-4-ylpropoxy)phenyl group, 3-[2-(4-methyl)piperazin-1-ylethoxy]phenyl group, 3-[3-(4-methyl)piperazin-1-ylpropoxy]phenyl group, 3-pyridin-2-ylmethoxyphenyl group, 3-pyridin-3-ylmethoxyphenyl group, 3-pyridin-4-ylmethoxyphenyl group, 3-(2-pyridin-2-ylethoxy)phenyl group, 3-(2-pyridin-3-ylethoxy)phenyl group, 3-(2-pyridin-4-ylethoxy)phenyl group,
3-(3-pyridin-2-ylpropoxy)phenyl group, 3-(3-pyridin-3-ylpropoxy)phenyl group, 3-(3-pyridin-4-ylpropoxy)phenyl group, 3-pyrimidin-2-ylmethoxyphenyl group, 3-(2-pyrimidin-2-ylethoxy)phenyl group, 3-[1,3,5]triazin-2-ylmethoxyphenyl group, 3-(2-[1,3,5]triazin-2-ylethoxy)phenyl group, 3-[2-(1H-tetrazol-5-yl)ethoxy]phenyl group, 3-[3-(1H-tetrazol-5-yl)propoxy]phenyl group, 3-aminophenyl group, 3-dimethylaminophenyl group, 3-diethylaminophenyl group, 3-acetylaminophenyl group, 3-propionylaminophenyl group, 3-pyrrolidin-1-ylphenyl group, 3-piperidin-1-ylphenyl group, 3-morpholin-4-ylphenyl group, 3-(4-methylpiperazin-1-yl)phenyl group, 4-fluorophenyl group, 4-chlorophenyl group, 4-hydroxyphenyl group, 4-cyanophenyl group, 4-trifluoromethylphenyl group, 4-trifluoromethoxyphenyl group, 4-nitrophenyl group, 4-methylphenyl group, 4-ethylphenyl group, 4-propylphenyl group, 4-isopropylphenyl group, 4-butylphenyl group, 4-cyclohexylphenyl group, 4-methoxyphenyl group, 4-ethoxyphenyl group, 4-isopropoxyphenyl group, 4-isobutoxyphenyl group, 4-(2-fluoroethyl)phenyl group, 4-(2,2-difluoroethyl)phenyl group, 4-(2,2,2-trifluoroethyl)phenyl group, 4-(2-chloroethyl)phenyl group, 4-methoxymethoxyphenyl group, 4-(2-methoxyethoxy)phenyl group, 4-(2-methoxyethoxy)methoxyphenyl group, 4-[2-(2-methoxyethoxy)ethoxy]phenyl group, 4-{2-[2-(2-methoxyethoxy)ethoxy]ethoxy}phenyl group, 4-(2-oxopropoxy)phenyl group, 4-(2-acetoxyethoxy)phenyl group, 4-(2-pivaloyloxyethoxy)phenyl group, 4-(2-methylsulfanylethoxy)phenyl group, 4-(2-methylsulfenylethoxy)phenyl group, 4-(2-methylsulfonylethoxy)phenyl group, 4-(2-ethylsulfonylethoxy)phenyl group, 4-(3-methylsulfonylpropoxy)phenyl group, 4-carboxymethoxyphenyl group, 4-methoxycarbonylmethoxyphenyl group, 4-ethoxycarbonylmethoxyphenyl group, 4-tert-butoxycarbonylmethoxyphenyl group, 4-(3-methoxycarbonylpropoxy)phenyl group, 4-(3-ethoxycarbonylpropoxy)phenyl group, 4-(3-tert-butoxycarbonylpropoxy)phenyl group, 4-dimethylcarbamoylmethoxyphenyl group, 4-(2-dimethylcarbamoylethoxy)phenyl group, 4-(3-dimethylcarbamoylpropoxy)phenyl group, 4-(2-pyrrolidin-1-yl-2-oxoethoxy)phenyl group, 4-(4-pyrrolidin-1-yl-4-oxobutoxy)phenyl group, 4-(2-piperidin-1-yl-2-oxoethoxy)phenyl group, 4-(4-piperidin-1-yl-4-oxobutoxy)phenyl group, 4-(2-morpholin-4-yl-2-oxoethoxy)phenyl group, 4-(4-morpholin-4-yl-4-oxobutoxy)phenyl group, 4-[2-(4-methylpiperazin-1-yl)-2-oxoethoxy]phenyl group, 4-[4-(4-methylpiperazin-1-yl)-4-oxobutoxy]phenyl group, 4-dimethylaminoethoxyphenyl group, 4-dimethylaminopropoxyphenyl group, 4-diethylaminoethoxyphenyl group, 4-diethylaminopropoxyphenyl group, 4-(2-acetylaminoethoxy)phenyl group, 4-(3-acetylaminopropoxy)phenyl group, 4-[2-(N-acetyl-N-methylamino)ethoxy]phenyl group, 4-[3-(N-acetyl-N-methylamino)propoxy]phenyl group, 4-(2-tert-butoxycarbonylaminoethoxy)phenyl group, 4-(3-tert-butoxycarbonylaminopropoxy)phenyl group, 4-(2-benzyloxycarbonylaminoethoxy)phenyl group, 4-(3-benzyloxycarbonylaminopropoxy)phenyl group, 4-benzyloxyphenyl group, 4-(2-phenylethoxy)phenyl group, 4-(3-phenylpropoxy)phenyl group, 4-(tetrahydrofuran-2-ylmethoxy)phenyl group, 4-(tetrahydropyran-4-ylmethoxy)phenyl group, 4-[2-(tetrahydropyran-4-yl)ethoxy]phenyl group, 4-([1,3]dioxolan-2-ylmethoxy)phenyl group, 4-(2-methyl[1,3]dioxolan-2-ylmethoxy)phenyl group, 4-[2-([1,3]dioxolan-2-yl)ethoxy]phenyl group, 4-[2-(2-methyl[1,3]dioxolan-2-yl)ethoxy]phenyl group, 4-[2-([1,3]dioxan-2-yl)ethoxy]phenyl group, 4-[2-(2-methyl[1,3]dioxan-2-yl)ethoxyl]phenyl group, 4-(2-pyrrolidin-1-ylethoxy)phenyl group, 4-(3-pyrrolidin-1-ylpropoxy)phenyl group, 4-(2-piperidin-1-ylethoxy)phenyl group, 4-(3-piperidin-1-ylpropoxy)phenyl group, 4-(2-morpholin-4-ylethoxy)phenyl group, 4-(3-morpholin-4-ylpropoxy)phenyl group, 4-[2-(4-methyl)piperazin-1-ylethoxy]phenyl group, 4-[3-(4-methyl)piperazin-1-ylpropoxy]phenyl group, 4-pyridin-2-ylmethoxyphenyl group, 4-pyridin-3-ylmethoxyphenyl group, 4-pyridin-4-ylmethoxyphenyl group, 4-(2-pyridin-2-ylethoxy)phenyl group, 4-(2-pyridin-3-ylethoxy)phenyl group, 4-(2-pyridin-4-ylethoxy)phenyl group, 4-(3-pyridin-2-ylpropoxy)phenyl group, 4-(3-pyridin-3-ylpropoxy)phenyl group, 4-(3-pyridin-4-ylpropoxy)phenyl group, 4-pyrimidin-2-ylmethoxyphenyl group, 4-(2-pyrimidin-2-ylethoxy)phenyl group, 4-[1,3,5]triazin-2-ylmethoxyphenyl group, 4-(2-[1,3,5]triazin-2-ylethoxy)phenyl group, 4-[2-(1H-tetrazol-5-yl)ethoxy]phenyl group, 4-[3-(1H-tetrazol-5-yl)propoxy]phenyl group, 4-aminophenyl group, 4-dimethylaminophenyl group, 4-diethylaminophenyl group, 4-acetylaminophenyl group, 4-propionylaminophenyl group, 4-pyrrolidin-1-ylphenyl group, 4-piperidin-1-ylphenyl group, 4-morpholin-4-ylphenyl group, 4-(4-methylpiperazin-1-yl)phenyl group, 3,4-dihydrophenyl group, 2,4-dimethoxyphenyl group, 3,4-dimethoxyphenyl group, 3,4-bis(2-methoxyethoxy)phenyl group, 3,4,5-trimethoxyphenyl group, 2,3-dihydrobenzofuran-5-yl group, 3,4-methylenedioxyphenyl group, 3,4-ethylenedioxyphenyl group, naphthalen-1-yl group, naphthalen-2-yl group, furan-2-yl group, 5-methylfuran-2-yl group, 5-acetylfuran-2-yl group, furan-3-yl group, thiophen-2-yl group, 5-methylthiophen-2-yl group, 5-acetylthiophen-2-yl group, thiophen-3-yl group, oxazol-5-yl group, isoxazol-5-yl group, thiazol-5-yl group, pyridin-2-yl group, 1-oxopyridin-2-yl group, 6-chloropyridin-2-yl group, 6-methylpyridin-2-yl group, 6-methoxypyridin-2-yl group, pyridin-3-yl group, 1-oxopyridin-3-yl group, 6-chloropyridin-3-yl group, 6-methylpyridin-3-yl group, 6-methoxypyridin-3-yl group, pyridin-4-yl group, 1-oxopyridin-4-yl group, 2-chloropyridin-4-yl group, 2-methylpyridin-4-yl group, 2-methoxypyridin-4-yl group, 2,6-dimethoxypyridin-4-yl group, pyrimidin-4-yl group, pyrazin-2-yl group, or [1,3,5]triazin-2-yl group.

Preferred examples of such Ar may include a phenyl group, 3-chlorophenyl group, 3-hydroxyphenyl group, 3-methoxyphenyl group, 3-(2-methoxyethoxy)phenyl group, 3-dimethylaminoethoxyphenyl group, 3-dimethylaminopropoxyphenyl group, 3-(tetrahydrofuran-2-ylmethoxy)phenyl group, 3-(tetrahydropyran-4-ylmethoxy)phenyl group, 3-(2-morpholin-4-ylethoxy)phenyl group, 3-(3-morpholin-4-ylpropoxy)phenyl group, 3-pyridin-3-ylmethoxyphenyl group, 3-pyridin-4-ylmethoxyphenyl group, 3-(2-pyridin-3-ylethoxy)phenyl group, 3-(2-pyridin-4-ylethoxy)phenyl group, 3-aminophenyl group, 3-dimethylaminophenyl group, 3-acetylaminophenyl group, 3-morpholin-4-ylphenyl group, 4-hydroxyphenyl group, 4-trifluoromethoxyphenyl group, 4-methoxyphenyl group, 4-ethoxyphenyl group, 4-(2-methoxyethoxy)phenyl group, 4-(2-methoxyethoxy)methoxyphenyl group, 4-[2-(2-methoxyethoxy)ethoxy]phenyl group, 4-{2-[2-(2-methoxyethoxy)ethoxy]ethoxy}phenyl group, 4-dimethylaminoethoxyphenyl group, 4-dimethylaminopropoxyphenyl group, 4-benzyloxyphenyl group, 4-(tetrahydrofuran-2-ylmethoxy)phenyl group, 4-(tetrahydropyran-4-ylmethoxy)phenyl group, 4-(2-morpholin-4-ylethoxy)phenyl group, 4-(3-morpholin-4-ylpropoxy)phenyl group, 4-pyridin-3-ylmethoxyphenyl group, 4-pyridin-4-ylmethoxyphenyl group, 4-(2-pyridin-3-ylethoxy)phenyl group, 4-(2-pyridin-4-ylethoxy)phenyl group, 4-aminophenyl group, 4-dimethylaminophenyl group, 4-acetylaminophenyl group, 4-morpholin-4-ylphenyl group, 3,4-dihydrophenyl group, 3,4-dimethoxyphenyl group, 3,4-bis(2-methoxyethoxy)phenyl group, 3,4,5-trimethoxyphenyl group, 2,3-dihydrobenzofuran-5-yl group, 3,4-methylenedioxyphenyl group, 3,4-ethylenedioxyphenyl group, pyridin-3-yl group, pyridin-4-yl group, thiophen-2-yl group, or thiophen-3-yl group. More preferred examples may include a 3-chlorophenyl group, a 3-hydroxyphenyl group, a 3-methoxyphenyl group, a 3-(tetrahydrofuran-2-ylmethoxy)phenyl group, a 3-(2-morpholin-4-ylethoxy)phenyl group, a 3-pyridin-3-ylmethoxyphenyl group, a 4-hydroxyphenyl group, a 4-methoxyphenyl group, a 4-(2-(2-(2-methoxyethoxy)ethoxy)ethoxy)phenyl group, a 4-(tetrahydropyran-4-ylmethoxy)phenyl group, a 4-(2-morpholin-4-ylethoxy)phenyl group, a 4-aminophenyl group, a 3,4-dimethoxyphenyl group, a 3,4,5-trimethoxyphenyl group, a 2,3-dihydrobenzofuran-5-yl group, a 3,4-methylenedioxyphenyl group, and a thiophen-2-yl group.

Specific examples of R in the general formula (1) of the present invention may include a methyl group, ethyl group, propyl group, isopropyl group, butyl group, sec-butyl group, isobutyl group, cyclopentyl group, 1,4-dimethylpentyl group, cyclohexyl group, cyclohexylmethyl group, 1,5-dimethylhexyl group, adamantan-1-yl group, 4-hydroxycyclohexyl group, phenyl group, 4-hydroxyphenyl group, 3-acetylphenyl group, benzyl group, 1-phenylethyl group, 2-phenyl-1-methylethyl group, 3-phenylpropyl group, 3-phenyl-1-methylpropyl group, 1-phenylpropyl group, 1,2,3,4-tetrahydronaphthalen-1-yl group, 3-hydroxybenzyl group, 3-methoxybenzyl group, 3,4-methylenedioxybenzyl group, 3,4,5-trimethoxybenzyl group, 1-(3-hydroxyphenyl)ethyl group, 1-(4-hydroxyphenyl)ethyl group, 1-(3-methoxyphenyl)ethyl group, 1-(4-methoxyphenyl)ethyl group, 1-(3,4-methylenedioxyphenyl)ethyl group, 1-(3,4,5-trimethoxyphenyl)ethyl group, 1-(3-isopropoxyphenyl)ethyl group, 1-(3-methanesulfonyloxyphenyl)ethyl group, 3-(dimethylcarbamoyl)cyclohexan-1-yl group, 2-methoxy-1-methylethyl group, 2-ethoxy-1-methylethyl group, 1-methyl-2-(2,2,2-trifluoroethoxy)ethyl group, 2-isopropoxy-1-methylethyl group, 3-methoxypropyl group, 3-methoxy-1-methylpropyl group, 3-ethoxy-1-methylpropyl group, 1-methyl-3-trifluoromethoxypropyl group, 4-methoxybutyl group, 4-methoxy-1-methylbutyl group, 4-ethoxy-1-methylbutyl group, 5-methoxypentyl group, 5-methoxy-1-methylpentyl group, 4-methoxy-1,4-dimethylpentyl group, 5-methoxy-1,5-dimethylhexyl group, 5-methoxy-1-methyl-2-pentenyl group, 1-methyl-3-(tetrahydropyran-4-yl)ethyl group, 1-methyl-2-(tetrahydropyran-4-yloxy)ethyl group, 1-methyl-2-(tetrahydropyran-4-ylmethoxy)ethyl group, 1-methyl-3-(2-methyl[1,3]dioxolan-2-yl)propyl group, 1-methyl-4-oxopentyl group, 4-hydroxy-1,4-dimethylpentyl group, 5-hydroxy-1,5-dimethylhexyl group, 3-[N-(tert-butoxycarbonyl)-N-methylamino]-1-methylpropyl group, 4-[N-acetyl-N-methylamino]-1-methylbutyl group, 4-[N-(tert-butoxycarbonyl)-N-methylamino]-1-methylbutyl group, tetrahydrofuran-2-ylmethyl group, 2-dimethylaminoethyl group, 2-diethylaminoethyl group, 3-dimethylaminopropyl group, morpholin-4-yl group, 1-ethoxycarbonylpiperidin-4-yl group, 1-benzylpiperidin-4-yl group, 2-morpholin-4-ylethyl group, 3-morpholin-4-ylpropyl group, pyridin-3-yl group, pyridin-4-yl group, pyridin-3-ylmethyl group, pyridin-4-ylmethyl group, 2-pyridin-2-ylethyl group, 2-pyridin-3-ylethyl group, 2-pyridin-4-ylethyl group, 3-imidazol-1-ylpropyl group, 1-tert-butoxycarbonylethyl group, 1-tert-butoxycarbonyl-2-methylpropyl group, 2-tert-butoxycarbonylethyl group, 1-dimethylaminocarbonylethyl group, 1-dimethylaminocarbonyl-2-methylpropyl group, 1-phenylcarbamoylethyl group, 1-methyl-2-phenylcarbamoylethyl group, 2-methyl-1-phenylcarbamoylpropyl group, 1-benzylcarbamoylethyl group, 1-(N-benzyl-N-methylcarbamoyl)ethyl group, 1-(tetrahydrofuran-2-ylmethyl)carbamoylethyl group, 1-(4-methylpiperazin-1-ylcarbonyl)ethyl group, 1-morpholin-4-ylcarbonylethyl group, 1-methyl-3-(morpholin-4-ylcarbonyl)propyl group, 1-methyl-4-(morpholin-4-ylcarbonyl)butyl group, 1-(2-piperidin-1-ylethylcarbamoyl)ethyl group, 1-(pyridin-3-ylmethylcarbamoyl)ethyl group, 1-(2-pyridin-2-ylethylcarbamoyl)ethyl group, or 1-[1-(methoxycarbonyl)ethylcarbamoyl]-2-ethylpropyl group.

Preferred examples of such R may include a methyl group, ethyl group, isopropyl group, 1,4-dimethylpentyl group, cyclohexyl group, 1,5-dimethylhexyl group, 4-hydroxycyclohexyl group, benzyl group, 1-phenylethyl group, 2-phenyl-1-methylethyl group, 3-phenyl-1-methylpropyl group, 1-(3-hydroxyphenyl)ethyl group, 1-(4-hydroxyphenyl)ethyl group, 1-(3-methoxyphenyl)ethyl group, 1-(4-methoxyphenyl)ethyl group, 1-(3,4-methylenedioxyphenyl)ethyl group, 1-(3,4,5-trimethoxyphenyl)ethyl group, 3-ethoxy-1-methylpropyl group, 4-methoxy-1-methylbutyl group, 4-methoxy-1,4-dimethylpentyl group, 5-methoxy-1,5-dimethylhexyl group, 5-methoxy-1-methyl-2-pentenyl group, 4-hydroxy-1,4-dimethylpentyl group, 5-hydroxy-1,5-dimethylhexyl group, 1-tert-butoxycarbonylethyl group, 1-tert-butoxycarbonyl-2-methylpropyl group, 2-tert-butoxycarbonylethyl group, 1-phenylcarbamoylethyl group, or 1-methyl-2-phenylcarbamoylethyl group. More preferred examples may include an isopropyl group, a 1,4-dimethylpentyl group, a 1,5-dimethylhexyl group, a 1-phenylethyl group, a 1-(3-hydroxyphenyl)ethyl group, a 1-(4-hydroxyphenyl)ethyl group, a 1-(3-methoxyphenyl)ethyl group, a 1-(4-methoxyphenyl)ethyl group, a 3-ethoxy-1-methylpropyl group, a 4-methoxy-1-methylbutyl group, a 5-methoxy-1-methyl-2-pentenyl group, a 4-hydroxy-1,4-dimethylpentyl group, and a 5-hydroxy-1,5-dimethylhexyl group.

When the [1,2,4]triazolo[1,5-a]pyrimidin-2-ylurea derivative represented by the general formula (1) of the present invention has an asymmetric carbon atom, the present invention includes all of an optically active body, a racemic body, and a mixture containing such an optically active body at any given ratio.

Specific examples of the [1,2,4]triazolo[1,5-a]pyrimidin-2-ylurea derivative represented by the general formula (1) of the present invention may include-compounds shown in the examples described below. Preferred compounds may include 1-isopropyl-3-[(7-thiophen-2-yl)-[1,2,4]triazolo[1,5-a]pyrimidin-2-yl]urea, 1-(3-ethoxy-1-methylpropyl)-3-[7-(3,4-methylenedioxyphenyl)-[1,2,4]-triazolo[1,5-a]pyrimidin-2-yl]urea, 1-(4-methoxy-1-methylbutyl)-3-[7-(4-methoxyphenyl)-[1,2,4]triazolo[1,5-a]pyrimidin-2-yl]urea, 1-(4-hydroxy-1,4-dimethylpentyl)-3-[7-(4-methoxyphenyl)-[1,2,4]triazolo[1,5-a]pyrimidin-2-yl]urea, 1-(5-hydroxy-1,5-dimethylhexyl)-3-[7-(4-methoxyphenyl)-[1,2,4]triazolo[1,5-a]pyrimidin-2-yl]urea, 1-(5-hydroxy-1,5-dimethylhexyl)-3-{7-[3-(pyridin-3-ylmethoxy)phenyl]-[1,2,4]triazolo[1,5-a]pyrimidin-2-yl}urea, 1-(5-hydroxy-1,5-dimethylhexyl)-3-[(7-thiophen-2-yl)-[1,2,4]triazolo[1,5-a]pyrimidin-2-yl]urea, 1-[1-(3-methoxyphenyl)ethyl]-3-[7-(4-methoxyphenyl)-[1,2,4]triazolo[1,5-a]pyrimidin-2-yl]urea, 1-[7-(3,4-methylenedioxyphenyl)-[1,2,4]triazolo[1,5-a]pyrimidin-2-yl]-3-[1-(3-methoxyphenyl)ethyl]urea, 1-[7-(3,4-methylenedioxyphenyl)-[1,2,4]triazolo[1,5-a]pyrimidin-2-yl]-3-[1-(3,4,5-trimethoxyphenyl)ethyl]urea,
1-(7-thiophen-2-yl[1,2,4]triazolo[1,5-a]pyrimidin-2-yl)-3-[1-(3,4,5-trimethoxyphenyl)ethyl]urea, or
1-[1-(3,4-methylenedioxyphenyl)ethyl]-3-{7-[3-(pyridin-3-ylmethoxy)phenyl]-[1,2,4]triazolo[1,5-a]pyrimidin-2-yl}urea.

Particularly preferred compounds may include
1-isopropyl-3-[(7-thiophen-2-yl)-[1,2,4]triazolo[1,5-a]pyrimidin-2-yl]urea,
(S)-1-(3-ethoxy-1-methylpropyl)-3-[7-(3,4-methylenedioxyphenyl)-[1,2,4]-triazolo[1,5-a]pyrimidin-2-yl]urea,
(S)-1-(4-methoxy-1-methylbutyl)-3-[7-(4-methoxyphenyl)-[1,2,4]triazolo[1,5-a]pyrimidin-2-yl]urea,
(S)-1-(4-hydroxy-1,4-dimethylpentyl)-3-[7-(4-methoxyphenyl)-[1,2,4]triazolo[1,5-a]pyrimidin-2-yl]urea,
(S)-1-(5-hydroxy-1,5-dimethylhexyl)-3-[7-(4-methoxyphenyl)-[1,2,4]triazolo[1,5-a]pyrimidin-2-yl]urea,
(S)-1-(5-hydroxy-1,5-dimethylhexyl)-3-{7-[3-(pyridin-3-ylmethoxy)phenyl]-[1,2,4]triazolo[1,5-a]pyrimidin-2-yl}urea,
(S)-1-(5-hydroxy-1,5-dimethylhexyl)-3-[(7-thiophen-2-yl)-[1,2,4]triazolo[1,5-a]pyrimidin-2-yl]urea,
(S)-1-[1-(3-methoxyphenyl)ethyl]-3-[7-(4-methoxyphenyl)-[1,2,4]triazolo[1,5-a]pyrimidin-2-yl]urea,
(S)-1-[7-(3,4-methylenedioxyphenyl)-[1,2,4]triazolo[1,5-a]pyrimidin-2-yl]-3-[1-(3-methoxyphenyl)ethyl]urea,
(S)-1-[7-(3,4-methylenedioxyphenyl)-[1,2,4]triazolo[1,5-a]pyrimidin-2-yl]-3-[1-(3,4,5-trimethoxyphenyl)ethyl]urea,
(S)-1-(7-thiophen-2-yl[1,2,4]triazolo[1,5-a]pyrimidin-2-yl)-3-[1-(3,4,5-trimethoxyphenyl)ethyl]urea, or
(S)-1-[1-(3,4-methylenedioxyphenyl)ethyl]-3-{7-[3-(pyridin-3-ylmethoxy)phenyl]-[1,2,4]triazolo[1,5-a]pyrimidin-2-yl}urea.

A pharmaceutically acceptable salt of the [1,2,4]triazolo[1,5-a]pyrimidin-2-ylurea derivative represented by the general formula (1) of the present invention can be obtained by common salt production reactions. Specific examples of such a salt may include: alkali metal salts (sodium salt, potassium salt, lithium salt, etc.); alkali-earth metal salts (calcium salt, magnesium salt, etc.); inorganic salts such as aluminum salt, iron salt, zinc salt, and ammonium salt; organic amine salts such as morpholine salt, ethylenediamine salt, guanidine salt,. diethylamine salt, triethylamine salt, dicyclohexylamine salt, procaine salt, diethanolamine salt, piperazine salt, and tetramethylammonium salt; hydrohalic acid salts (hydrofluoride, hydrochloride, hydrobromide, hydroiodide, etc.); inorganic acid salts such as nitrate, perchlorate, sulfate, and phosphate; sulfonates (methanesulfonate, trifluoromethanesulfonate, ethanesulfonate, benzenesulfonate, p-toluenesulfonate, etc.); organic acid salts such as acetate, malate, succinate, citrate, tartrate, oxalate, and maleate; and amino acid salts such as ornithinate, glutamate, and aspartate. Preferred examples may include hydrohalic acid salts and organic acid salts.

In addition, a compound (so-called prodrug), which is converted to the [1,2,4]triazolo[1,5-a]pyrimidin-2-ylamine derivative represented by the general formula (1) or a pharmaceutically acceptable salt thereof, as a result of being administered to a living body and undergoing metabolism or the like therein, under physiological conditions in such a living body, or under the physiological conditions described in "Iyakuhin no kaihatsu, Vol. 7, Bunshi sekkei," Hirokawa shoten, pp. 163-198 (1990), is also included in the present invention.

Moreover, when the [1,2,4]triazolo[1,5-a]pyrimidin-2-ylurea derivative represented by the general formula (1) of the present invention or a pharmaceutically acceptable salt thereof is a solvate such as a hydrate, such a solvate is also included in the present invention.

A method for producing the [1,2,4]triazolo[1,5-a]pyrimidin-2-ylurea derivative represented by the general formula (1) of the present invention is not particularly limited. The [1,2,4]triazolo[1,5-a]pyrimidin-2-ylurea derivative can be obtained by the methods represented by the following reaction formulas A to C, for example. The symbols Ar, X, and R used to indicate substituents in the compounds represented by the following reaction formulas have the same meanings as those described above.

[Formula 7]

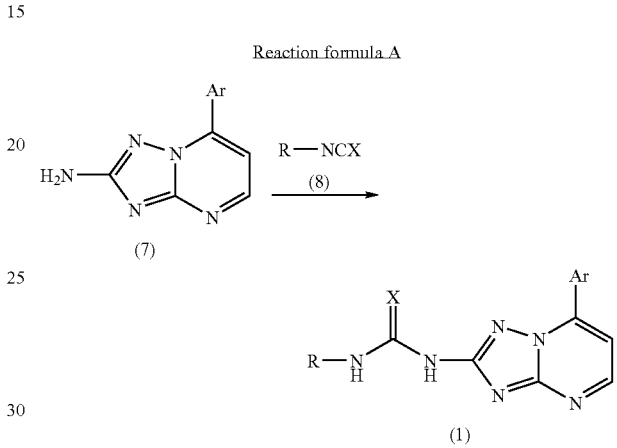

A compound (8) is allowed to reacted with a [1,2,4]triazolo[1,5-a]pyrimidin-2-amine derivative (7) to obtain a [1,2,4]triazolo[1,5-a]pyrimidin-2-ylurea derivative (1).

The present reaction is generally carried out in the presence or absence of a base. When the reaction is carried out in the presence of a base, examples of a base used may include: alkali metal carbonates such as lithium carbonate, sodium carbonate, or potassium carbonate; alkali metal bicarbonates such as lithium bicarbonate, sodium bicarbonate, or potassium bicarbonate; alkali metal hydrides such as lithium hydride, sodium hydride, or potassium hydride; alkali metal hydroxides such as lithium hydroxide, sodium hydroxide, or potassium hydroxide; alkali metal alkoxides such as lithium methoxide, sodium methoxide, sodium ethoxide, or potassium tert-butoxide; alkyl metals such as butyl lithium or tert-butyl magnesium chloride; metal amides such as lithium diisopropylamide (LDA), lithium bis(trimethylsilyl)amide, or sodium bis(trimethylsilyl)amide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO), or 1,8-diazabicyclo[5.4.0]-7-undecene (DBU). Preferred examples may include alkali metal hydrides and metal amides. Such a base is used at a molar equivalent ratio between 0.5:1 and 5:1, and preferably between 1:1 and 2:1, with respect to the compound (7). The compound (8) is used at a molar equivalent ratio between 0.5:1 and 5:1, and preferably 1:1 and 2:1, with respect to the compound (7).

The present reaction is carried out in the presence or absence of a solvent. The type of a solvent used herein is not particularly limited, as long as it does not affect the reaction. Examples of such a solvent may include: aliphatic hydrocarbons such as hexane, heptane, ligroin, or petroleum ether;

aromatic hydrocarbons such as benzene, toluene, or xylene; halogenated hydrocarbons such as methylene chloride, chloroform, or 1,2-dichloroethane; ethers such as diethyl ether, diisopropyl ether, tetrahydrofuran, dixane, dimethoxyethane, or diethylene glycol dimethyl ether; nitriles such as acetonitrile or propionitrile; amides such as dimethylformamide, dimethylacetamide, or hexamethylphosphoric triamide; ureas such as N,N-dimethylimidazolidinone; and a mixed solvent consisting of the aforementioned solvents. Preferred examples of such a solvent may include ethers and ureas. The reaction temperature is generally between −80° C. and 150° C., and preferably between −10° C. and 50° C. The reaction time is generally between 10 minutes and 48 hours. Examples of the compound (8) may include: isocyanic esters such as methyl isocyanate, ethyl isocyanate, isopropyl isocyanate, cyclohexyl isocyanate, or phenyl isocyanate; and isothiocyanic esters such as methyl isothiocyanate or ethyl isothiocyanate. A commercially available compound may be used as the compound (8). Otherwise, the compound (8) may be produced by known methods or methods equivalent thereto.

[Formula 8]

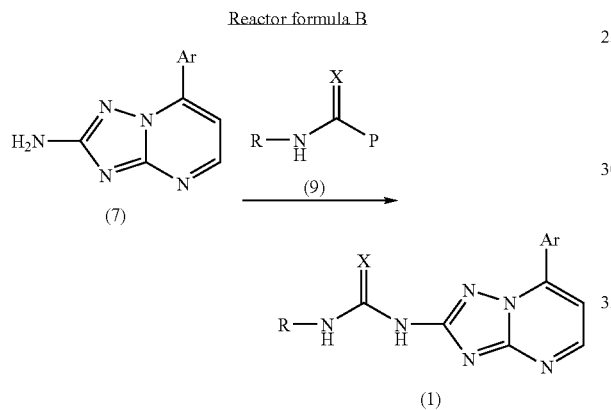

[wherein P represents a leaving group (for example, a halogeno group, a phenoxy group, a 4-nitrophenoxy group, a phenylsulfanyl group, a pyridin-2-ylsulfanyl group, etc.)].

A compound (9) is allowed to reacted with the [1,2,4]triazolo[1,5-a]pyrimidin-2-amine derivative (7) to obtain the [1,2,4]triazolo[1,5-a]pyrimidin-2-ylurea derivative (1).

The present reaction is generally carried out in the presence or absence of a base. When the reaction is carried out in the presence of a base, examples of a base used are the same as those used in the aforementioned reaction A. Preferred examples of such a base are also the same as those used in the aforementioned reaction A. Such a base is used at a molar equivalent ratio between 0.5:1 and 5:1, and preferably between 1:1 and 2:1, with respect to the compound (7). The compound (9) is used at a molar equivalent ratio between 0.5:1 and 5:1, and preferably 1:1 and 2:1, with respect to the compound (7). The present reaction is carried out in the presence or absence of a solvent. When the reaction is carried out in the presence of a solvent, examples of a solvent used are the same as those used in the aforementioned reaction A. Preferred examples of such a solvent are also the same as those used in the aforementioned reaction A. The reaction temperature is generally between −80° C. and 150° C., and preferably between −10° C. and 50° C. The reaction time is generally between 10 minutes and 48 hours. Examples of the compound (9) may include: N-isobutyl carbamoyl chloride, N-benzyl carbamoyl chloride, 4-nitrophenyl (1-phenylethyl) carbamate, N-cyano-N'-isopropyl-O-phenylisourea, N-cyano-N'-(1,5-dimethylhexyl)-O-phenylisourea, N-cyano-N'-(1-phenylethyl)-O-phenylisourea, N-methyl-S-phenylisothiourea, and N,N'-dimethyl-S-phenylisothiourea. A commercially available compound may be used as the compound (9). Otherwise, the compound (9) may be produced by known methods or methods equivalent thereto.

[Formula 9]

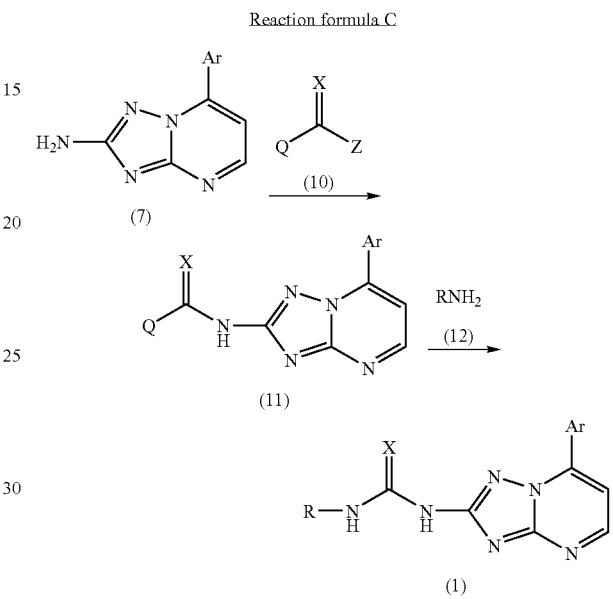

[wherein Q represents the same leaving group as P in the aforementioned reaction formula B, and Z represents a halogeno group].

A compound (10) is allowed to reacted with the [1,2,4]triazolo[1,5-a]pyrimidin-2-ylamine derivative (7) to obtain a compound (11). Subsequently, an amine compound (12) is allowed to reacted with the compound (11) to obtain the [1,2,4]triazolo[1,5-a]pyrimidin-2-ylurea derivative (1). The reaction of obtaining the compound (11) is generally carried out in the presence or absence of a base. When the reaction is carried out in the presence of a base, examples of a base used are the same as those used in the aforementioned reaction A. Preferred examples of such a base may include alkali metal carbonates, alkali metal bicarbonates, and organic amines. Such a base is used at a molar equivalent ratio between 1:1 and an excessive amount (solvent amount), and preferably between 1:1 and 5:1, with respect to the compound (7). The compound (10) is used at a molar equivalent ratio between 0.5:1 and 5:1, and preferably between 1:1 and 2:1, with respect to the compound (7). The present reaction is carried out in the presence or absence of a solvent. When the reaction is carried out in the presence of a solvent, examples of a solvent used are the same as those used in the aforementioned reaction A. Preferred examples of such a solvent are also the same as those used in the aforementioned reaction A. The reaction temperature is generally between −50° C. and 100° C., and preferably between −10° C. and a room temperature. The reaction time is generally between 10 minutes and 24 hours. The obtained compound (11) may be directly used as a reaction solution, or it may be used as a crude product for the following reaction. Otherwise, it may also be isolated from the reaction mixture according to common methods. Examples of the compound (10) may include trichloromethyl chloroformate, phenyl chloroformate, 4-nitrophenyl chloroformate, and pentafluorophenyl chloroformate. A commercially available compound may be used as the compound (10), or it may also be produced by known methods or methods equivalent thereto.

The amine compound (12) is used in the reaction at a molar equivalent ratio between 0.5:1 and 5:1, and preferably between 1:1 and 3:1, with respect to the compound (11). The present reaction is carried out in the presence or absence of a solvent. When the reaction is carried out in the presence of a solvent, examples of a solvent used are the same as those used in the aforementioned reaction A. Preferred examples of such a solvent may include ethers, amides, and ureas. The reaction temperature is generally between −50° C. and 100° C., and preferably between −10° C. and a room temperature. The reaction time is generally between 10 minutes and 24 hours. A commercially available compound may be used as the compound (12), or it may also be produced by known methods or methods equivalent thereto.

A stereoisomer of the [1,2,4]triazolo[1,5-a]pyrimidin-2-ylurea derivative (1) may be stereospecifically produced using a raw material compound having a desired configuration, or it may also be produced by dividing a mixture of stereoisomers by a general fractionation or separation method.

The [1,2,4]triazolo[1,5-a]pyrimidin-2-ylamine derivative (7) can also be produced by the method described in the following reaction formula (D).

[Formula 10]

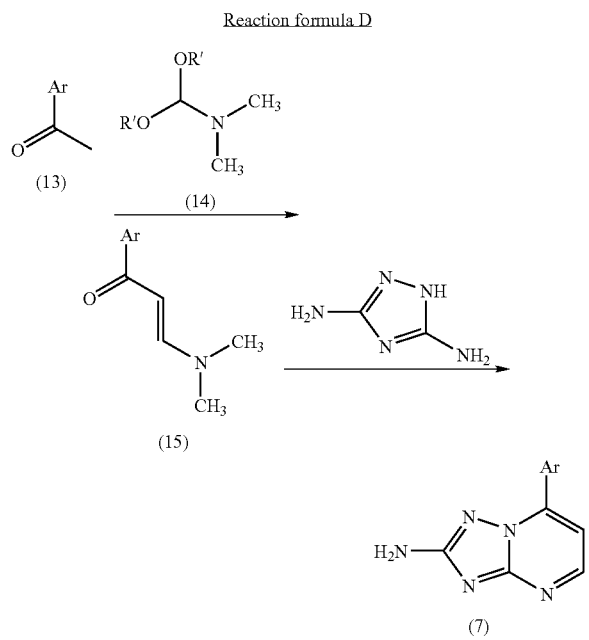

[wherein R' represents a (C1-C6)alkyl group, and Ar has the same meanings as described above].

A compound (13) and a dimethylformamide dialkyl acetal (14) are condensed according to the method described in Chemische Berichte, 1971, vol. 104, pp. 348-349, for example to obtain an α,β-unsaturated ketone derivative (15). The compound (14) is used at a molar equivalent ratio between 0.5:1 and 5:1, and preferably between 1:1 and 3:1, with respect to the compound (13). The present reaction is carried out in the presence or absence of a solvent. When the reaction is carried out in the presence of a solvent, examples of a solvent used are the same as those used in the aforementioned reaction A. The reaction temperature is generally between 80° C. and 200° C., and preferably between 100° C. and 150° C. The reaction time is generally between 6 and 48 hours. Commercially available compounds may be used as the compounds (13) and (14), or these compounds may also be produced by known methods or methods equivalent thereto.

Subsequently, the compound (15) and a 3,5-diamino-1,2,4-triazole are condensed to obtain the [1,2,4]triazolo[1,5-a]pyrimidin-2-ylamine derivative (7). The present reaction is generally carried out in the presence of an acid. Examples of such an acid may include: mineral acids such as hydrochloric acid or sulfuric acid; carboxylic acids such as acetic acid, trifluoroacetic acid, or benzoic acid; sulfonic acids such as methanesulfonic acid, trifluoromethanesulfonic acid, p-toluenesulfonic acid, or camphorsulfonic acid; and Lewis acids such as boron trifluoride, titanium tetrachloride, or tin tetrachloride. Of these, Lewis acids are preferable. Such an acid is used at a molar equivalent ratio between 0.1:1 and an excessive amount, and preferably between 0.2:1 and 2:1, with respect to the compound (15). The 3,5-diamino-1,2,4-triazole is used at a molar equivalent ratio between 0.5:1 and 10:1, and preferably between 1:1 and 4:1, with respect to the compound (15). The present reaction is carried out in the presence of a solvent. The type of such a solvent is not particularly limited, as long as the reaction progresses in the presence of the solvent. Examples of such a solvent may include: aliphatic hydrocarbons such as hexane, heptane, ligroin, or petroleum ether; aromatic hydrocarbons such as benzene, toluene, or xylene; halogenated hydrocarbons such as methylene chloride, chloroform, or 1,2-dichloroethane; ethers such as diethyl ether, diisopropyl ether, tetrahydrofuran, dixane, dimethoxyethane, or diethylene glycol dimethyl ether; nitriles such as acetonitrile or propionitrile; amides such as dimethylformamide, dimethylacetamide, or hexamethylphosphoric triamide; ureas such as N,N-dimethylimidazolidinone; carboxylic acids such as acetic acid or propionic acid; and a mixed solvent consisting of the aforementioned solvents. Of these, aromatic hydrocarbons are preferable.

The reaction temperature is generally between 50° C. and 150° C., and preferably between 80° C. and 120° C. The reaction time is generally between 10 minutes and 6 hours.

When a substituent of Ar in the compound (1) is a (C1-C6) alkoxyl group, which may have a substituent, for example, such a compound can be produced by applying a common alkylation reaction or a condensation reaction such as Mitsunobu reaction to a compound wherein the substituent of Ar is a hydroxyl group. That is to say, a substituent is converted by a common organic reaction to produce a [1,2,4]triazolo[1,5-a]pyrimidin-2-ylamine derivative represented by the general formula (1).

When an amino group, a hydroxyl group, a carboxyl group, or the like is contained in the substituent in each of the aforementioned reactions, such a group is protected by known methods (for example, the method described in Greene, T. W. et al., "PROTECTIVE GRPOUS IN ORGANIC SYNTHESIS," 2$^{nd}$ edition, WILEY INTERSCIENCE (U.S.A.)). The protected compound may be used as a raw material, and after completion of the reaction, the protecting group may be eliminated to produce a compound of interest. Examples of a protecting group for an amino group may include a formyl group, an acetyl group, a benzoyl group, a methoxycarbonyl group, an ethoxycarbonyl group, a tert-butoxycarbonyl group, a benzyloxycarbonyl group, and a phthaloyl group. Examples of a protecting group for a hydroxyl group may include a methyl group, an ethyl group, a benzyl group, a formyl group, an acetyl group, a benzoyl group, a tert-butyldimethylsilyl group, and a tert-butyldiphenylsilyl group. Examples of a protecting group for a carboxyl group may include a methyl group, an ethyl group, a tert-butyl group, and a benzyl group. These groups are used as protecting groups, as necessary.

When a product is obtained in the form of a free body, it can be converted to a salt according to common methods. When a product is obtained in the form of a salt, it can be converted to a free body according to common methods.

Each of the aforementioned products can be isolated and purified by known separation means such as distillation, vacuum concentration, solvent extraction, crystallization, or chromatography.

The present invention includes a pharmaceutical comprising, as an active ingredient, the [1,2,4]triazolo[1,5-a]pyrimidin-2-ylurea derivative represented by the general formula (1) or a pharmaceutically acceptable salt thereof.

Moreover, the [1,2,4]triazolo[1,5-a]pyrimidin-2-ylurea derivative represented by the general formula (1) of the present invention or a pharmaceutically acceptable salt thereof has antigen presentation inhibiting activity, as described in the test examples below. The present invention also includes an antigen presentation inhibitor, which comprises, as an active ingredient, the above described derivative or a pharmaceutically acceptable salt thereof.

The present invention also includes an immunosuppressive agent, which comprises, as an active ingredient, the [1,2,4]triazolo[1,5-a]pyrimidin-2-ylurea derivative represented by the general formula (1) or a pharmaceutically acceptable salt thereof.

The present invention further includes a lymphocyte proliferation inhibitor, an inhibitor for cell growth and maturation, and an immune tolerance inducer, which comprise, as an active ingredient, the [1,2,4]triazolo[1,5-a]pyrimidin-2-ylurea derivative represented by the general formula (1) or a pharmaceutically acceptable salt thereof. Furthermore, the present invention also includes a therapeutic or preventive agent for graft rejection reaction or graft versus host reaction, a therapeutic or preventive agent for autoimmune disease, a therapeutic or preventive agent for allergic disease, a therapeutic or preventive agent for inflammatory disease, and anticancer drug, all of which comprise, as an active ingredient, the above described derivative or a pharmaceutically acceptable salt thereof.

The antigen presentation-inhibiting substance of the present invention can be used for treating and preventing acute rejection, graft versus host reaction, or chronic rejection occurring after transplantation, for inducing immune tolerance, and the like. As an organ to be transplanted, any types of organs such as the bone marrow, kidney, liver, heart, or pancreas can be used. As a relationship between a donor and a host, any types of relationships such as xenogeneic transplantation, allogeneic transplantation, or transplantation involving blood incompatibility are available. The antigen presentation-inhibiting substance of the present invention can be used for the purpose of immunosuppression or the long-term survival of an organ transplanted, with regard to the treatment of cancers, the treatment of autoimmune diseases, gene therapy, and organ transplantation used in regenerative medicine or the like, such as transplantation of bone marrow, peripheral blood stem cell, or cord-blood stem cells.

The therapeutic or preventive agent for autoimmune diseases specifically means an agent for treating or preventing rheumatoid arthritis, multiple sclerosis, systemic lupus erythematosus, discoid lupus erythematosus, Sjogren's syndrome, Crohn's disease, ulcerative colitis, idiopathic thrombocythemia, aplastic anemia, autoimmune hepatitis, insulin dependent diabetes mellitus, myasthenia gravis, polymyositis, scleroderma, mixed connective tissue disease, ankylosing spondylitis, and chronic thyroiditis.

The therapeutic or preventive agent for allergic diseases specifically means an agent for treating or preventing atopic dermatitis, pollinosis, contact hypersensitivity, asthma, psoriasis, and anaphylaxis.

The therapeutic or preventive agent for inflammatory diseases specifically means an agent for treating or preventing Behcet's disease, polyarteritis, sarcoidosis, glomerulonephritis, nephrotic syndrome, refractory angiitis, and Wegener's syndrome.

The anticancer drug specifically means an agent for treating or preventing malignant tumors such as lymphoma, leukemia, encephaloma, lung cancer, pancreatic cancer, stomach cancer, and colon cancer.

The pharmaceutical of the present invention is produced by using singly a [1,2,4]triazolo[1,5-a]pyrimidin-2-ylurea derivative or pharmaceutically acceptable salt thereof or by mixing such a derivative or a salt thereof with an excipient or carrier, and then formulating the obtained product into a preparation such as a suspension, an emulsion, an injection, an inhalant, a tablet, a pill, a granule, a parvule, a powder, a capsule, a liquid for oral use, a suppository, a liquid for percutaneous use, an adhesive preparation for percutaneous use, an ointment, a liquid for transmucosal use, or an adhesive preparation for transmucosal use. The thus produced preparation can be administered via an oral or parenteral administration route. As additives such as an excipient or carrier, pharmaceutically acceptable products are selected. The type and composition of such an additive depend on the administration route or the administration method. In the case of an injection for example, common salts and sugars such as glucose or mannitol are generally preferable. In the case of an oral agent, starch, lactose, crystalline cellulose, magnesium stearate, and the like, are preferable. Generally used additives such as an auxiliary agent, a stabilizer, a wetting agent, an emulsifier, or a buffer solution may be added to the aforementioned pharmaceutical, as desired.

The content of the present compound in such a pharmaceutical differs depending on the type of the pharmaceutical. The content of the compound is generally between approximately 1% and 100% by weight, and preferably between approximately 10% and 90% by weight, based on the total weight of the pharmaceutical. In the case of an oral agent, the pharmaceutical, together with the aforementioned additives, is administered specifically in the form of a tablet, a capsule, a powder, a granule, a liquid, a dry syrup, etc. Such a capsule, a tablet, a granule, or a powder contains an active ingredient at a weight ratio generally between 5% and 100% by weight, and preferably between 25% and 98% by weight.

The pharmaceutical of the present invention may be administered by any administration methods such as oral administration, injection, intrarectal administration, intraportal administration, perfusion to organs, or local administration to organs. The dose of the pharmaceutical of the present invention is different depending on an administration method, applicable disease, the pathological conditions, age, body weight of a patient, or the like. The pharmaceutical of the present invention may be administered at a dose of generally between 0.01 mg and 500 mg/kg, and preferably between 0.05 mg and 50 mg/kg, once or divided into several administrations per day. The pharmaceutical of the present invention may be administered for 1 day or consecutive days. It may also be administered repeatedly with intervals of several days or several months. An administration method, a dose, and a administration schedule other than the aforementioned conditions may also be used, as necessary.

The present invention will be described more in detail in the following examples, reference examples, and test examples. However, these examples are not intended to limit the scope of the present invention.

REFERENCE EXAMPLE 1

Synthesis of 7-thiophen-2-yl[1,2,4]triazolo[1,5-a]pyrimidin-2-ylamine

A commercially available 2-acetylthiophene (8.20 g) and a commercially available N,N-dimethylformamide diethylacetal (13.6 ml) were heated to reflux in xylene (13 ml) at 130° C. for 2 days. The reaction solution was concentrated under a reduced pressure and then subjected to an azeotropic treatment with toluene. Thereafter, the resultant was crystallized in a toluene-hexane mixed solvent to obtain 3-dimethylamino-1-thiophen-2-ylpropenone (11.52 g).
$^1$H-NMR (CDCl$_3$): 2.80-3.30 (6H, m), 5.63 (1H, d, J=12.4), 7.08 (1H, dd, J=3.7, 5.0), 7.43 (1H, dd, J=1.1, 5.0), 7.63 (1H, dd, J=1.1, 3.7), 7.79 (1H, d, J=12.4)

The obtained 3-dimethylamino-1-thiophen-2-ylpropenone (10.78 g) was dissolved in toluene (160 ml). Thereafter, 3,5-diamino-1,2,4-triazole (14.15 g) was added to the solution, and the obtained mixture was stirred at 100° C. After 10-camphorsulfonic acid (13.82 g) was added thereto, the mixture was heated to reflux for 1.5 hours. The reaction solution was cooled to a room temperature, and the supernatant was then eliminated (decant). The residue was washed by successive suspension in an aqueous 5% sodium carbonate-10% ethanol solution, a 10% ethanol solution, ethanol, and methylene chloride. The resultant was then dried under a reduced pressure to obtain the captioned compound (8.55 g).

REFERENCE EXAMPLE 2

Synthesis of 7-(4-benzyloxyphenyl)-[1,2,4]triazolo[1,5-a]pyrimidin-2-ylamine

The captioned compound was obtained using 4'-benzyloxyacetophenone, instead of using the 2-acetylthiophene used in Reference Example 1.

REFERENCE EXAMPLE 3

Synthesis of 7-(4-hydroxyphenyl)-[1,2,4]triazolo[1,5-a]pyrimidin-2-ylamine

Acetic acid (40 ml) and concentrated hydrochloric acid (40 ml) were added to 7-(4-benzyloxyphenyl)-[1,2,4]triazolo[1,5-a]pyrimidin-2-ylamine (the compound obtained in Reference Example 2; 5.70 g), and the obtained mixture was stirred at 80° C. for 3 hours. The resultant product was concentrated under a reduced pressure, and the residue was then washed by suspension in acetone (200 ml) and then in a 50% ethanol solution (100 ml) to obtain the captioned compound (2.60 g).

REFERENCE EXAMPLE 4

Synthesis of 7-[4-(tetrahydropyran-4-ylmethoxy)phenyl]-[1,2,4]triazolo[1,5-a]pyrimidin-2-ylamine 7-(4-hydroxyphenyl)-[1,2,4]triazolo[1,5-a]pyrimidin-2-ylamine (the compound obtained in Reference Example 3; 295 mg) was dissolved in N,N-dimethylformamide (8 ml). Thereafter, tetrahydropyran-4-ylmethyl p-toluenesulfonate (460 mg) and cesium carbonate (556 mg) were added to the obtained solution, and the obtained mixture was stirred at 90° C. overnight. After the reaction solution was cooled to a room temperature, distilled water (18 ml) was added thereto. The generated precipitate was collected by filtration, and the obtained product was then washed by successive suspension in a 20% ethanol solution, ethanol, and acetone to obtain the captioned compound (310 mg).

REFERENCE EXAMPLE 5

Synthesis of 7-(4-nitrophenyl)-[1,2,4]triazolo[1,5-a]pyrimidin-2-ylamine

The captioned compound was obtained using 4'-nitroacetophenone, instead of using the 2-acetylthiophene used in Reference Example 1.

REFERENCE EXAMPLE 6

Synthesis of 7-(4-aminophenyl)-[1,2,4]triazolo[1,5-a]pyrimidin-2-ylamine 7-(4-nitrophenyl)-[1,2,4]triazolo[1,5-a]pyrimidin-2-ylamine (the compound obtained in Reference Example 5; 62.0 mg) was suspended in acetic acid (0.8 ml). Thereafter, tin (II) chloride dihydrate (200 mg) and concentrated hydrochloric acid (0.6 ml) were added to the suspension, and the obtained mixture was stirred at a room temperature overnight. The reaction solution was neutralized with a 6 M aqueous sodium hydroxide solution, and the generated precipitate was collected by filtration. The obtained product was washed by successive suspension in distilled water, ethanol, and methylene chloride to obtain the captioned compound (42.3 mg).

REFERENCE EXAMPLE 7

Synthesis of 7-(4-acetylaminophenyl)-[1,2,4]triazolo[1,5-a]pyrimidin-2-ylamine 7-(4-aminophenyl)-[1,2,4]triazolo[1,5-a]pyrimidin-2-ylamine (the compound obtained in Reference Example 6; 20.1 mg) was suspended in methanol (2 ml), and thereafter, acetic anhydride (16.9 µl) was added thereto, followed by stirring the mixture over a day and a night. Thereafter, an aqueous 5% potassium carbonate solution (5 ml) was added to the reaction solution, and the mixture was then centrifuged (2,000 rpm, 10 minutes). Thereafter, the supernatant was discarded, and the precipitate was then washed by suspension in ethanol and in methylene chloride to obtain the captioned compound (19.2 mg).

REFERENCE EXAMPLES 8 TO 22

Hereafter, using commercially available compounds or compounds obtained according to known methods or methods equivalent thereto, the compounds of Reference Examples 8 to 19 shown in Table 1 were produced by the same method as that described in aforementioned Reference Example 1. The compound of Reference Example 20 was produced by the same method as that described in aforementioned Reference Example 3. The compounds of Reference Examples 21 and 22 were produced by the same method as that described in aforementioned Reference Example 4. The structural formulas and physicochemical data of the compounds of Reference Examples 1 to 22 are shown in Table 1.

TABLE 1
Structural formula
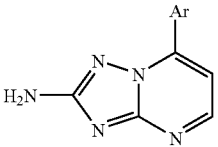
| Reference Example No. | Ar | Physicochemical data |
|---|---|---|
| Reference Example 1 | 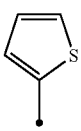 | MS: m/z 218 (M + H)+. |
| Reference Example 2 | 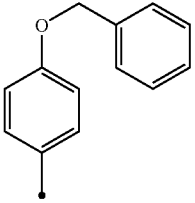 | MS: m/z 318 (M + H)+. |
| Reference Example 3 | 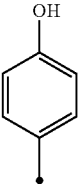 | $^1$H-NMR (DMSO-d6, ppm): 6.46 (2H, brs), 7.01 (1H, m), 7.19 (1H, d, J = 4.9 Hz). 7.39 (1H, dd, J = 7.8, 8.0 Hz), 7.48-7.60 (2H, overlapped), 8.52 (1H, d, J = 4.8 Hz): MS: m/z 228 (M + H)+. |
| Reference Example 4 | 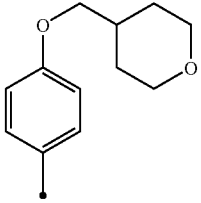 | MS: m/z 326 (M + H)+. |
| Reference Example 5 | 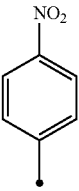 | $^1$H-NMR (DMSO-d6, ppm): 6.57 (2H, brs), 7.36 (1H, d, J = 4.9 Hz), 8.30-8.60 (4H, overlapped), 8.61 (1H, d, J = 4.9 Hz). |
| Reference Example 6 | 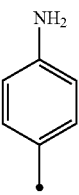 | MS: m/z 227 (M + H)+. |

TABLE 1-continued

Structural formula:

Ar on top position, Ar on bottom position of 2-amino-[1,2,4]triazolo[1,5-a]pyrimidine core (H₂N-group attached)

| Reference Example No. | Ar | Physicochemical data |
|---|---|---|
| Reference Example 7 | 4-(NHC(O)CH₃)-phenyl | MS: m/z 269 (M + H)⁺. |
| Reference Example 8 | 4-OCH₃-phenyl | ¹H-NMR (DMSO-d6, ppm): 3.87 (3H, s), 6.45 (2H, brs), 7.10-7.22 (2H, m), 7.26 (1H, d, J = 5.1 Hz), 8.20-8.32 (2H, m), 8.49 (1H, d, J = 4.6 Hz); MS: m/z 242 (M + H)⁺. |
| Reference Example 9 | 4-pyridyl | MS: m/z 213 (M + H)⁺. |
| Reference Example 10 | 3-Cl-phenyl | MS m/z 246 (M + H)⁺. |
| Reference Example 11 | phenyl | MS: m/z 212 (M + H)⁺. |
| Reference Example 12 | 2,4-di-OCH₃-phenyl | ¹H-NMR (DMSO-d6, ppm): 3.78 (3H, s), 3.86 (3H, s), 6.33 (2H, brs), 6.69 (1H, dd, J = 2.4, 8.5 Hz), 6.76 (1H, d, J = 2.4 Hz), 7.00 (1H, d, J = 4.8 Hz), 7.57 (1H, d, J = 8.5 Hz), 8.45 (1H, d, J = 4.8 Hz). |
| Reference Example 13 | 3,4-di-OCH₃-phenyl | ¹H-NMR (DMSO-d6, ppm): 3.87 (6H, s), 6.43 (2H, brs), 7.17 (1H, d, J = 8.5 Hz), 7.32 (1H, d, J = 5.1 Hz), 7.85 (1H, d, J = 2.1 Hz), 7.95 (1H, dd, J = 2.1, 8.5 Hz), 8.49 (1H, d, J = 4.9 Hz). |

TABLE 1-continued

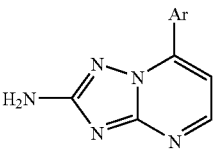

| Reference Example No. | Structural formula | Physicochemical data |
|---|---|---|
| Reference Example 14 |  | ¹H-NMR (DMSO-d6, ppm): 3.85 (3H, s), 6.48 (2H, brs), 7.19 (1H, m), 7.29 (1H, d, J = 5.0 Hz), 7.52 (1H, dd, J = 7.7, 8.4 Hz), 7.68-7.80 (2H, overlapped), 8.54 (1H, d, J = 4.8 Hz). |
| Reference Example 15 | 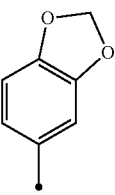 | MS: m/z 256 (M + H)⁺. |
| Reference Example 16 |  | ¹H-NMR (DMSO-d6, ppm): 1.32 (6H, d, J = 6.0 Hz), 4.79 (1H, sept, J = 6.0 Hz), 6.45 (2H, brs), 7.13 (2H, m), 7.26 (1H, d, J = 5.0 Hz), 8.24 (2H, m), 8.45 (1H, d, J = 5.0 Hz). |
| Reference Example 17 | 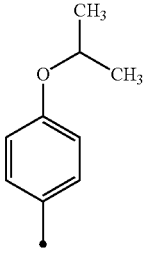 | ¹H-NMR (DMSO-d6, ppm): 3.20-3.37 (2H, overlapped), 4.66 (2H, t, J = 8.7 Hz), 6.97 (2H, brs), 6.98 (1H, d, J = 8.5 Hz), 7.22 (1H, d, J = 5.0 Hz), 8.09 (1H, dd, J = 1.8 and 8.5 Hz), 8.18 (1H, m), 8.47 (1H, d, J = 5.1 Hz). |
| Reference Example 18 |  | MS: m/z 302 (M + H)⁺. |
| Reference Example 19 | 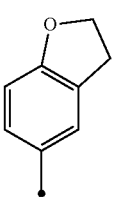 | MS: m/z 318 (M + H)⁺. |

TABLE 1-continued

Structural formula

H₂N-[triazolo[1,5-a]pyrimidine core with Ar at 7-position]

| Reference Example No. | Ar | Physicochemical data |
|---|---|---|
| Reference Example 20 | 3-hydroxyphenyl (OH) | MS: m/z 228 (M + H)$^+$. |
| Reference Example 21 | 4-(2-methoxyethoxy)phenyl (OCH₃) | MS: m/z 286 (M + H)$^+$. |
| Reference Example 22 | 3-(pyridin-3-ylmethoxy)phenyl | MS: m/z 319 (M + H)$^+$. |

EXAMPLE 001

Synthesis of 1-phenyl-3-[(7-thiophen-2-yl)-[1,2,4]triazolo[1,5-a]pyrimidin-2-yl]urea (Production Method Example of Reaction Formula A)

7-thiophen-2-yl[1,2,4]triazolo[1,5-a]pyrimidin-2-ylamine (the compound obtained in Reference Example 1; 217 mg) was suspended in tetrahydrofuran (12 ml). Thereafter, hexamethyldisilane lithium salts (1 M tetrahydrofuran solution, 2 ml) was added to the suspension, and the obtained mixture was stirred at a room temperature for 5 minutes. Thereafter, phenyl isocyanate (109 μl) was added to the reaction solution, and the obtained mixture was then stirred for 20 minutes. Thereafter, N,N-dimethylethylenediamine (200 μl) was added thereto, and the obtained mixture was stirred for 20 minutes. Thereafter, the reaction solution was diluted with methylene chloride (20 ml), and the methylene chloride solution was washed with 4 M hydrochloric acid (10 ml×3) and an aqueous 5% potassium carbonate solution (12 ml). The resultant product was dried over anhydrous sodium sulfate, and the solvent was then distilled off under a reduced pressure. The residue was washed by suspension in methanol and in methylene chloride to obtain the captioned compound (92 mg).

EXAMPLE 029

Synthesis of 1-isopropyl-3-(7-thiophen-2-yl[1,2,4]triazolo[1,5-a]pyrimidin-2-yl)urea (Production Method Example of Reaction Formula A)

7-thiophen-2-yl[1,2,4]triazolo[1,5-a]pyrimidin-2-ylamine (the compound obtained in Reference Example 1; 9.73 g) was suspended in tetrahydrofuran (400 ml). Thereafter, hexamethyldisilane lithium salts (1.73 M tetrahydrofuran solution, 51.8 ml) was added to the suspension, and the obtained mixture was stirred at a room temperature for 10 minutes. Thereafter, isopropyl isocyanate (7.04 ml) was added to the reaction solution, and the obtained mixture was then stirred for 30 minutes. Thereafter, N,N-dimethylethylenediamine (10 ml) was added thereto, and the obtained mixture was stirred for 15 minutes. Thereafter, the reaction solution was diluted with methylene chloride (500 ml), and the diluted solution was then successively washed with 2 M hydrochloric acid (600 ml×2), an aqueous 5% potassium carbonate solution (600 ml), and a saturated saline solution (500 ml). The resultant product was dried over anhydrous sodium sulfate, and the solvent was then distilled off under a reduced pressure. The residue was purified by silica gel column chromatography (3.6 Φ×25 cm; eluted with a 0% to 2% methanol-containing methylene chloride solution), and the resultant product was then crystallized from ethyl acetate to obtain the captioned compound (8.40 g).

EXAMPLE 040

Synthesis of 1-[7-(4-methoxyphenyl)-[1,2,4]triazolo[1,5-a]pyrimidin-2-yl]-3-(tetrahydrofuran-2-ylmethyl)urea (Production Method Example of Reaction Formula A)

A compound, di-tert-butyl dicarbonate (210 mg), was dissolved in methylene chloride (2 ml). Thereafter, 4-dimethylaminopyridine (117 mg) and tetrahydrofurfurylamine (99.1 µl) were added to the solution, and the obtained mixture was stirred for 10 minutes to generate a tetrahydrofurfuryl isocyanate solution. 7-(4-methoxyphenyl)-[1,2,4]triazolo[1,5-a]pyrimidin-2-ylamine (the compound obtained in Reference Example 8; 145 mg) was suspended in tetrahydrofuran (4 ml), and thereafter, hexamethyldisilane lithium salts (1.2 M tetrahydrofuran solution, 1.0 ml) was added thereto, followed by stirring the mixture. Thereafter, the aforementioned tetrahydrofurfuryl isocyanate solution was added to the reaction solution, and the mixture was then stirred for 10 minutes. Thereafter, N,N-dimethylethylenediamine (120 µl) was added thereto, and the obtained mixture was further stirred for 10 minutes. Thereafter, the reaction solution was diluted with methylene chloride (6 ml). The diluted solution was washed with 4 M hydrochloric acid and an aqueous 5% potassium carbonate solution, and the organic layer was concentrated under a reduced pressure. The residue was purified by gel filtration column chromatography (Sephadex LH-20; 2.1 Φ×110 cm; eluted with methanol) to obtain the captioned compound (59 mg).

EXAMPLE 241

Synthesis of (S)—N-cyano-N'-[1-(4-methoxyphenyl)ethyl]-N"-[7-(4-methoxyphenyl)-[1,2,4]triazolo[1,5-a]pyrimidin-2-yl]guanidine (Production Method Example of Reaction Formula B)

(S)-(-)-1-(4-methoxyphenyl)ethylamine (321 mg) was dissolved in isopropanol (6 ml). Thereafter, diphenyl N-cyanocarbonimidate (508 mg) was added to the solution, and the obtained mixture was stirred at a room temperature for 2 hours. The precipitated crystals were collected by filtration, and the collected crystals were then washed with isopropyl ether to obtain (S)-1-cyano-3-[1-(4-methoxyphenyl)ethyl]-2-phenyl isourea (339 mg).

ESI-MS (positive mode): m/z 296 (M+H)$^+$ 7-(4-methoxyphenyl)-[1,2,4]triazolo[1,5-a]pyrimidin-2-ylamine (the compound obtained in Reference Example 8; 96.5 mg) was suspended in tetrahydrofuran (4 ml). Thereafter, hexamethyldisilane lithium salts (1.2 M tetrahydrofuran solution, 0.67 ml) was added to the suspension, and the obtained mixture was stirred for 3 minutes. Thereafter, the aforementioned (S)-1-cyano-3-[1-(4-methoxyphenyl)ethyl]-2-phenyl isourea (142 mg) was added to the reaction solution, and the mixture was then stirred at a room temperature for 90 minutes. Thereafter, the reaction solution was neutralized with an aqueous 10% ammonium chloride solution, the resultant solution was then concentrated under a reduced pressure, and the organic solvent was then eliminated. After the precipitate was centrifuged, the supernatant was discarded. The residue dissolved in methanol was purified by gel filtration column chromatography (Sephadex LH-20; 2.1 Φ×111 cm; eluted with methanol) to obtain the captioned compound (49.5 mg).

EXAMPLE 272

Synthesis of 1-(5-hydroxy-1,5-dimethylhexyl)-3-(7-thiophen-2-yl[1,2,4]triazolo[1,5-a]pyrimidin-2-yl)urea (Production Example of Reaction Formula C)

7-thiophen-2-yl[1,2,4]triazolo[1,5-a]pyrimidin-2-ylamine (the compound obtained in Reference Example 1; 2.17 g) was dissolved in 1,3-dimethylimidazolidin-2-one (DMI, 100 ml). Thereafter, 4-nitrophenyl chloroformate (3.02 g) was added to the solution, and the obtained mixture was stirred for 5 minutes under cooling on ice. Thereafter, pyridine (1.21 ml) was added thereto, and the obtained mixture was stirred for 40 minutes under cooling on ice. Thereafter, 6-amino-2-methyl-2-heptanol (5.81 g) was added thereto, and the obtained mixture was stirred for 30 minutes under cooling on ice. The reaction solution was diluted with ethylene chloride (300 ml), and the organic layer was successively washed with 4 M hydrochloric acid (200 ml×2), distilled water, and an aqueous 5% potassium carbonate solution (200 ml×2). Thereafter, the organic layer was dried over anhydrous sodium sulfate, and the solvent was distilled off under a reduced pressure. A mixed solvent consisting of ethyl acetate (40 ml) and hexane (500 ml) was added to the obtained residue (including DMI), and the mixture was then stirred. The supernatant was discarded, and the precipitate was then dissolved in ethyl acetate (250 ml), followed by washing with water. The organic layer was dried over anhydrous sodium sulfate, and the solvent was then distilled off under a reduced pressure. The obtained residue was purified by gel filtration column chromatography (Sephadex LH-20; 2.1 Φ×110 cm; eluted with methanol) to obtain the captioned compound (1.48 g).

EXAMPLE 300

Synthesis of (S)-1-[1-(3-methoxyphenyl)ethyl]-3-[7-(3,4-methylenedioxyphenyl)-[1,2,4]triazolo[1,5-a]pyrimidin-2-yl]urea (Production Example of Reaction Formula C)

7-(3,4-methylenedioxyphenyl)-[1,2,4]triazolo[1,5-a]pyrimidin-2-ylamine (the compound obtained in Reference Example 15; 1.277 g) was dissolved in DMI (50 ml). After the obtained solution was cooled on ice, pyridine (0.61 ml) and 4-nitrophenyl chloroformate (1.511 g) were added to the solution, and the obtained mixture was stirred at the same temperature for 70 minutes. Thereafter, (S)-1-(3-methoxyphenyl)ethylamine (2.277 g) was added thereto, and the obtained mixture was stirred at the same temperature for 1 hour. Thereafter, water (10 ml) was added thereto, and the reaction was terminated. Thereafter, methylene chloride (200 ml) was added to the reaction solution, and the obtained mixture was successively washed with 4 M hydrochloric acid (200 ml ×4), an aqueous saturated potassium carbonate solution (200 ml×4), and water (300 ml×2). Thereafter, the organic layer was concentrated under a reduced pressure. The obtained residue was dissolved in ethyl acetate under heating (70° C. to 80° C.), and insoluble matters were then eliminated by hot filtration. Thereafter, the filtrate was concentrated, and the concentrate was then crystallized from ethyl acetate (90 ml). The obtained crystals were dissolved in methylene chloride (150 ml), and insoluble matters were than eliminated by filtration. The filtrate was concentrated, and the concentrate was then dissolved in ethyl acetate (250 ml) under heating (70° C. to 80° C.). Thereafter, the solvent was concentrated to an amount of approximately one-third, and the precipitate was eliminated by filtration. The filtrate was concentrated, and the residue was recrystallized from methanol. The obtained crystals were purified by silica gel column chromatography (eluted with 1% to 2% methanol-containing methylene chloride) to obtain the captioned compound (0.576 g).

EXAMPLE 302

Synthesis of 1-[7-(3,4-methylenedioxyphenyl)-[1,2,4]triazolo[1,5-a]pyrimidin-2-yl]-3-[1-(3,4,5-trimethoxyphenyl)ethyl]urea (Production Example of Reaction Formula C)

7-(3,4-methylenedioxyphenyl)-[1,2,4]triazolo[1,5-a]pyrimidin-2-ylamine (the compound obtained in Reference Example 15; 0.510 g) and 4-nitrophenyl chloroformate (0.605 g) were dissolved in DMI (20 ml). After the obtained solution was cooled on ice, pyridine (0.24 ml) was added to the solution, and the obtained mixture was stirred at the same temperature for 70 minutes.

1-(3,4,5-trimethoxyphenyl)ethylamine (1.268 g) was added to the reaction product, and the obtained mixture was stirred at the same temperature for 6 hours 40 minutes. Thereafter, ethyl acetate (200 ml) was added to the reaction solution, and hexane (600 ml) was then added dropwise to the obtained mixture. After ultrasonic sound was applied to the mixture for 10 minutes, the precipitate was collected by filtration, and it was then dissolved in ethyl acetate (100 ml) again. Thereafter, hexane (300 ml) was added dropwise to the solution, and the supernatant was discarded, followed by collection of the precipitate. This precipitate was dissolved in methanol (100 ml) under heating (60° C.), and insoluble matters were then eliminated by filtration. The filtrate was concentrated, and the residue was dissolved in methylene chloride (50 ml). The obtained mixture was successively washed with 4 M hydrochloric acid (40 ml×4), an aqueous saturated sodium carbonate solution (40 ml×4), and water (40 ml×2). After the resultant product was dried, the organic layer was concentrated under a reduced pressure. The obtained residue was purified by silica gel column chromatography (eluted with 1% to 2% methanol-containing methylene chloride) to obtain the captioned compound (0.233 g).

EXAMPLE 306

Synthesis of 1-[1-(3,4-methylenedioxyphenyl)ethyl] 3-[7-(3-pyridin-3-ylmethoxy)phenyl)-[1,2,4]triazolo [1,5-a]pyrimidin-2-yl]urea (Production Example of Reaction Formula C)

7-(3-(pyridin-3-ylmethoxy)phenyl)-[1,2,4]triazolo[1,5-a]pyrimidin-2-ylamine (the compound obtained in Reference Example 22; 0.536 g) and 4-nitrophenyl chloroformate (0.509 g) were dissolved in DMI (13 ml). After the obtained solution was cooled on ice, pyridine (0.20 ml) was added to the solution, and the obtained mixture was stirred at the same temperature for 1 hour. Thereafter, 1-(3,4-methylenedioxyphenyl)ethylamine (0.695 g) was added to the reaction product, and the obtained mixture was stirred at the same temperature for 3 hours 40 minutes. Thereafter, water (1 ml) was added thereto, and the reaction was terminated. Thereafter, ethyl acetate (168 ml) was added to the reaction solution, and the obtained mixture was added dropwise to hexane (505 ml). After ultrasonic sound was applied to the mixture for 10 minutes, the precipitate was collected by filtration. The resultant was suspended in a mixed solvent consisting of hexane and ethyl acetate (3:1; 60 ml). After ultrasonic sound was applied to the suspension for 10 minutes, the precipitate was collected by filtration. The resultant was purified by silica gel column chromatography (eluted with 2% methanol-containing methylene chloride) to obtain the captioned compound (0.454 g).

EXAMPLE 313

Synthesis of 1-(5-hydroxy-1,5-dimethylhexyl)-3-{7-[3-(pyridin-3-ylmethoxy)phenyl]-[1,2,4]triazolo[1,5-a]pyrimidin-2-yl}urea (Production Example of Reaction Formula C)

4-nitrophenyl chloroformate (0.786 g) was dissolved in DMI (20 ml). Thereafter, 7-[3-(pyridin-3-ylmethoxy)phenyl]-[1,2,4]triazolo[1,5-a]pyrimidin-2-ylamine (the compound obtained in Reference Example 22; 0.828 g) and pyridine (421 al) were added to the solution, while stirring at 10° C. After the mixture was stirred at 10° C. for 1 hour, a DMI solution (1.5 ml) containing 6-amino-2-methyl-2-heptanol (1.133 g) was added thereto. The obtained mixture was stirred at 10° C. for 2.5 hours, and it was then stirred overnight, while the temperature was gradually increased to a room temperature. Thereafter, the solvent was distilled off under a reduced pressure (63° C., 1 mmHg), and the residue was dissolved in methylene chloride (500 ml). The obtained solution was then washed with an aqueous 1 M sodium hydroxide solution and a saturated saline solution. The organic layer was dried over anhydrous sodium sulfate, and the solvent was distilled off under a reduced pressure. The obtained residue was washed by suspension in a mixed solvent consisting of diethyl ether and hexane (1:1; 20 ml×2). The residue was purified by silica gel column chromatography (eluted with 3% to 7% methanol-containing methylene chloride) to obtain the captioned compound (1.129 g).

EXAMPLE 317

Synthesis of (±)-1-(4-hydroxy-1,4-dimethylpentyl)-3-[7-(4-methoxyphenyl)-[1,2,4]triazolo[1,5-a]pyrimidin-2-yl]urea (Production Example of Reaction Formula C)

A commercially available hexan-2,5-dion (137 g) was dissolved in benzene (300 ml). Thereafter, ethylene glycol (100 ml) and p-toluenesulfonic acid (11.4 g) were added to the solution, and the mixture was then dehydrated by heating to reflux for 5 hours. The reaction product was diluted with ethyl acetate, and then washed with an aqueous saturated sodium bicarbonate solution and a saturated saline solution. The organic layer was then dried over anhydrous sodium sulfate. The solvent was-distilled off under a reduced pressure, and the residue was subjected to vacuum distillation (80° C. to 82° C./3 mmHg) to obtain 4-(2-methyl[1,3]dioxolan-2-yl)butan-2-one (56.83 g).

$^1$H-NMR (CDCl$_3$): 1.32 (3H, s), 1.98 (2H, t, J=7.6), 2.16 (3H, s), 2.52 (2H, t, J=7.6), 3.88-3.98 (4H, overlapped)

The obtained 4-(2-methyl[1,3]dioxolan-2-yl)butan-2-one (27.60 g) was dissolved in tetrahydrofuran (220 ml), and thereafter, methylmagnesium bromide (3 M tetrahydrofuran solution; 85 ml) was added to the solution at a room temperature. The obtained mixture was stirred for 40 minutes, and an aqueous saturated ammonium chloride solution (300 ml) was then added thereto, followed by extraction with ethyl acetate (300 ml×3). The organic layer was washed with a saturated saline solution, and then dried over anhydrous sodium sulfate. The solvent was then distilled off under a reduced pressure. The residue was purified by silica gel column chromatography (eluted with ethyl acetate-hexane (1:1)) to obtain 2-methyl-4-(2-methyl[1,3]dioxolan-2-yl)butan-2-ol (21.18 g).

$^1$H-NMR (CDCl$_3$): 1.22 (6H, s), 1.34 (3H, s), 1.54-1.82 (4H, overlapped), 3.9-4.0 (4H, m)

The obtained 2-methyl-4-(2-methyl[1,3]dioxolan-2-yl)butan-2-ol (21.18 g) was dissolved in acetone (165 ml). Thereafter, 1 M hydrochloric acid (6.6 ml) was added to the solution, and the obtained mixture was stirred at a room temperature for 2 hours. The reaction solution was neutralized with an aqueous 1 M sodium hydroxide solution. Thereafter, a saturated saline solution (100 ml) was added thereto, and acetone was then distilled off under a reduced pressure. After extraction with chloroform (200 ml×4), the organic layer was dried over anhydrous sodium sulfate. The solvent was then eliminated under a reduced pressure to obtain 5-hydroxy-5-methylhexan-2-one (14.23 g).

$^1$H-NMR (CDCl$_3$): 1.22 (6H, s), 1.77 (2H, t, J=7.4), 2.19 (3H, s), 2.59 (2H, t, J=7.4)

The obtained 5-hydroxy-5-methylhexan-2-one (14.23 g) was dissolved in methylene chloride (520 ml). Thereafter, benzhydrylamine (21.00 g) was added to the solution, and the obtained mixture was stirred at a room temperature overnight. Thereafter, sodium triacetoxy borohydride (46.30 g) was added to the reaction solution, and the obtained mixture was stirred at a room temperature for 4 hours. Thereafter, distilled water (173 ml) was added to the reaction solution, and the obtained solution was then adjusted to be pH 12 by addition of an aqueous 6 M sodium hydroxide solution. After extraction with chloroform, the organic layer was washed with a saturated saline solution and then dried over anhydrous sodium sulfate. The solvent was distilled off under a reduced pressure, and the obtained residue was purified by silica gel column chromatography (eluted with 67% ethyl acetate-hexane) to obtain 5-benzhydrylamino-2-methylhexan-2-ol (22.80 g).

$^1$H-NMR (CDCl$_3$): 1.07 (3H, d, J=6.3), 1.31 (3H, s), 1.34-1.84 (4H, overlapped), 2.58 (1H, m), 3.86-3.96 (4H, overlapped), 4.98(1H, s), 7.18-7.44 (10H, overlapped)

The obtained 5-benzhydrylamino-2-methylhexan-2-ol (5.20 g) was dissolved in methanol (250 ml), and thereafter, palladium hydroxide (2.00 g) was added to this solution. The mixture was then stirred in an autoclave under a hydrogen pressure of 9 kg/cm for 2.5 hours. The reaction solution was filtrated using a filter medium (Celite), and the filtrate was then concentrated under a reduced pressure. Thereafter, distilled water (50 ml) was added to the residue, and the liquid was then adjusted to be pH 2.0 by addition of 1 M hydrochloric acid. Thereafter, the solution was washed with diethyl ether (100 ml×3). The water layer was adjusted to be pH 12 by addition of an aqueous 6 M sodium hydroxide solution, followed by extraction with chloroform (100 ml×3). The organic layer was washed with a saturated saline solution and then dried over anhydrous sodium sulfate. The solvent was distilled off under a reduced pressure to obtain 5-amino-2-methyl-2-hexanol (2.01 g).

$^1$H-NMR (CDCl$_3$): 1.12 (3H, d, J=6.4), 1.22 (6H, s), 1.3-1.7 (4H, overlapped), 2.90 (1H, m)

7-(4-methoxyphenyl)-[1,2,4]triazolo[1,5-a]pyrimidin-2-ylamine (the compound obtained in Reference Example 8; 579 mg) was dissolved in DMI (24 ml). Thereafter, 4-nitrophenyl chloroformate (726 mg) was added to the solution, and the obtained mixture was stirred under cooling on ice. Thereafter, pyridine (292 μl) was further added thereto, and the obtained mixture was stirred for 45 minutes under cooling on ice. Subsequently, a DMI solution (2 ml) containing 5-amino-2-methyl-2-hexanol (1.25 g) was added to the reaction solution, and the obtained mixture was then stirred for 30 minutes under cooling on ice. Thereafter, diisopropyl ether (200 ml) was added to the reaction solution, and the mixture was then stirred for 10 minutes to obtain a syrup-form precipitate. The supernatant was discarded, and the precipitate was dissolved in a mixed solvent (100 ml) consisting of 5% methanol and methylene chloride. The obtained solution was then washed with 1 M hydrochloric acid (100 ml), an aqueous 5% potassium carbonate solution (100 ml), and distilled water (100 ml). The organic layer was dried over anhydrous sodium sulfate, and the solvent was then distilled off under a reduced pressure. The obtained residue was purified by gel filtration column chromatography (Sephadex LH-20; 2.1 Φ×112 cm; eluted with methanol) and by silica gel column chromatography (1.6 Φ×21 cm; eluted with 0% to 4% methanol-containing methylene chloride) to obtain the captioned compound (368 mg).

EXAMPLE 319

Synthesis of (S)-1-(5-hydroxy-1,5-dimethylhexyl)-3-[7-(4-methoxyphenyl)-[1,2,4]triazolo[1,5-a]pyrimidin-2-yl]urea (Production Example of Reaction Formula C)

7-(4-methoxyphenyl)-[1,2,4]triazolo[1,5-a]pyrimidin-2-ylamine (the compound obtained in Reference Example 8; 72.4 mg) was dissolved in DMI (3 ml). Thereafter, 4-nitrophenyl chloroformate (90.7 mg) was added to the solution, and the obtained mixture was stirred under cooling on ice. Thereafter, pyridine (36.4 μl) was further added thereto, and the obtained mixture was stirred for 45 minutes under cooling on ice. Subsequently, (S)-6-amino-2-methyl-2-heptanol (175 mg) was added to the reaction solution, and while stirring, the temperature of the mixture was gradually increased to a room temperature overnight. Thereafter, diisopropyl ether (10 ml) was added to the reaction solution. The generated oily precipitate was separated, and it was further washed with diisopropyl ether. The residue was dissolved in ethyl acetate (20 ml), and the obtained solution was washed with an aqueous 5% potassium carbonate solution (15 ml) and distilled water. The organic layer was dried over anhydrous sodium sulfate, and the solvent was then distilled off under a reduced pressure. The obtained residue was purified by gel filtration column chromatography (Sephadex LH-20; 2.1 Φ×110 cm; eluted with methanol) to obtain the captioned compound (48.2 mg).

EXAMPLE 327

Synthesis of 1-[7-(3,4-methylenedioxyphenyl)-[1,2,4]triazolo[1,5-a]pyrimidin-2-yl]-3-(3-ethoxy-1-methylpropyl)urea (Production Example of Reaction Formula C)

7-(3,4-methylenedioxyphenyl)-[1,2,4]triazolo[1,5-a]pyrimidin-2-ylamine (the compound obtained in Reference Example 15; 766 mg) was dissolved in DMI (30 ml). Thereafter, 4-nitrophenyl chloroformate (907 mg) was added to the solution, and the obtained mixture was stirred under cooling on ice. Thereafter, pyridine (365 μl) was further added thereto, and the obtained mixture was stirred for 45 minutes under cooling on ice. Subsequently, 3-ethoxy-1-methylpropylamine (1.40 g) was added to the reaction solution, and the obtained mixture was then stirred for 1 hour under cooling on ice. Thereafter, the reaction solution was diluted with methylene chloride (160 ml), and the obtained solution was then washed with 1 M hydrochloric acid (160 ml), distilled water (160 ml), an aqueous 5% potassium carbonate solution (160 ml), and a saturated saline solution (160 ml). The organic layer was dried over anhydrous sodium sulfate, and the solvent was then distilled off under a reduced pressure. The residue containing DMI was diluted with ethyl acetate (200 ml) and then washed with distilled water (200 ml×4). The resultant product was dried over anhydrous sodium sulfate, and the solvent was then distilled off under a reduced pressure. The obtained residue was purified by silica gel column chromatography (2.3 Φ×22 cm; eluted with 1% to 2% methanol-containing methylene chloride) and by gel filtration column chromatography (Sephadex LH-20; 2.1 Φ×112 cm; eluted with methanol) to obtain the captioned compound (442 mg).

EXAMPLE 333

Synthesis of 1-(4-methoxy-1-methylbutyl)-3-[7-(4-methoxyphenyl)-[1,2,4]triazolo[1,5-a]pyrimidin-2-yl]urea (Production Example of Reaction Formula C)

4-nitrophenyl chloroformate (644 mg) was dissolved in DMI (26 ml). Thereafter, while stirring under cooling on ice, 7-(4-methoxyphenyl)-[1,2,4]triazolo[1,5-a]pyrimidin-2-ylamine (the compound obtained in Reference Example 8; 514 mg) and pyridine (347 µl) were added to the solution. The obtained mixture was stirred for 40 minutes under cooling on ice. Thereafter, 4-methoxy-1-methylpropylamine (500 mg) was added thereto, and the obtained mixture was stirred for 1 hour under cooling on ice. Subsequently, the reaction solution was stirred at a room temperature overnight. Thereafter, an ice block and an aqueous 3 M sodium hydroxide solution were added to the reaction solution, followed by extraction with methylene chloride. The organic layer was washed with a saturated saline solution and then dried over anhydrous sodium sulfate. The solvent was then distilled off under a reduced pressure. The obtained residual solution was further subjected to vacuum distillation to eliminate DMI. Thereafter, the distillation residue was dissolved in ethyl acetate (100 ml), and the organic layer was washed with 1 M hydrochloric acid (30 ml×4) and then dried over anhydrous sodium sulfate. The solvent was distilled off under a reduced pressure. The obtained residue was purified by silica gel column chromatography (eluted with 0% to 20% methanol-containing ethyl acetate) to obtain the captioned compound (242 mg).

EXAMPLE 222

Synthesis of (S)-1-[7-(4-benzyloxyphenyl)-[1,2,4]triazolo[1,5-a]pyrimidin-2-yl]-3-[1-(3-methoxyphenyl)ethyl]urea (Production Example of Reaction Formula C)

7-(4-benzyloxyphenyl)-[1,2,4]triazolo[1,5-a]pyrimidin-2-ylamine (the compound obtained in Reference Example 2; 6.98 g) was dissolved in DMI (100 ml). Thereafter, 4-nitrophenyl chloroformate (6.67 g) was added to the solution. Thereafter, pyridine (2.67 ml) was added thereto under cooling on ice. The obtained mixture was stirred for 1 hour under cooling on ice. Thereafter, (S)-1-(3-methoxyphenyl)ethylamine (5.00 g) was added to the reaction solution, and the obtained mixture was stirred over a day and a night. Thereafter, the solvent was distilled off under a reduced pressure. The residue was diluted with methylene chloride, and the organic layer was then washed with 1 M hydrochloric acid and distilled water. The organic layer was dried over anhydrous sodium sulfate. The solvent was then distilled off under a reduced pressure. The obtained residue was washed by suspension in ethyl acetate to obtain the captioned compound (6.93 g).

EXAMPLE 223

Synthesis of (S)-1-[7-(4-hydroxyphenyl)-[1,2,4]triazolo[1,5-a]pyrimidin-2-yl]-3-[1-(3-methoxyphenyl)ethyl]urea (S)-1-[7-(4-benzyloxyphenyl)-[1,2,4]triazolo[1,5-a]pyrimidin-2-yl]-3-[1-(3-methoxyphenyl)ethyl]urea (the compound obtained in Example 222; 7.83 g) was dissolved in acetic acid (600 ml). Thereafter, 10% palladium carbon (50% water content; 2.0 g) was added to the solution, and the obtained mixture was stirred at 40° C. overnight in a hydrogen atmosphere. The reaction solution was filtrated with a filter medium (Celite), and the resultant was then concentrated under a reduced pressure. The residue was purified by silica gel column chromatography (eluted with 4% methanol-containing methylene chloride) to obtain the captioned compound (5.37 g).

EXAMPLE 244

Synthesis of (S)-1-{7-[4-(2-methoxyethoxy)phenyl]-[1,2,4]triazolo[1,5-a]pyrimidin-2-yl}-3-[1-(3-methoxyphenyl)ethyl]urea (S)-1-[7-(4-hydroxyphenyl)-[1,2,4]triazolo[1,5-a]pyrimidin-2-yl]-3-[1-(3-methoxyphenyl)ethyl]urea (the compound obtained in Example 223; 20.3 mg) was suspended in 2-butanone (2 ml). Thereafter, potassium carbonate (69.4 mg) and 2-methoxyethyl bromide (47.2 µl) were added to the suspension, and the obtained mixture was stirred at 80° C. for 5 hours. Thereafter, the reaction solution was diluted with methylene chloride (5 ml), and the resultant product was then washed with 1 M hydrochloric acid (5 ml×3), saturated sodium bicarbonate (5 ml×2), and distilled water (5 ml×2). The organic layer was concentrated under a reduced pressure, and the obtained residue was purified by reverse phase liquid chromatography (Inertsil PREP-ODS; 20 Φ×250 mm; eluted with water-containing acetonitrile) to obtain the captioned compound (10.7 mg).

EXAMPLE 245

Synthesis of (S)-1-[7-(4-benzyloxyphenyl)-[1,2,4]triazolo[1,5-a]pyrimidin-2-yl]-3-(1,5-dmethylhexyl)urea (Production Example of Reaction Formula C)

7-(4-benzyloxyphenyl)-[1,2,4]triazolo[1,5-a]pyrimidin-2-ylamine (the compound obtained in Reference Example 2;

8.00 g) and 4-nitrophenyl chloroformate (7.62 g) were dissolved in DMI (100 ml). After the obtained mixture was cooled on ice, pyridine (3.1 ml) was added thereto, and the obtained mixture was stirred at the same temperature for 40 minutes. Thereafter, (S)-(+)-2-amino-6-methylheptane (6.4 ml) was added to the reaction solution, and the temperature of the obtained mixture was then increased to a room temperature, followed by stirring overnight. Thereafter, the solvent was distilled off under a reduced pressure. Subsequently, methylene chloride (100 ml) was added to the residue and dissolved therein, and the obtained solution was then successively washed with 1 M hydrochloric acid (100 ml×3), an aqueous 5% potassium carbonate solution (100 ml×5), and a saturated saline solution (200 ml). The organic layer was concentrated under a reduced pressure. The residue was dissolved in ethyl acetate (286 ml), and the obtained solution was then added dropwise to hexane (429 ml). The precipitate was collected by filtration, and the resultant was then purified by silica gel column chromatography (eluted with 1% methanol-containing methylene chloride) to obtain the captioned compound (7.39 g).

EXAMPLE 255

Synthesis of (S)-1-(1,5-dimethylhexyl)-3-[7-(4-hydroxyphenyl)-[1,2,4]triazolo[1,5-a]pyrimidin-2-yl]urea (S)-1-[7-(4-benzyloxyphenyl)-[1,2,4]triazolo[1,5-a]pyrimidin-2-yl]-3-(1,5-dimethylhexyl)urea (the compound obtained in Example 245; 7.1 g) and palladium carbon (50% water content; 2.0 g) were suspended in acetic acid (570 ml), and the obtained suspension was stirred in a hydrogen atmosphere at a room temperature for 5 days. Thereafter, the reaction solution was filtrated with a filter medium (Celite), and the collected product was then washed with methanol. The filtrate and the washing solution were mixed, and the obtained mixture was then concentrated under a reduced pressure. The obtained residue was dissolved in methylene chloride (150 ml), and the obtained solution was washed with a saturated saline solution (100 ml) twice. The saturated saline solution layer obtained after the second washing was extracted with methylene chloride (70 ml×3). The organic layers were gathered, and the obtained layer was then concentrated under a reduced pressure. The obtained residue was purified by silica gel column chromatography (eluted with 1% to 2% methanol-containing methylene chloride) to obtain the captioned compound (4.72 g).

EXAMPLE 262

Synthesis of (S)-1-(1,5-dimethylhexyl)-3-{7-[4-(2-methoxyethoxy)phenyl]-[1,2,4]triazolo[1,5-a]pyrimidin-2-yl}urea (S)-1-(1,5-dimethylhexyl)-3-[7-(4-hydroxyphenyl)-[1,2,4]triazolo[1,5-a]pyrimidin-2-yl]urea (the compound obtained in Example 255; 30 mg) and potassium carbonate (108 mg) were suspended in methyl ethyl ketone (3 ml). Thereafter, 2-methoxyethyl bromide (327 mg) was added to the obtained suspension, and the obtained mixture was stirred at 80° C. for 10 hours. Thereafter, the reaction solution was cooled to a room temperature, and methylene chloride (5 ml) was then added thereto. The obtained mixture was washed with an aqueous 1 M hydrochloric acid solution (5 ml×3), an aqueous saturated sodium bicarbonate solution (5 ml×2), and distilled water (5 ml×2). The organic layer was concentrated under a reduced pressure, and the obtained residue was purified by reverse phase liquid chromatography (Inertsil PREP-ODS; 20 Φ×250 mm; eluted with water-containing acetonitrile) to obtain the captioned compound (14 mg).

EXAMPLE 258

Synthesis of (S)-1-(1,5-dimethylhexyl)-3-{7-[4-(2-morpholin-4-ylethoxy)phenyl]-[1,2,4]triazolo[1,5-a]pyrimidin-2-yl}urea hydrochloride (S)-1-(1,5-dimethylhexyl)-3-[7-(4-hydroxyphenyl)-[1,2,4]triazolo[1,5-a]pyrimidin-2-yl]urea (the compound obtained in Example 255; 20 mg) was dissolved in methylene chloride (1 ml) in an argon atmosphere. Thereafter, 2-morpholin-4-ylethanol (21 mg) and triphenylphosphine (41 mg) were added to the obtained solution, and the obtained mixture was stirred at a room temperature for 30 minutes. Thereafter, the reaction solution was cooled on ice, and diethyl azodicarboxylate (27 mg) was then added thereto, followed by stirring the mixture at the same temperature for 30 minutes. The reaction solution was further stirred at a room temperature overnight. Thereafter, the reaction solution was concentrated under a reduced pressure. Thereafter, ethyl acetate (3 ml) and 1 M hydrochloric acid (3 ml) were added thereto, and the obtained mixture was separated. After the obtained water layer was washed with ethyl acetate (3 ml), an aqueous 6 M sodium hydroxide solution was added thereto to convert the solution to be alkaline. After extraction with methylene chloride (5 ml), the organic layer was washed with distilled water (5 ml×2), and the solvent was then distilled off under a reduced pressure. The residue was washed by suspension in a mixed solvent (2 ml) consisting of 50% ethyl acetate and hexane to obtain the captioned compound in the form of a free body (18 mg). Thereafter, methanol (1 ml) and 1 M hydrochloric acid (0.2 ml) were added to the obtained compound and dissolved therein, and the obtained mixture was then concentrated under a reduced pressure. The obtained residue was washed by suspension in acetone (0.5 ml) to obtained the captioned compound (17 mg).

Hereafter, using the [1,2,4]triazolo[1,5-a]pyrimidin-2-ylamine derivatives produced by the methods described in reference examples or methods equivalent to known methods, and known amines or amine derivatives, or amines or amine derivatives produced by methods equivalent to known methods, [1,2,4]triazolo[1,5-a]pyrimidin-2-ylurea derivatives corresponding to the compounds of Examples 001 to 337 were produced by the methods described in the aforementioned examples, methods based on common organic synthesis reactions, or other methods. The structural formulas and physicochemical data of the produced compounds of Examples 001 to 337 are shown in Tables 4 and 5.

In the tables, compounds having symbols such as "(S)—," "(R)—," or "(S,S)—" in their structural formulas indicate optically active bodies, wherein the configuration of an asymmetric carbon atom is an (S)-form, (R)-form, or (S,S)-form.

TABLE 4

| Example No. | Absolute configuration | Structural formula R— | Ar— | Molecular weight | MS: m/z (M + H)+ | Physicochemical data ¹H-NMR (200 MHz, DMSO-d6): δ |
|---|---|---|---|---|---|---|
| 001 | | phenyl | 2-thienyl | 336.37 | 337 | 7.09 (1H, m), 7.38 (2H, m), 7.46 (1H, dd, J = 4.0, 5.1 Hz), 7.61 (2H, m), 7.92 (1H, d, J = 5.1 Hz), 8.26 (1H, dd, J = 1.1, 5.1 Hz), 8.60 (1H, dd, J = 1.1, 4.0 Hz), 8.76 (1H, d, J = 5.1 Hz), 10.20 (1H, brs), 10.55 (1H, s). |
| 011 | | phenyl | 4-OCH₃-phenyl | 360.37 | 361 | 3.91 (3H, s), 7.07 (1H, m), 7.22 (2H, m), 7.38 (2H, m), 7.65 (2H, m), 7.55 (1H, d, J = 5.0 Hz), 8.28(2H, m), 8.78 (1H, d, J = 5.0 Hz), 10.34 (1H, s), 10.45 (1H, s). |
| 015 | | cyclohexyl | 4-OCH₃-phenyl | 366.42 | 367 | 1.10-1.80 (8H, overlapped), 1.80-2.00 (2H, m), 3.61 (1H, m), 3.89 (3H, s), 7.17 (2H, m), 7.49 (1H, d, J = 4.9 Hz), 8.16 (1H, d, J = 7.7 Hz), 8.22 (2H, m), 8.73 (1H, d, J = 4.9 Hz), 10.03 (1H, s). |
| 020 | | phenyl | 4-OH-phenyl | 346.34 | 347 | 1.10-2.00 (10H, m), 3.62 (1H, m), 6.99 (2H, m), 7.45 (1H, d, J = 5.0 Hz), 8.14 (3H, overlapped), 8.70 (1H, d, J = 5.0 Hz), 10.01 (1H, s), 10.40 (1H, brs). |

TABLE 4-continued

| Example No. | Absolute configuration | Structural formula | | Molecular weight | MS: m/z (M + H)+ | Physicochemical data  1H-NMR (200 MHz, DMSO-d6): δ |
|---|---|---|---|---|---|---|
| | | R— | Ar— | | | |
| 029 | | H3C-CH(CH3)- | 2-thienyl | 302.35 | 303 | 1.25 (6H, d, J = 6.6 Hz), 3.96 (1H, m), 7.45 (1H, dd, J = 4.0, 4.9 Hz), 7.89 (1H, d, J = 5.2 Hz), 7.97 (1H, brd, J = 7.4 Hz), 8.27 (1H, dd, J = 1.0, 5.1 Hz), 8.55 (1H, dd, J = 1.1, 3.9 Hz), 8.71 (1H, d, J = 5.2 Hz), 10.17 (1H, brs). |
| 030 | | H3C-CH(CH3)- | 4-OCH3-C6H4- | 326.35 | 327 | 1.18 (6H, d, J = 6.6 Hz), 3.77-3.99 (4H, overlapped), 7.13-7.23 (2H, m), 7.50 (1H, d, J = 4.9 Hz), 8.05 (1H, d, J = 7.3 Hz), 8.18-8.28 (2H, m), 8.73 (1H, d, J = 4.9 Hz), 10.03 (1H, brs). |
| 037 | | 4-hydroxycyclohexyl | 4-OCH3-C6H4- | 382.42 | 383 | 1.10-1.40 (4H, overlapped), 1.70-2.10 (4H, overlapped), 3.20-3.70 (2H, overlapped), 3.89 (3H, s), 4.58 (1H, brs), 7.17 (2H, m), 7.49 (1H, d, J = 4.9 Hz), 8.09 (1H, d, J = 7.4 Hz), 8.21 (2H, m), 8.72 (1H, d, J = 4.9 Hz), 10.04 (1H, s). |
| 039 | | 3-pyridylmethyl | 4-OCH3-C6H4- | 375.38 | 376 | 3.88 (3H, s), 4.51 (2H, brs), 7.12 (2H, m), 7.38 (1H, m), 7.50 (1H, d, J = 4.9 Hz), 7.77 (1H, m), 8.21 (2H, m), 8.50 (1H, dd, J = 1.6, 4.8 Hz), 8.60 (1H, d, J = 1.6 Hz), 8.63 (1H, brs), 8.73 (2H, d, J = 4.9 Hz), 10.26 (1H, s). |

TABLE 4-continued
| Example No. | Absolute configuration | Structural formula R– | Ar– | Molecular weight | MS: m/z (M + H)+ | 1H-NMR (200 MHz, DMSO-d6): δ |
|---|---|---|---|---|---|---|
| 044 | | 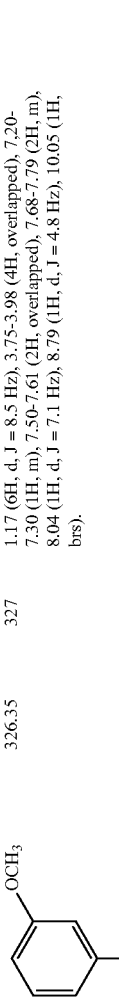 | 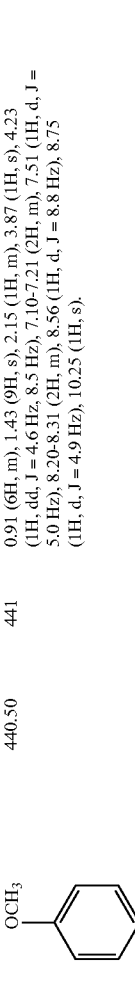 | 326.35 | 327 | 1.17 (6H, d, J = 8.5 Hz), 3.75-3.98 (4H, overlapped), 7.20-7.30 (1H, m), 7.50-7.61 (2H, overlapped), 7.68-7.79 (2H, m), 8.04 (1H, d, J = 7.1 Hz), 8.79 (1H, d, J = 4.8 Hz), 10.05 (1H, brs). |
| 045 | |  |  | 440.50 | 441 | 0.91 (6H, m), 1.43 (9H, s), 2.15 (1H, m), 3.87 (1H, s), 4.23 (1H, dd, J = 4.6 Hz, 8.5 Hz), 7.10-7.21 (2H, m), 7.51 (1H, d, J = 5.0 Hz), 8.20-8.31 (2H, m), 8.56 (1H, d, J = 8.8 Hz), 8.75 (1H, d, J = 4.9 Hz), 10.25 (1H, s). |
| 049 | (S)- | | | 412.44 | 413 | 1.37 (3H, d, J = 7.3 Hz), 1.44 (9H, s), 3.89 (3H, s), 4.26 (1H, m), 7.12-7.25 (2H, m), 7.53 (1H, d, J = 5.0 Hz), 8.20-8.35 (2H, m), 8.53 (1H, d, J = 7.0 Hz), 8.75 (1H, d, J = 4.8 Hz), 10.24 (1H, s). |
| 051 | (R)- | | | 412.44 | 413 | 1.37 (3H, d, J = 7.3 Hz), 1.44 (9H, s), 3.89 (3H, s), 4.26 (1H, m), 7.12-7.25 (2H, m), 7.53 (1H, d, J = 5.0 Hz), 8.20-8.35 (2H, m), 8.53 (1H, d, J = 7.0 Hz), 8.75 (1H, d, J = 4.8 Hz), 10.24 (1H, s). |

TABLE 4-continued

| Example No. | Absolute configuration | Structural formula R— | Ar— | Molecular weight | MS: m/z (M + H)+ | ¹H-NMR (200 MHz, DMSO-d6): δ |
|---|---|---|---|---|---|---|
| 053 | | CH₃-CH(CH₃)- | 4-OH-C₆H₄- | 312.33 | 313 | 1.19 (6H, d, J = 8.5 Hz), 3.87 (1H, m), 6.94-7.04 (2H, m), 7.45 (1H, d, J = 5.0 Hz), 8.04 (1H, d, J = 7.3 Hz), 8.10-8.20 (2H, m), 8.70 (1H, d, J = 5.1 Hz), 10.00 (1H, s), 10.41 (1H, brs). |
| 054 | (S)- | H₃C-CH(CH₃)-CH(COOH)- | 4-OCH₃-C₆H₄- | 384.39 | 385 | 0.89 (3H, d, J = 7.0 Hz), 0.94 (3H, d, J = 6.9 Hz), 2.17 (1H, m), 3.88 (3H, s), 4.28 (1H, dd, J = 4.6 Hz, 8.5 Hz), 7.09-7.22 (2H, m), 7.51 (1H, d, J = 5.0 Hz), 8.19-8.31 (2H, m), 8.52 (1H, d, J = 8.4 Hz), 8.74 (1H, d, J = 5.0 Hz), 10.24 (1H, s). |
| 055 | (S)- | H₃C-CH(CH₃)-CH(CONHCH₃)- | 4-OCH₃-C₆H₄- | 397.43 | 398 | 0.85 (3H, d, J = 6.9 Hz), 0.90 (3H, d, J = 6.8 Hz), 2.02 (1H, m), 2.63 (3H, s), 3.88 (3H, s), 4.20 (1H, dd, J = 5.9 Hz, 8.8 Hz), 7.11-7.23 (2H, m), 7.52 (1H, d, J = 5.0 Hz), 8.05 (1H, m), 8.24-8.36 (2H, m), 8.45 (1H, d, J = 8.7 Hz), 8.74 (1H, d, J = 5.0 Hz), 10.15 (1H, s). |
| 056 | (S)- | H₃C-CH(CH₃)-CH(CON(CH₃)₂)- | 4-OCH₃-C₆H₄- | 411.46 | 412 | 0.87 (6H, d, J = 6.8 Hz), 0.92 (3H, d, J = 6.7 Hz), 2.00 (1H, m), 2.88 (3H, s), 3.10 (3H, s), 3.88 (3H, s), 4.73 (1H, dd, J = 5.9 Hz, 8.8 Hz), 7.11-7.23 (2H, m), 7.53 (1H, d, J = 5.0 Hz), 8.25-8.37 (2H, m), 8.47 (1H, d, J = 8.5 Hz), 8.74 (1H, d, J = 5.0 Hz), 10.17 (1H, s). |

TABLE 4-continued

| Example No. | Absolute configuration | Structural formula R— | Ar→ | Molecular weight | MS: m/z (M + H)+ | ¹H-NMR (200 MHz, DMSO-d6): δ |
|---|---|---|---|---|---|---|
| 058 | (S)- | H₃C-CH(CH₃)-CH(–)-C(O)-NH-CH₂-(4-pyridyl) | 4-OCH₃-C₆H₄- | 474.52 | 475 | 0.87 (3H, d, J = 6.7 Hz), 0.93 (3H, d, J = 6.7 Hz), 2.12 (1H, m), 3.85 (3H, s), 4.20-4.45 (3H, m), 7.08-7.20 (2H, m), 7.22-7.32 (2H, m), 7.52 (1H, d, J = 5.0 Hz), 8.21-8.35 (2H, m), 8.43-8.57 (3H, m), 8.69-8.82 (2H, m), 10.22 (1H, s). |
| 059 | | HCl · 1-benzyl-piperidin-4-yl | 4-OCH₃-C₆H₄- | 493.99 | 458 | 1.7-2.3 (4H, overlapped), 2.9-3.5 (4H, overlapped), 3.84 (1H, m), 3.89 (3H, s), 4.24-4.36 (2H, overlapped), 7.27 (2H, m), 7.4-7.7 (6H, overlapped), 8.14 (1H, brd, J = 7.0 Hz), 8.22 (2H, m), 8.74 (1H, d, J = 4.8 Hz), 10.18 (1H, s), 10.93 (1H, brs). |
| 063 | | 2-(piperidin-1-yl)ethyl | 4-OCH₃-C₆H₄- | 395.46 | 396 | 0.88 (6H, dd, J = 6.9 Hz, 9.2 Hz), 1.25-2.42 (13H, m), 3.02-3.45 (2H, m), 3.48 (3H, s), 4.15-4.32 (1H, m), 7.11-7.23 (1H, m), 7.52 (1H, d, J = 4.9 Hz), 7.99 (1H, m), 8.24-8.38 (2H, m), 8.46 (1H, d, J = 8.5 Hz), 8.74 (1H, d, J = 5.0 Hz), 10.15 (1H, s). |
| 067 | | 3-(morpholin-4-yl)propyl | 4-OCH₃-C₆H₄- | 411.46 | 412 | 1.59-1.77 (2H, m), 2.27-2.41 (5H, m), 3.14-3.45 (3H, m), 3.52-3.62 (4H, m), 3.90 (3H, s), 7.14-7.27 (2H, m), 7.51 (1H, d, J = 4.9 Hz), 8.16-8.31 (2H, overlapped), 8.74 (1H, d, J = 5.0 Hz), 10.06 (1H, s). |

TABLE 4-continued

| Example No. | Absolute configuration | Structural formula R— | Ar— | Molecular weight | MS: m/z (M + H)+ | Physicochemical data ¹H-NMR (200 MHz, DMSO-d6): δ |
|---|---|---|---|---|---|---|
| 069 | (S)- | H₃C—N(piperazine)-C(=O)-CH(·)-CH(CH₃)-CH₃ with H₃C | 4-OCH₃-C₆H₄- | 466.54 | 467 | 0.86 (3H, d, J = 6.8 Hz), 0.92 (3H, d, J = 6.6 Hz), 1.98 (1H, m), 2.18 (3H, s), 2.21-2.40 (4H, m), 3.40-3.67 (4H, m), 3.88 (3H, m), 4.76 (1H, m), 7.11-7.23 (2H, m), 7.52 (1H, d, J = 5.0 Hz), 8.26-8.38 (2H, m), 8.50 (1H, d, J = 8.9 Hz), 8.74 (1H, d, J = 4.9 Hz), 10.17 (1H, s). |
| 072 | | HO-C(=O)-CH₂-CH₂-(·) | 4-OCH₃-C₆H₄- | 356.34 | 357 | 2.51 (2H, m), 3.42 (2H, m), 3.89 (3H, s), 7.20 (2H, m), 7.51 (1H, d, J = 4.9 Hz), 8.25 (2H, m), 8.28 (1H, m), 8.73 (1H, d, J = 5.0 Hz), 10.10 (1H, s), 12.30 (1H, brs). |
| 084 | | (CH₃)₂CH-(·) | 3-OH-C₆H₄- | 312.33 | 313 | 1.17 (6H, d, J = 6.6 Hz), 3.86 (1H, m), 7.00-7.12 (1H, m), 7.37-7.48 (2H, overlapped), 7.48-7.57 (2H, m), 8.04 (1H, d, J = 7.1 Hz), 8.76 (1H, d, J = 4.8 Hz), 9.93 (1H, brs), 10.02 (1H, s). |
| 098 | (S,S)- | H₃CO-C(=O)-CH(CH₃)-NH-C(=O)-CH(·)-CH(CH₃)-CH₃ | 4-OCH₃-C₆H₄- | 469.49 | 470 | 0.8-1.0 (6H, m), 1.30 (3H, d, J = 7.3 Hz), 2.06 (1H, m), 3.61 (3H, s), 3.88 (3H, s), 4.22-4.46 (2H, m), 7.10-7.24 (2H, m), 7.53 (1H, d, J = 5.0 Hz), 8.24-8.38 (2H, m), 8.45 (1H, d, J = 8.8 Hz), 8.60 (1H, d, J = 7.0 Hz), 8.74 (1H, d, J = 5.0 Hz), 10.17 (1H, s). |

TABLE 4-continued

| Example No. | Absolute configuration | Structural formula | | Molecular weight | MS: m/z (M + H)+ | Physicochemical data ¹H-NMR (200 MHz, DMSO-d6): δ |
|---|---|---|---|---|---|---|
| | | R– | Ar– | | | |
| 101 | (S)- | CH₃-CH(phenyl)- | 4-OCH₃-phenyl | 388.42 | 389 | 1.47 (3H, d, J = 7.0 Hz), 3.87 (3H, s), 4.97 (1H, m), 7.14 (2H, m), 7.50 (1H, d, J = 4.9 Hz), 8.21 (2H, m), 8.57 (1H, brd, J = 7.7 Hz), 8.74 (1H, d, J = 5.0 Hz), 10.14 (1H, brs). |
| 102 | | phenyl-(CH₂)₃- | 4-OCH₃-phenyl | 402.45 | 403 | 1.70-1.94 (2H, m), 2.58-2.72 (2H, m), 3.14-3.36 (2H, overlapped), 3.84 (3H, s), 7.09-7.33 (7H, m), 7.50 (1H, d, J = 5.0 Hz), 8.16-8.30 (2H, m), 8.74 (1H, d, J 5.0 Hz), 10.08 (1H, s). |
| 108 | | cyclohexyl-CH(CH₃)-CH₂-O- | 3-substituted phenyl | 408.50 | 409 | 1.01 (6H, d, J = 6.7 Hz), 1.1-1.7 (8H, overlapped), 1.7-1.9 (2H, m), 2.06 (1H, m), 3.61 (1H, m), 3.85 (2H, d, J = 6.6 Hz), 7.23 (1H, m), 7.52 (1H, d, J = 4.9 Hz), 7.53 (1H, m), 7.64-7.74 (2H, overlapped), 8.13 (1H, m), 8.78 (1H, d, J = 4.8 Hz), 10.06 (1H, s). |
| 109 | | (CH₃)₃C-O-C(O)-(CH₂)₂- | 4-OCH₃-phenyl | 412.44 | 413 | 1.39 (9H, s), 2.47 (2H, m), 3.44 (2H, m), 3.89 (3H, s), 7.20 (2H, m), 7.51 (1H, d, J = 5.0 Hz), 8.26 (2H, m), 8.30 (1H, m), 8.74 (1H, d, J = 4.9 Hz), 10.12 (1H, s). |

TABLE 4-continued

| Example No. | Absolute configuration | Structural formula | | Molecular weight | MS: m/z (M + H)+ | Physicochemical data $^1$H-NMR (200 MHz, DMSO-d6): δ |
| --- | --- | --- | --- | --- | --- | --- |
| | | R— | Ar— | | | |
| 115 | | 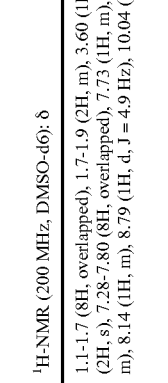 |  | 442.51 | 443 | 1.1-1.7 (8H, overlapped), 1.7-1.9 (2H, m), 3.60 (1H, m), 5.22 (2H, s), 7.28-7.80 (8H, overlapped), 7.73 (1H, m), 7.88 (1H, m), 8.14 (1H, m), 8.79 (1H, d, J = 4.9 Hz), 10.04 (1H, s). |
| 117 | (S)- |  |  | 431.45 | 432 | 1.42 (3H, d, J = 7.0 Hz), 3.88 (3H, s), 4.56 (1H, m), 7.07 (1H, brt, J = 7.6 Hz), 7.20 (2H, m), 7.33 (2H, dd, J = 7.6, 8.1 Hz), 7.54 (1H, d, J = 5.1 Hz), 7.65 (2H, brd, J = 8.1 Hz), 8.32 (2H, m), 8.59 (1H, brd, J = 7.3 Hz), 8.76 (1H, d, J = 4.8 Hz), 10.20 (1H, brs), 10.23 (1H, s). |
| 118 | (S)- | 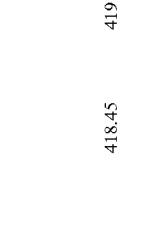 | | 425.44 | 426 | 1.29 (3H, d, J = 6.6 Hz), 3.4-3.7 (8H, overlapped), 3.89 (3H, s), 4.84 (1H, m), 7.19 (2H, m), 7.53 (1H, d, J = 5.1 Hz), 8.32 (2H, m), 8.64 (1H, brd, J = 7.5 Hz), 8.74 (1H, d, J = 4.8 Hz), 10.17 (1H, s). |
| 133 | (S)- |  | | 418.45 | 419 | 1.45 (3H, d, J = 7.0 Hz), 3.73 (3H, s), 3.88 (3H, s), 4.91 (1H, m), 6.89 (2H, m), 7.14 (2H, m), 7.28 (2H, m), 7.49 (1H, d, J = 5.1 Hz), 8.20 (2H, m), 8.48 (1H, brd, J = 7.7 Hz), 8.73 (1H, d, J = 4.8 Hz), 10.12 (1H, brs). |

TABLE 4-continued

| Example No. | Absolute configuration | Structural formula | | Molecular weight | MS: m/z (M + H)+ | Physicochemical data 1H-NMR (200 MHz, DMSO-d6): δ |
| --- | --- | --- | --- | --- | --- | --- |
| | | R— | Ar— | | | |
| 160 | (S)- | (isooctyl-like: CH3–CH(CH3)–CH2CH2CH2–CH(CH3)–) | 4-OCH3-C6H4- | 396.49 | 397 | 0.81 (6H, d, J = 6.6 Hz), 1.05-1.21 (4H, m), 1.21-1.55 (6H, m), 3.78 (1H, m), 3.89 (3H, s), 7.13-7.23 (2H, m), 7.49 (1H, d, J = 4.9 Hz), 8.02 (1H, d, J = 7.7 Hz), 8.17-8.27 (2H, m), 8.73 (1H, d, J = 4.9 Hz), 10.01 (1H, brs). |
| 165 | (S)- | CH3–CH(C6H5)– | 2-thienyl | 364.42 | 365 | 1.56 (3H, d, J = 7.0 Hz), 5.04 (1H, m), 7.23-7.48 (6H, m), 7.89 (1H, d, J = 5.1 Hz), 8.17 (1H, dd, J = 1.1 Hz, 5.1 Hz), 8.45 (1H, d, J = 7.7 Hz), 8.53 (1H, dd, J = 1.1 Hz, 3.9 Hz), 8.72 (1H, d, J = 5.1 Hz), 10.29 (1H, brs). |
| 172 | | (CH3)2CH– | 3-(isobutoxy)phenyl | 368.43 | 369 | 1.01 (3H, d, J = 6.8 Hz), 1.16 (3H, d, J = 6.52 Hz), 2.05 (1H, m), 3.76-3.96 (3H, overlapped), 7.23 (1H, m), 7.45-7.61 (2H, overlapped), 7.62-7.79 (2H, overlapped), 8.02 (1H, d, J = 7.3 Hz), 8.78 (1H, d, J = 4.8 Hz), 10.05 (1H, s). |
| 184 | | (CH3)2CH– | 3-((tetrahydrofuran-2-yl)methoxy)phenyl | 396.44 | 397 | 1.16 (6H, d, J = 6.6 Hz), 1.60-2.13 (4H, m), 3.62-3.88 (3H, m), 3.88-4.26 (3H, m), 7.20-7.30 (1H, m), 7.48-7.60 (2H, overlapped), 7.67-7.79 (2H, m), 8.03 (1H, d, J = 7.3 Hz), 8.78 (1H, d, J = 4.9 Hz), 10.06 (1H, brs). |

TABLE 4-continued

| Example No. | Absolute configuration | Structural formula | | Molecular weight | MS: m/z (M + H)+ | 1H-NMR (200 MHz, DMSO-d6): δ |
|---|---|---|---|---|---|---|
| | | R— | Ar— | | | |
| 204 | (S)- | CH₃, H₃CO-phenyl-CH- | 3-(2-morpholinoethoxy)phenyl · HCl | 631.60 | 518 | 1.44 (3H, d, J = 6.9 Hz), 3.1-4.8 (12H, m), 3.73 (3H, s), 4.92 (1H, m), 6.82 (1H, m), 6.88-6.95 (2H, m), 7.25 (1H, m), 7.30 (1H, m), 7.51-7.62 (2H, m), 7.76-7.84 (2H, m), 8.55 (1H, brd, J = 7.8 Hz), 8.82 (1H d, J = 5.0 Hz), 10.17 (1H, s), 11.51 (1H, brs). |
| 237 | (S)- | CH₃, H₃CO-CH₂-CH- | 4-methoxyphenyl | 356.38 | 357 | 1.17 (3H, d, J = 6.8 Hz), 3.27 (3H, s), 3.25-3.45 (2H, m), 3.89 (3H, s), 3.98 (1H, m), 7.17 (2H, m), 7.50 (1H, d, J = 4.9 Hz), 8.18 (1H, brd, J = 7.9 Hz), 8.23 (2H, m), 8.73 (1H, d, J = 4.9 Hz), 10.07 (1H, s). |
| 272 | | CH₃, CH₃, HO-C(CH₃)-chain-CH- | 2-thienyl | 388.49 | 389 | 1.03 (6H, s), 1.22 (3H, d, J = 6.5 Hz), 1.3-1.8 (6H, overlapped), 3.88 (1H, m), 4.07 (1H, s), 7.45 (1H, dd, J = 4.0, 5.0 Hz), 7.90 (1H, d, J = 5.1 Hz), 7.94 (1H, brd, J = 8.11 Hz), 8.26 (1H, dd, J 1.1, 5.0 Hz), 8.55 (1H, dd, J = 1.1, 4.0 Hz), 8.72 (1H, d, J = 5.1 Hz), 10.16 (1H, s). |
| 300 | (S)- | CH₃, H₃CO-phenyl-CH- | benzo[1,3]dioxol-5-yl | 432.43 | 433 | 1.46 (3H, d, J = 6.9 Hz), 3.73 (3H, s), 4.93 (1H, m), 6.16-0.19 (2H, m), 6.82 (1H, m), 6.90 (1H, m), 6.93 (1H, m), 7.15 (1H, d, J = 8.2 Hz), 7.25 (1H, m), 7.49 (1H, d, J = 4.9 Hz) 7.78 (1H, dd, J = 1.8 & 8.2 Hz), 7.84 (1H, d, J = 1.8 Hz), 8.58 (1H, brd, J = 7.7 Hz), 8.74 (1H, d, J = 4.9 Hz), 10.15 (1H, s). |

TABLE 4-continued

| Example No. | Absolute configuration | Structural formula | | MS: m/z (M + H)+ | Molecular weight | Physicochemical data ¹H-NMR (200 MHz, DMSO-d6): δ |
|---|---|---|---|---|---|---|
| | | R— | Ar— | | | |
| 302 | | CH₃ with H₃CO, H₃CO substituents (1-(3,4,5-trimethoxyphenyl)ethyl) | benzo[1,3]dioxol-5-yl | 493 | 492.48 | 1.47 (3H, d, J = 6.9 Hz), 3.64 (3H, s), 3.74 (6H, s), 4.91 (1H, m), 6.17 (2H, s), 6.68 (2H, s), 7.15 (1H, d, J = 8.3 Hz), 7.50 (1H, d, J = 4.9 Hz), 7.79 (1H, dd, J = 1.8 & 8.2 Hz), 7.85 (1H, d, J = 1.8 Hz), 8.59 (1H, brd, J = 7.9 Hz), 8.74 (1H, d, J = 5.0 Hz), 10.14 (1H, s). |
| 313 | | CH₃, HO, H₃C (6-hydroxy-6-methyl-heptan-2-yl) | 3-(pyridin-3-ylmethoxy)phenyl | 490 | 489.58 | 1.02 (6H, s), 1.12 (3H, d, J = 6.6 Hz), 1.2~1.5 (6H, m), 3.79 (1H, m), 4.06 (1H, s), 5.28 (2H, s), 7.35 (1H, m), 7.46 (1H, dd, J = 4.8 & 7.9 Hz), 8.03 (1H, brd, J = 7.8 Hz), 8.58 (1H, m), 8.74 (1H, m), 8.79 (1H, d, J = 4.8 Hz), 10.07 (1H, s). |
| 317 | | CH₃, HO, H₃C (6-hydroxy-6-methyl-heptan-2-yl) | 4-methoxyphenyl (OCH₃) | 399 | 398.47 | 1.05 (6H, s), 1.15 (3H, d, J = 6.4 Hz), 1.3~1.6 (4H, overlapped), 3.76 (1H, m), 3.89 (3H, s), 4.15 (1H, s), 7.19 (2H, m), 7.49 (1H, d, J = 5.0 Hz), 8.02 (1H, brd, J = 8.0 Hz), 8.23 (2H, m), 8.73 (1H, d, J = 5.0 Hz), 10.01 (1H, s). |
| 319 | (S)- | CH₃, HO, H₃C (6-hydroxy-6-methyl-heptan-2-yl) | 4-methoxyphenyl (OCH₃) | 413 | 412.50 | 1.02 (3H, s), 1.05 (3H, s), 1.15 (3H, d, J = 6.6 Hz), 1.2~1.6 (6H, overlapped), 3.79 (1H, m), 3.89 (3H, s), 4.07 (1H, s), 7.18 (2H, m), 7.49 (1H, d, J = 4.9 Hz), 8.02 (1H, brd, J = 7.7 Hz), 8.22 (2H, m), 8.73 (1H, d, J 4.9 Hz), 10.02 (1H, s). |

TABLE 4-continued

| Example No. | Absolute configuration | Structural formula R— | Ar— | Molecular weight | MS: m/z (M + H)+ | Physicochemical data 1H-NMR (200 MHz, DMSO-d6): δ |
|---|---|---|---|---|---|---|
| 327 | | CH₃ group with H₃C-O-CH₂-CH₂- chain bearing CH₃ | benzo[1,3]dioxole (3,4-methylenedioxyphenyl) | 398.42 | 399 | 1.06 (3H, t, J = 7.0 Hz), 1.17 (3H, d, J = 6.6 Hz), 1.72 (2H, q, J = 6.6 Hz), 3.3~3.5 (4H, m), 3.90 (1H, m), 6.19 (2H, s), 7.18 (1H, d, J = 8.1 Hz), 7.48 (1H, d, J = 4.9 Hz), 7.78 (1H, dd, J = 1.8 & 8.2 Hz), 7.83 (1H, d, J = 1.8 Hz), 8.05 (1H, brd, J = 8.0 Hz), 8.73 (1H, d, J = 4.9 Hz), 10.03 (1H, s). |
| 337 | (S)- | CH₃ with (CH₃)₂C(OH)- group | 4-OCH₃-phenyl | 398.47 | 399 | 1.05 (6H, s), 1.15 (3H, d, J = 6.4 Hz), 1.3~1.6 (4H, overlapped), 3.76 (1H, m), 3.89 (3H, s), 4.15 (1H, s), 7.19 (2H, m), 7.49 (1H, d, J = 5.0 Hz), 8.02 (1H, brd, J = 8.0 Hz), 8.23 (2H, m), 8.73 (1H, d, J = 5.0 Hz), 10.01 (1H, s). |

TABLE 5

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 002 | | H3C-NH-C(=S)- | 2-thienyl | 290.37 | 291 |
| 003 | | Ph-NH-C(=S)- | 2-thienyl | 352.44 | 353 |
| 004 | | PhCH2-NH-C(=O)- | 2-thienyl | 350.40 | 351 |
| 005 | | 3-(H3C-C(=O))-C6H4-NH-C(=O)- | 2-thienyl | 378.41 | 379 |
| 006 | | 4-(H3C-C(=O))-C6H4-NH-C(=O)- | 2-thienyl | 378.41 | 379 |
| 007 | | cyclohexyl-NH-C(=O)- | 2-thienyl | 342.42 | 343 |
| 008 | | 3-(H3CO)-C6H4-NH-C(=O)- | 2-thienyl | 366.40 | 367 |
| 009 | | 4-(H3CO)-C6H4-NH-C(=O)- | 2-thienyl | 366.40 | 367 |
| 010 | | 2-(H3CO)-C6H4-NH-C(=O)- | 2-thienyl | 366.40 | 367 |

TABLE 5-continued
Structural formula
| Example No. | Absolute configuration | R | Ar | Molecular weight | MS: m/z (M + H)+ |
|---|---|---|---|---|---|
| 012 | | 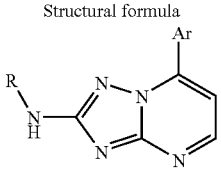 |  | 360.37 | 361 |
| 013 | | 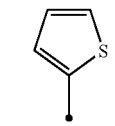 |  | 274.30 | 275 |
| 014 | | 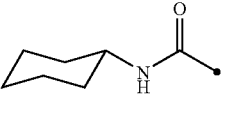 |  | 336.39 | 337 |
| 016 | | 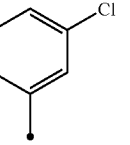 |  | 370.84 | 371 |
| 017 | | 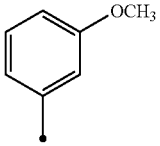 |  | 366.42 | 367 |
| 018 | | 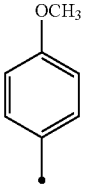 |  | 374.40 | 375 |
| 019 | | 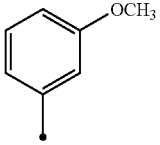 |  | 374.40 | 375 |
| 021 | | 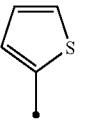 | | 352.37 | 353 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 022 | | 3-HO-C6H4-NH-C(O)-CH< | 2-thienyl | 352.37 | 353 |
| 023 | | 4-HO-C6H4-NH-C(O)-CH< | 2-thienyl | 352.37 | 353 |
| 024 | | cyclohexyl-NH-C(O)-CH< | 4-HO-C6H4- | 352.39 | 353 |
| 025 | | benzyl-NH-C(O)-CH< | 3-HO-C6H4- | 360.37 | 361 |
| 026 | | H3C-NH-C(O)-CH< | 4-CH3O-C6H4- | 298.30 | 299 |
| 027 | | cyclopentyl-NH-C(O)-CH< | 4-CH3O-C6H4- | 352.39 | 353 |
| 028 | | cyclopentyl-NH-C(O)-CH< | 2-thienyl | 328.39 | 329 |

TABLE 5-continued

Structural formula

| Example No. | Absolute configuration | R | Ar | Molecular weight | Physicochemical data MS: m/z (M + H)+ |
|---|---|---|---|---|---|
| 031 | | H₃C-CH₂-NH-C(O)- | 4-OCH₃-C₆H₄- | 312.33 | 313 |
| 032 | | H₃C-CH₂-CH₂-CH₂-NH-C(O)- | 4-OCH₃-C₆H₄- | 340.38 | 341 |
| 033 | | 1-adamantyl-NH-C(O)- | 2-thienyl | 394.49 | 395 |
| 034 | | (H₃C)₃C-CH₂-C(CH₃)₂-NH-C(O)- | 2-thienyl | 372.49 | 373 |
| 035 | | 1-adamantyl-NH-C(O)- | 4-OCH₃-C₆H₄- | 418.49 | 419 |
| 036 | | (H₃C)₃C-CH₂-C(CH₃)₂-NH-C(O)- | 4-OCH₃-C₆H₄- | 396.49 | 397 |
| 038 | | morpholino-NH-C(O)- | 4-OCH₃-C₆H₄- | 369.38 | 370 |

TABLE 5-continued

| Example No. | Absolute configuration | R | Ar | Molecular weight | MS: m/z (M + H)+ |
|---|---|---|---|---|---|
| 040 | | tetrahydrofuran-2-yl-CH2-NH-C(O)- | 4-OCH3-C6H4- | 368.39 | 369 |
| 041 | | tetrahydrofuran-2-yl-CH2-NH-C(O)- | thiophen-2-yl | 344.39 | 345 |
| 042 | | (CH3)2N-CH2CH2-NH-C(O)- | 4-OCH3-C6H4- | 355.39 | 356 |
| 043 | | cyclopentyl-NH-C(O)- | 3-OCH3-C6H4- | 352.39 | 353 |
| 046 | | (CH3)2CH-NH-C(O)- | 2,3-dihydrobenzofuran-5-yl | 338.36 | 339 |
| 047 | | cyclohexyl-NH-C(O)- | 2,3-dihydrobenzofuran-5-yl | 378.43 | 379 |
| 048 | | (CH3)2CH-NH-C(O)- | 3-Cl-C6H4- | 330.77 | 331 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 050 | (S)- | tert-butyl N-acetyl-alaninate | 2-thienyl | 388.44 | 389 |
| 052 | (R)- | tert-butyl N-acetyl-alaninate | 2-thienyl | 388.44 | 389 |
| 057 | (S)- | N-(2-dimethylaminoethyl)-N'-acetyl-valinamide | 4-methoxyphenyl | 454.53 | 455 |
| 060 | | N-(pyridin-2-yl)acetamide | 4-methoxyphenyl | 361.36 | 362 |
| 061 | | N-(pyridin-3-yl)acetamide | 4-methoxyphenyl | 361.36 | 362 |
| 062 | | N-(pyridin-4-yl)acetamide | 4-methoxyphenyl | 361.36 | 362 |
| 064 | | N-(2-morpholinoethyl)acetamide | 4-methoxyphenyl | 397.43 | 398 |

TABLE 5-continued
| Example No. | Absolute configuration | R | Ar | Molecular weight | MS: m/z (M + H)+ |
|---|---|---|---|---|---|
| 065 | | 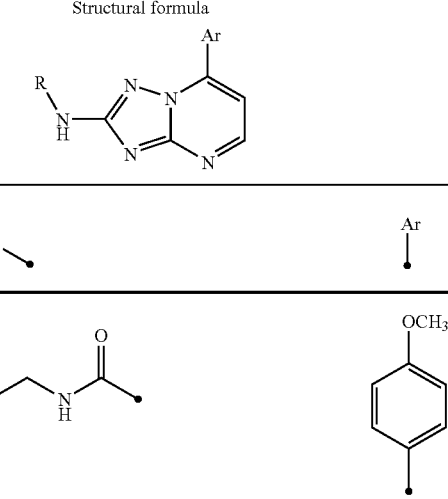 | 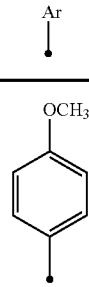 | 389.41 | 390 |
| 066 | | 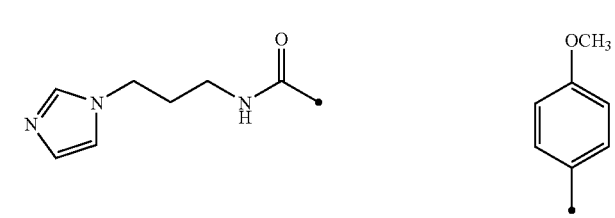 | 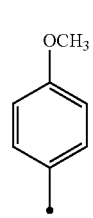 | 392.41 | 393 |
| 068 | | 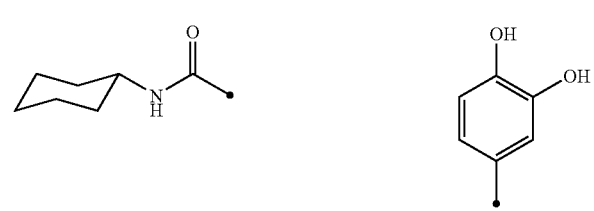 | 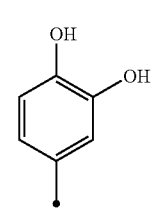 | 368.39 | 369 |
| 070 | (S)- | 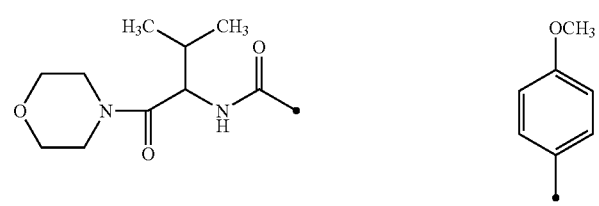 | 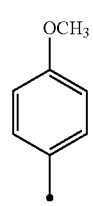 | 453.49 | 454 |
| 071 | | 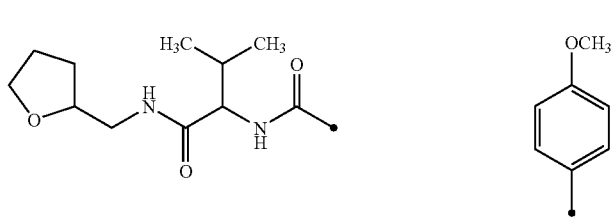 | 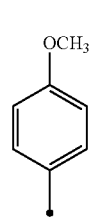 | 467.52 | 468 |
| 073 | (S)- | 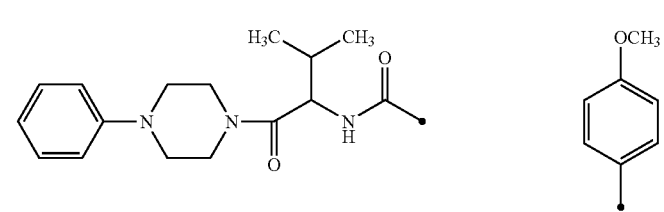 | 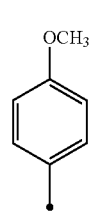 | 528.61 | 529 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 074 | (S)- | 1-benzylpiperidin-4-yl-NH-C(=O)-CH(iPr)-NH-C(=O)- | 4-OCH₃-C₆H₄- | 556.66 | 557 |
| 075 | (S)- | pyridin-2-yl-NH-C(=O)-CH(iPr)-NH-C(=O)- | 4-OCH₃-C₆H₄- | 460.49 | 461 |
| 076 | (S)- | pyridin-4-yl-NH-C(=O)-CH(iPr)-NH-C(=O)- | 4-OCH₃-C₆H₄- | 460.49 | 461 |
| 077 | (S)- | benzyl-NH-C(=O)-CH(iPr)-NH-C(=O)- | 4-OCH₃-C₆H₄- | 474.52 | 475 |
| 078 | (S)- | (pyridin-3-yl)methyl-NH-C(=O)-CH(iPr)-NH-C(=O)- | 4-OCH₃-C₆H₄- | 474.52 | 475 |
| 079 | (S)- | morpholin-4-yl-CH₂CH₂-NH-C(=O)-CH(iPr)-NH-C(=O)- | 4-OCH₃-C₆H₄- | 496.56 | 497 |

TABLE 5-continued
Structural formula
| Example No. | Absolute configuration | R | Ar | Molecular weight | Physicochemical data MS: m/z (M + H)+ |
|---|---|---|---|---|---|
| 080 | (S)- |  | 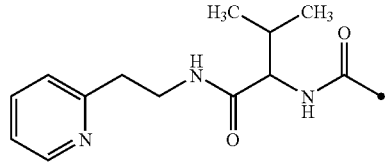 | 488.54 | 489 |
| 081 | (S)- |  | 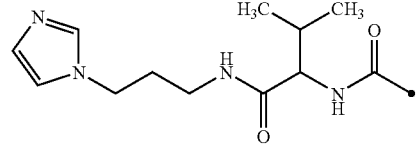 | 491.55 | 492 |
| 082 | (S)- |  | 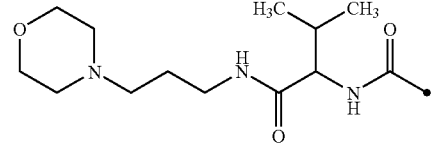 | 510.59 | 511 |
| 083 | | 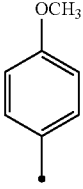 | 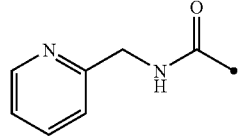 | 375.38 | 376 |
| 085 | | 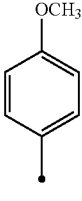 | 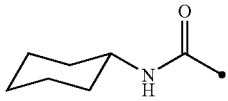 | 352.39 | 353 |
| 086 | | 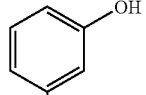 | 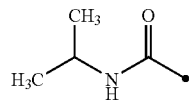 | 356.38 | 357 |
| 087 | | 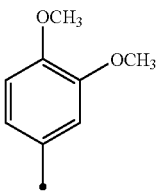 | 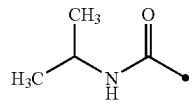 | 340.34 | 341 |

TABLE 5-continued
Structural formula
| Example No. | Absolute configuration | R | Ar | Molecular weight | MS: m/z (M + H)+ |
|---|---|---|---|---|---|
| 088 | (S)- |  | 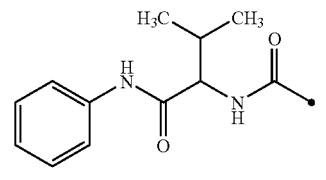 | 459.50 | 460 |
| 089 | (S)- | 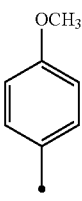 | 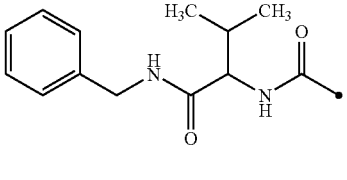 | 473.53 | 474 |
| 090 | (S)- |  | 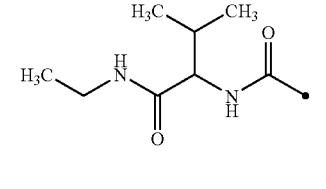 | 411.46 | 412 |
| 091 | (S)- | 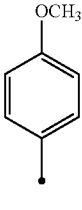 | 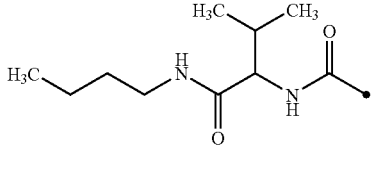 | 439.51 | 440 |
| 092 | (S)- | 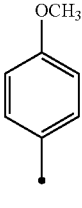 | 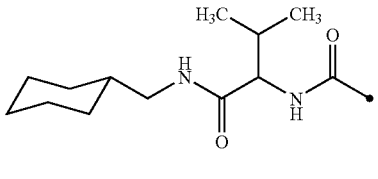 | 479.57 | 480 |
| 093 | (S)- |  | 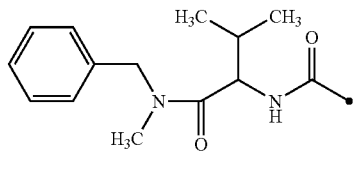 | 487.55 | 488 |

TABLE 5-continued
Structural formula
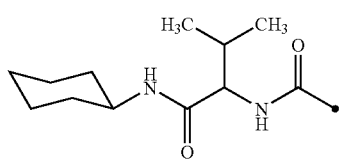
| Example No. | Absolute configuration | R | Ar | Molecular weight | MS: m/z (M + H)+ |
|---|---|---|---|---|---|
| 094 | (S)- | 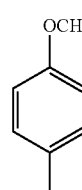 | 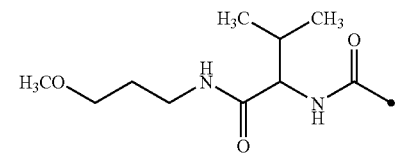 | 465.55 | 466 |
| 095 | (S)- | 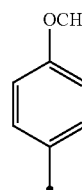 | 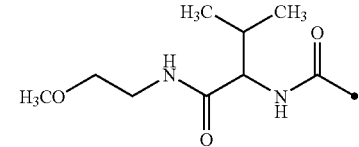 | 455.51 | 456 |
| 096 | (S)- | 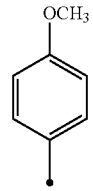 | 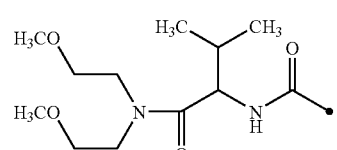 | 441.48 | 442 |
| 097 | (S)- | 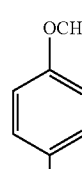 | 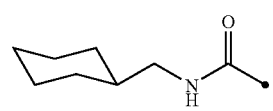 | 499.56 | 500 |
| 099 | | 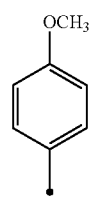 | 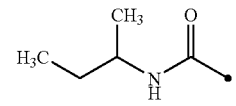 | 380.44 | 381 |
| 100 | | 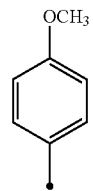 | | 340.38 | 341 |

TABLE 5-continued

| Example No. | Absolute configuration | R | Ar | Molecular weight | MS: m/z (M + H)+ |
|---|---|---|---|---|---|
| 103 | | 4-pyridylmethyl-NHC(O)CH2– | 4-OCH3-C6H4– | 375.38 | 376 |
| 104 | | 3-pyridyl-(CH2)2-NHC(O)CH2– | 4-OCH3-C6H4– | 389.41 | 390 |
| 105 | | 4-pyridyl-(CH2)2-NHC(O)CH2– | 4-OCH3-C6H4– | 389.41 | 390 |
| 106 | | H3CO-(CH2)3-NHC(O)CH2– | 4-OCH3-C6H4– | 356.38 | 357 |
| 107 | | 2-oxotetrahydrofuran-3-yl-NHC(O)CH2– | 4-OCH3-C6H4– | 368.35 | 369 |
| 110 | | (CH3)3C-O-C(O)-CH2-NHC(O)CH2– | 4-OCH3-C6H4– | 398.42 | 399 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 111 | | tert-butyl 2-methyl-2-(acetamido)propanoate group | OCH₃-phenyl | 426.47 | 427 |
| 112 | (S)- | tert-butyl 2-(acetamido)-3-phenylpropanoate group | OCH₃-phenyl | 488.54 | 489 |
| 113 | | methyl 2-(acetamido)acetate group | OCH₃-phenyl | 356.34 | 357 |
| 114 | | benzyl 2-(acetamido)acetate group | OCH₃-phenyl | 432.43 | 433 |
| 116 | (S)- | N-(2-(pyridin-4-yl)ethyl)-2-(acetamido)-3-methylbutanamide group | OCH₃-phenyl | 488.54 | 489 |
| 119 | (S)- | N-benzyl-2-(acetamido)propanamide group | OCH₃-phenyl | 445.47 | 446 |

TABLE 5-continued
Structural formula
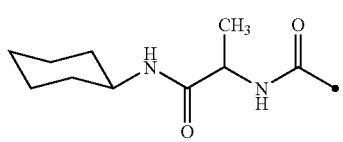
| Example No. | Absolute configuration | R | Ar | Molecular weight | MS: m/z (M + H)+ |
|---|---|---|---|---|---|
| 120 | (S)- | 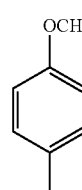 | 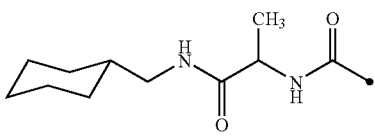 | 437.49 | 438 |
| 121 | (S)- | 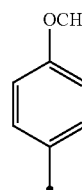 | 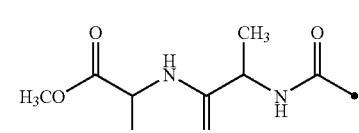 | 451.52 | 452 |
| 122 | (S, S)- | 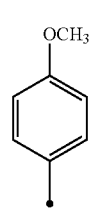 | 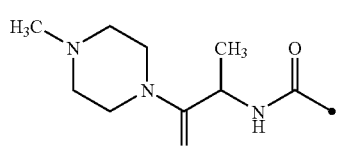 | 441.44 | 442 |
| 123 | (S)- | 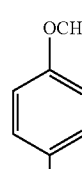 | 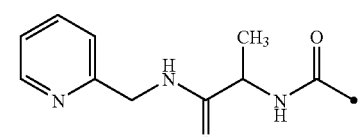 | 438.48 | 439 |
| 124 | (S)- | 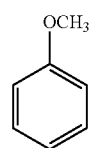 | 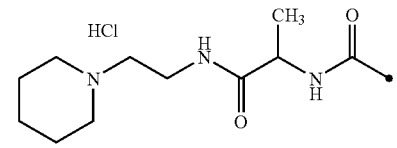 | 446.46 | 447 |
| 125 | (S)- | 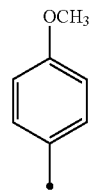 | | 503.00 | 467 |

TABLE 5-continued
Structural formula
| Example No. | Absolute configuration | R | Ar | Molecular weight | MS: m/z (M + H)+ |
|---|---|---|---|---|---|
| 126 | (R)- |  | 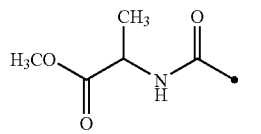 | 370.36 | 371 |
| 127 | (S)- | 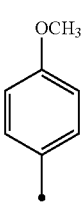 | 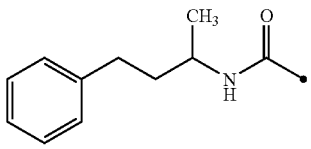 | 416.48 | 417 |
| 128 | |  | 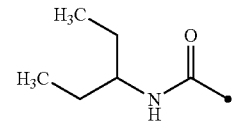 | 354.41 | 355 |
| 129 | (S)- | 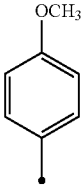 | 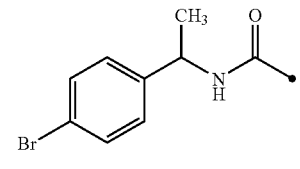 | 467.32 | 468 |
| 130 | (S)- | 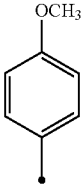 | 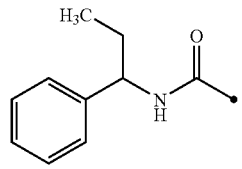 | 402.45 | 403 |
| 131 | (S)- | 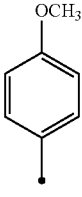 | 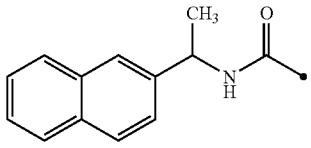 | 438.48 | 439 |

TABLE 5-continued
| Example No. | Absolute configuration | R | Ar | Molecular weight | Physicochemical data MS: m/z (M + H)+ |
|---|---|---|---|---|---|
| 132 | (S)- |  | 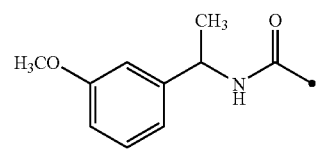 | 418.45 | 419 |
| 134 | (S)- | 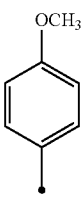 | 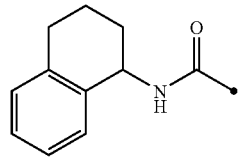 | 414.46 | 415 |
| 135 | (S)- |  | 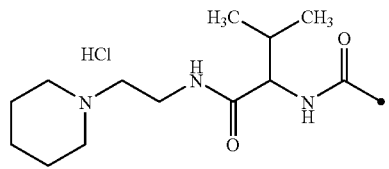 | 531.05 | 495 |
| 136 | | 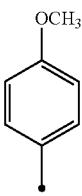 | 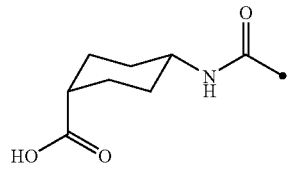 | 410.43 | 411 |
| 137 | | 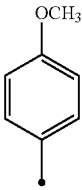 | 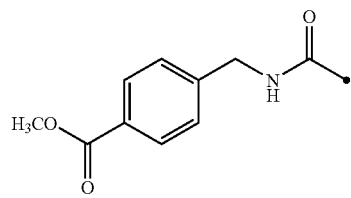 | 432.43 | 433 |
| 138 | | 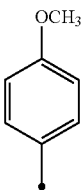 | 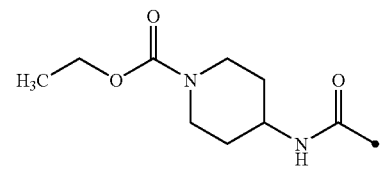 | 439.47 | 440 |

TABLE 5-continued
| Example No. | Absolute configuration | R | Ar | Molecular weight | Physicochemical data MS: m/z (M + H)+ |
|---|---|---|---|---|---|
| 139 | (S)- |  | 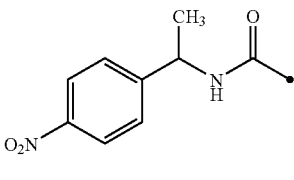 | 433.42 | 434 |
| 140 | | 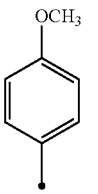 | 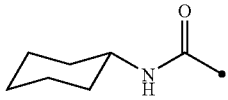 | 459.97 | 424 |
| 141 | | 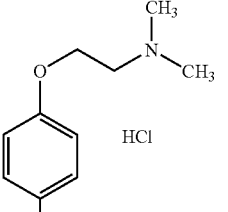 | 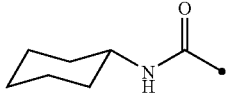 | 459.97 | 424 |
| 142 | | 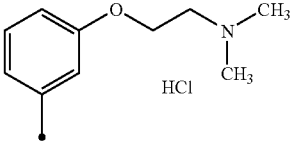 | 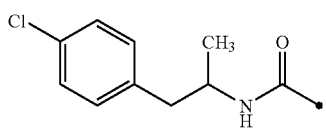 | 436.89 | 437 |
| 143 | | 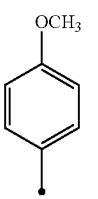 | 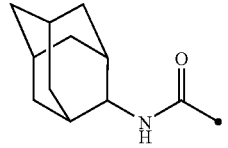 | 418.49 | 419 |
| 144 | | 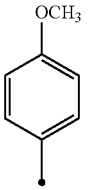 | 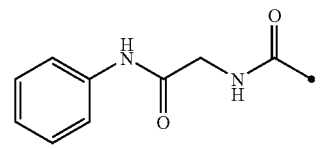 | 417.42 | 418 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 145 |  | morpholine-N-C(O)-CH2-NH-C(O)-CH2-* | 4-OCH3-C6H4- | 411.41 | 412 |
| 146 |  | (tetrahydrofuran-2-yl)-CH2-NH-C(O)-CH2-NH-C(O)-CH2-* | 4-OCH3-C6H4- | 425.44 | 426 |
| 147 | (S)- | H3CO-C(O)-CH(CH3)-NH-C(O)-CH2-NH-C(O)-CH2-* | 4-OCH3-C6H4- | 427.41 | 428 |
| 148 | (S)- | Ph-NH-C(O)-CH(CH2CH3)-NH-C(O)-CH2-* | 4-OCH3-C6H4- | 445.47 | 446 |
| 149 | (S)- | morpholine-N-C(O)-CH(CH2CH3)-NH-C(O)-CH2-* | 4-OCH3-C6H4- | 439.47 | 440 |
| 150 | (S)- | H3CO-C(O)-CH(CH3)-NH-C(O)-CH(CH2CH3)-NH-C(O)-CH2-* | 4-OCH3-C6H4- | 455.47 | 456 |

TABLE 5-continued

| Example No. | Absolute configuration | R | Ar | Molecular weight | MS: m/z (M + H)+ |
|---|---|---|---|---|---|
| 151 | (S)- | CH₃, phenyl-NH-C(O)-CH(propyl)-NH-C(O)- | 4-OCH₃-phenyl | 459.50 | 460 |
| 152 | (S)- | morpholino-C(O)-CH(propyl)-NH-C(O)- | 4-OCH₃-phenyl | 453.49 | 454 |
| 153 | (S, S)- | H₃CO-C(O)-CH(CH₃)-NH-C(O)-CH(propyl)-NH-C(O)- | 4-OCH₃-phenyl | 469.49 | 470 |
| 154 | (S)- | phenyl-NH-C(O)-CH₂-CH(CH₃)-NH-C(O)- | 4-OCH₃-phenyl | 445.47 | 446 |
| 155 | (S)- | morpholino-C(O)-CH₂-CH(CH₃)-NH-C(O)- | 4-OCH₃-phenyl | 439.47 | 440 |
| 156 | | phenyl-NH-C(O)-CH₂-CH₂-NH-C(O)- | 4-OCH₃-phenyl | 431.45 | 432 |

TABLE 5-continued

| Example No. | Absolute configuration | R | Ar | Molecular weight | MS: m/z (M + H)+ |
|---|---|---|---|---|---|
| 157 | | morpholine-C(O)-CH2CH2-NH-C(O)- | 4-OCH3-C6H4- | 425.44 | 426 |
| 158 | | (tetrahydrofuran-2-yl)CH2-NH-C(O)-CH2CH2-NH-C(O)- | 4-OCH3-C6H4- | 439.47 | 440 |
| 159 | (S)- | (H3C-CH2)2N-CH2CH2CH2-CH(CH3)-NH-C(O)- | 4-OCH3-C6H4- | 425.53 | 426 |
| 161 | | 3-HOOC-cyclohexyl-NH-C(O)- | 4-OCH3-C6H4- | 410.43 | 411 |
| 162 | (S)- | Ph-CH(CH3)-NH-C(O)- | 3-OCH3-C6H4- | 388.42 | 389 |
| 163 | | morpholine-CH2CH2CH2-NH-C(O)- | 3-OCH3-C6H4- | 411.46 | 412 |
| 164 | | morpholine-CH2CH2CH2-NH-C(O)- | 3-Cl-C6H4- | 415.88 | 416 |

TABLE 5-continued
Structural formula:
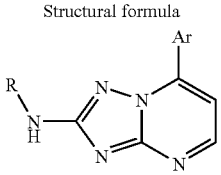
| Example No. | Absolute configuration | R | Ar | Molecular weight | MS: m/z (M + H)+ |
|---|---|---|---|---|---|
| 166 | |  | 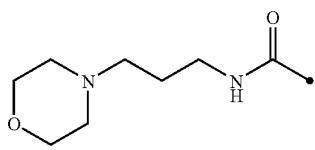 | 387.46 | 388 |
| 167 | | 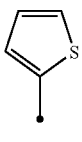 |  | 424.45 | 425 |
| 168 | | 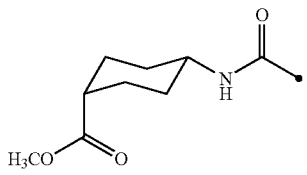 | 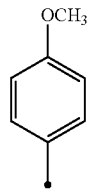 | 424.45 | 425 |
| 169 | |  | 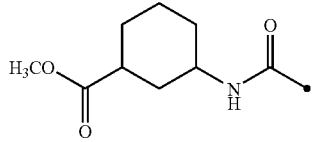 | 437.49 | 438 |
| 170 | | 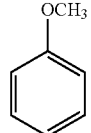 |  | 443.50 | 444 |
| 171 | | 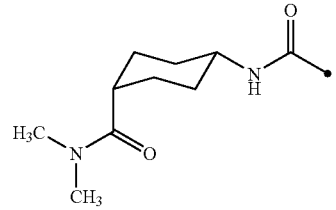 | 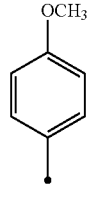 | 443.50 | 444 |

TABLE 5-continued
Structural formula
| Example No. | Absolute configuration | R | Ar | Molecular weight | Physicochemical data MS: m/z (M + H)+ |
|---|---|---|---|---|---|
| 173 | (S)- |  | 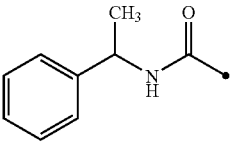 | 359.38 | 360 |
| 174 | | 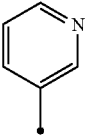 | 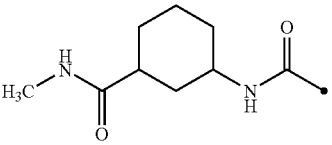 | 423.47 | 424 |
| 175 | | 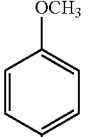 | 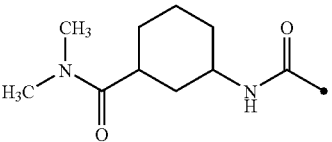 | 437.49 | 438 |
| 176 | (S)- | 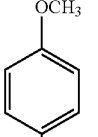 | 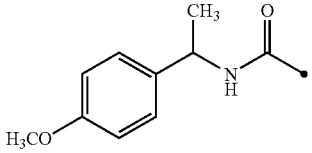 | 394.45 | 395 |
| 177 | | 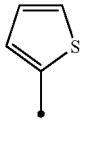 | 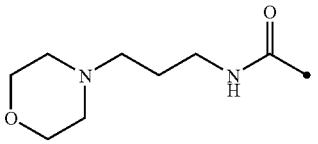 | 382.42 | 383 |
| 178 | | 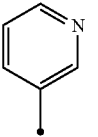 | 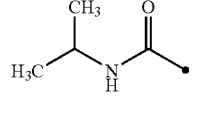 | 297.32 | 298 |
| 179 | (S)- | 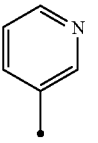 | 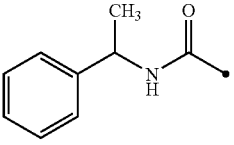 | 359.38 | 360 |
| 180 | | 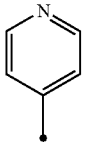 | 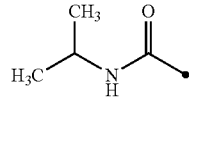 | 416.48 | 417 |

TABLE 5-continued
Structural formula
| Example No. | Absolute configuration | R | Ar | Molecular weight | MS: m/z (M + H)+ |
|---|---|---|---|---|---|
| 181 | (S)- |  | 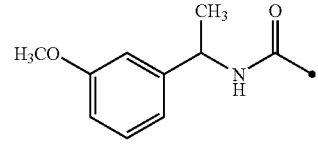 | 394.45 | 395 |
| 182 | (S)- | 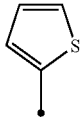 | 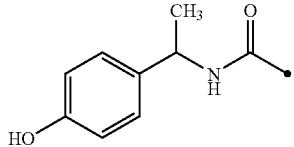 | 380.42 | 381 |
| 183 | | 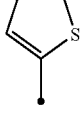 | 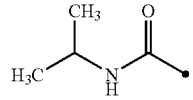 | 426.47 | 427 |
| 185 | | 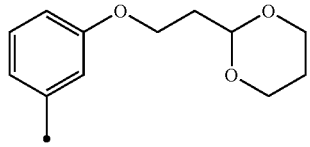 | 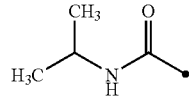 | 403.44 | 404 |
| 186 | (S)- | 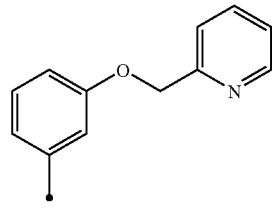 | 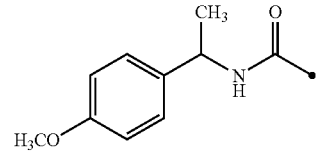 | 418.45 | 419 |
| 187 | (S)- | 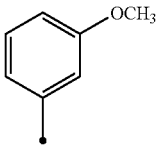 | 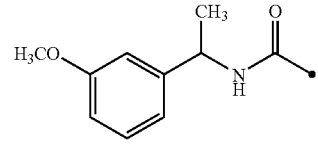 | 418.45 | 419 |
| 188 | (S)- | 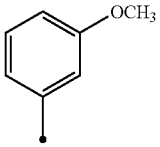 | 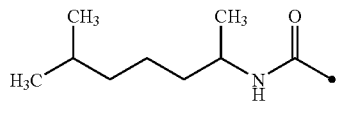 | 396.49 | 397 |

TABLE 5-continued

Structural formula

| Example No. | Absolute configuration | R | Ar | Molecular weight | MS: m/z (M + H)+ |
|---|---|---|---|---|---|
| 189 | | isopropyl-NH-C(=O)-CH< | 3-(2-morpholinoethoxy)phenyl | 425.48 | 426 |
| 190 | | isopropyl-NH-C(=O)-CH< | 3-(2-piperidinoethoxy)phenyl | 423.51 | 424 |
| 191 | | isopropyl-NH-C(=O)-CH< | 3-(2-dimethylaminoethoxy)phenyl | 383.45 | 384 |
| 192 | | isopropyl-NH-C(=O)-CH< | 3-(3-dimethylaminopropoxy)phenyl | 397.47 | 398 |
| 193 | | isopropyl-NH-C(=O)-CH< | 3-(pyridin-4-ylmethoxy)phenyl | 403.44 | 404 |
| 194 | | isopropyl-NH-C(=O)-CH< | 3-(3-phenylpropoxy)phenyl | 430.50 | 431 |
| 195 | | 3-(methanesulfonyloxy)phenyl-CH(CH3)-NH-C(=O)-CH< | 4-methoxyphenyl | 482.51 | 483 |

TABLE 5-continued
Structural formula
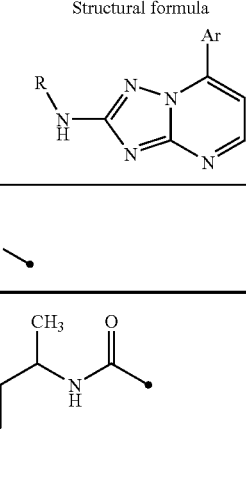
| Example No. | Absolute configuration | R | Ar | Molecular weight | MS: m/z (M + H)+ |
|---|---|---|---|---|---|
| 196 | | 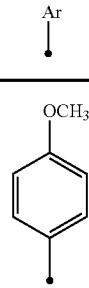 | 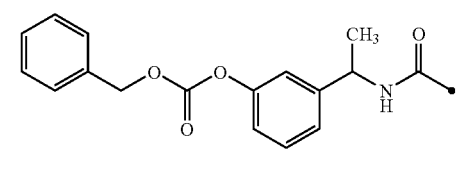 | 404.42 | 405 |
| 197 | | 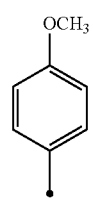 | 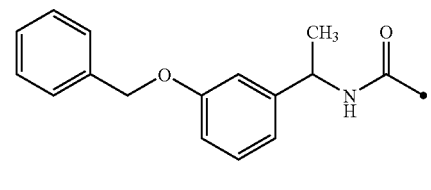 | 538.55 | 539 |
| 198 | | 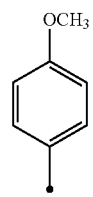 | 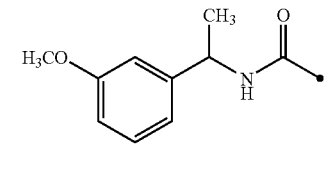 | 494.54 | 495 |
| 199 | (S)- | 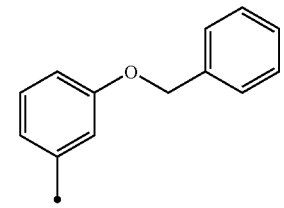 | 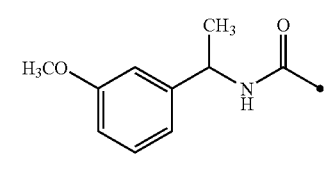 | 494.54 | 495 |
| 200 | (S)- | 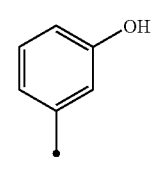 | 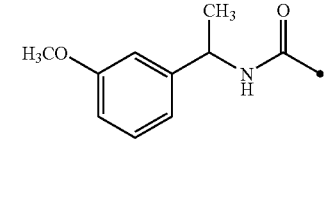 | 404.42 | 405 |
| 201 | (S)- | 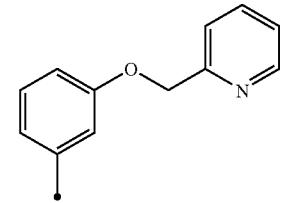 | | 495.53 | 496 |

TABLE 5-continued

Structural formula

| Example No. | Absolute configuration | R | Ar | Molecular weight | Physicochemical data MS: m/z (M + H)+ |
|---|---|---|---|---|---|
| 202 | (S)- | H3CO-C6H4-CH(CH3)-NH-C(O)- | 3-(pyridin-3-ylmethoxy)phenyl | 495.53 | 496 |
| 203 | (S)- | H3CO-C6H4-CH(CH3)-NH-C(O)- | 3-(pyridin-4-ylmethoxy)phenyl | 495.53 | 496 |
| 205 | (S)- | H3CO-C6H4-CH(CH3)-NH-C(O)- | 3-(2-(dimethylamino)ethoxy)phenyl | 475.54 | 476 |
| 206 | (S)- | H3CO-C6H4-CH(CH3)-NH-C(O)- | 3-((tetrahydrofuran-2-yl)methoxy)phenyl | 488.54 | 489 |
| 207 | (S)- | H3CO-C6H4-CH(CH3)-NH-C(O)- | 3-(2-(1,3-dioxan-2-yl)ethoxy)phenyl | 518.56 | 519 |
| 208 | (S)- | H3CO-C6H4-CH(CH3)-NH-C(O)- | 3-(2-(pyridin-2-yl)ethoxy)phenyl | 509.56 | 510 |
| 209 | (S)- | H3CO-C6H4-CH(CH3)-NH-C(O)- | 3-(2-(pyridin-4-yl)ethoxy)phenyl | 509.56 | 510 |

TABLE 5-continued
Structural formula
| Example No. | Absolute configuration | R | Ar | Molecular weight | MS: m/z (M + H)+ |
|---|---|---|---|---|---|
| 210 | (S)- |  | 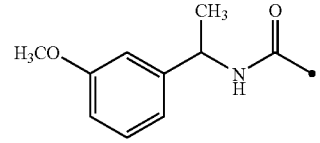 | 523.59 | 524 |
| 211 | (S)- | 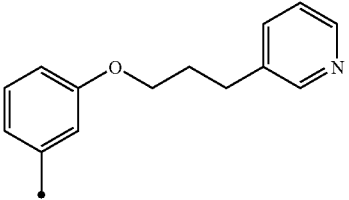 | 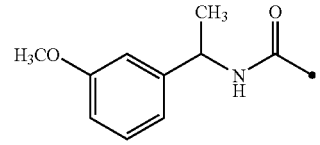 | 523.59 | 524 |
| 212 | (S)- | 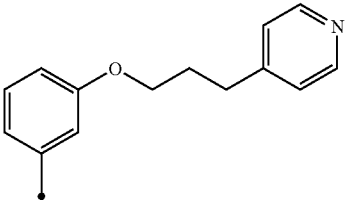 | 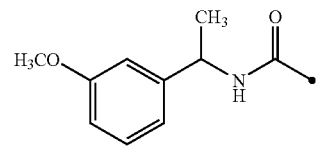 | 448.47 | 449 |
| 213 | (S)- | 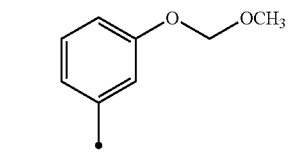 | 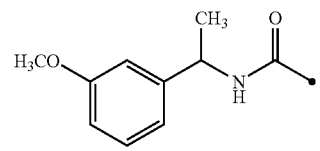 | 492.53 | 493 |
| 214 | | 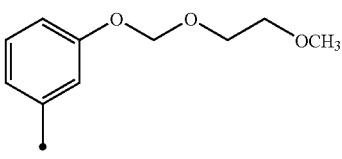 | 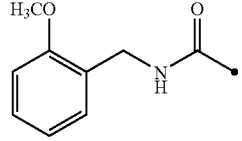 | 404.42 | 405 |
| 215 | | 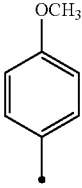 | 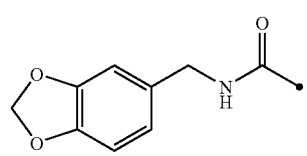 | 418.41 | 419 |
| 216 | (S)- | 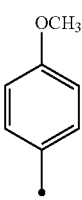 | 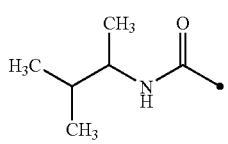 | 354.41 | 355 |

TABLE 5-continued
Structural formula
| Example No. | Absolute configuration | R | Ar | Molecular weight | Physicochemical data MS: m/z (M + H)+ |
|---|---|---|---|---|---|
| 217 | (S)- |  | 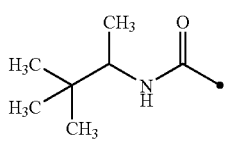 | 368.43 | 369 |
| 218 | (S)- |  | 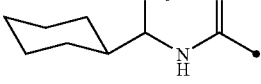 | 394.47 | 395 |
| 219 | | 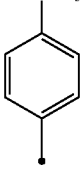 | 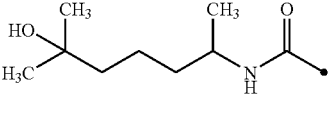 | 412.49 | 413 |
| 220 | (S)- |  | 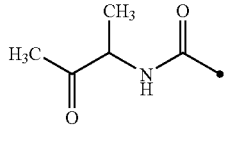 | 354.36 | 355 |
| 221 | (S)- |  | 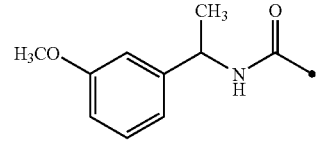 | 489.57 | 490 |
| 222 | (S)- | 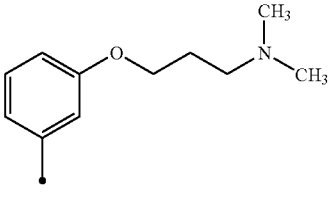 | 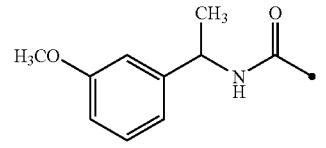 | 494.54 | 495 |

TABLE 5-continued

Structural formula: Ar-[7-position of R-NH-[1,2,4]triazolo[1,5-a]pyrimidin-2-yl]

| Example No. | Absolute configuration | R | Ar | Molecular weight | MS: m/z (M + H)+ |
|---|---|---|---|---|---|
| 223 | (S)- | 1-(3-methoxyphenyl)ethyl-NH-C(O)-CH2- | 4-hydroxyphenyl | 404.42 | 405 |
| 224 | (S)- | 1-(3-methoxyphenyl)ethyl-NH-C(O)-CH2- | 4-(tetrahydrofuran-2-ylmethoxy)phenyl | 488.54 | 489 |
| 225 | (S)- | 1-(3-methoxyphenyl)ethyl-NH-C(O)-CH2- | 4-[2-(1,3-dioxan-2-yl)ethoxy]phenyl | 518.56 | 519 |
| 226 | (S)- | 1-(3-methoxyphenyl)ethyl-NH-C(O)-CH2- | 4-(methoxymethoxy)phenyl | 448.47 | 449 |
| 227 | (S)- | 1-(3-methoxyphenyl)ethyl-NH-C(O)-CH2- | 4-[(2-methoxyethoxy)methoxy]phenyl | 492.53 | 493 |
| 228 | (S)- | 1-(3-methoxyphenyl)ethyl-NH-C(O)-CH2- | 4-(methoxycarbonylmethoxy)phenyl | 476.48 | 477 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)⁺ |
|---|---|---|---|---|---|
| 229 | (S)- | 1-(3-methoxyphenyl)ethyl-NH-C(=O)-CH₃ | 4-(carboxymethoxy)phenyl | 462.46 | 463 |
| 230 | | 1-(3-isobutoxyphenyl)ethyl-NH-C(=O)- | 4-methoxyphenyl | 460.53 | 461 |
| 231 | | 1-(3-isopropoxyphenyl)ethyl-NH-C(=O)- | 4-methoxyphenyl | 446.50 | 447 |
| 232 | (S)- | 1-(3-methoxyphenyl)ethyl-NH-C(=O)- | 4-(dimethylamino)phenyl | 431.49 | 432 |
| 233 | (S)- | 1-methyl-5-methoxypentyl-NH-C(=O)- | 4-methoxyphenyl | 398.46 | 399 |
| 234 | (S)- | sec-butyl-NH-C(=O)- | 4-methoxyphenyl | 340.38 | 341 |

TABLE 5-continued

| Example No. | Absolute configuration | R | Ar | Molecular weight | MS: m/z (M + H)+ |
|---|---|---|---|---|---|
| 235 | | isobutyl-CH(CH3)-NH-C(=O)- | 4-methoxyphenyl | 368.43 | 369 |
| 236 | | isobutyl-CH2-CH(CH3)-NH-C(=O)- | 4-methoxyphenyl | 382.46 | 383 |
| 238 | (S)- | 3-methoxyphenyl-CH(CH3)-NH-C(=O)- | 4-(2-(2-(2-methoxyethoxy)ethoxy)ethoxy)phenyl | 550.61 | 551 |
| 239 | (S)- | 3-methoxyphenyl-CH(CH3)-NH-C(=O)- | 3-(2-(2-(2-methoxyethoxy)ethoxy)ethoxy)phenyl | 550.61 | 551 |
| 240 | (S)- | 4-methoxyphenyl-CH(CH3)-NH-C(=N-CN)- | 2-thienyl | 418.47 | 419 |
| 241 | (S)- | 4-methoxyphenyl-CH(CH3)-NH-C(=N-CN)- | 4-methoxyphenyl | 442.47 | 443 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 242 | (S)- | H₃CO-C₆H₄-CH(CH₃)-NH-C(O)- | 3-(N(CH₃)₂)-C₆H₄- | 431.49 | 432 |
| 243 | (S)- | H₃CO-C₆H₄-CH(CH₃)-NH-C(O)- | 3-(morpholino)-C₆H₄- | 473.53 | 474 |
| 244 | (S)- | H₃CO-C₆H₄-CH(CH₃)-NH-C(O)- | 4-(OCH₂CH₂OCH₃)-C₆H₄- | 462.50 | 463 |
| 245 | (S)- | (CH₃)₂CH-CH₂-CH₂-CH(CH₃)-NH-C(O)- | 4-(OCH₂C₆H₅)-C₆H₄- | 472.58 | 473 |
| 246 | (S)- | (CH₃)₂CH-CH₂-CH₂-CH(CH₃)-NH-C(O)- | 2-thienyl | 372.49 | 373 |
| 247 | | 3,4,5-(H₃CO)₃-C₆H₂-CH₂-NH-C(O)- | 4-(OCH₃)-C₆H₄- | 464.47 | 465 |

TABLE 5-continued
| Example No. | Absolute configuration | R | Ar | Molecular weight | MS: m/z (M + H)+ |
|---|---|---|---|---|---|
| 248 | (S)- |  |  | 531.61 | 532 |
| 249 | (S)- | 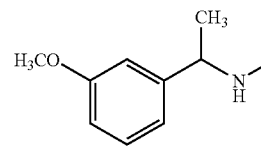 | 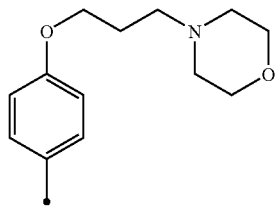 | 531.61 | 532 |
| 250 | (S)- | 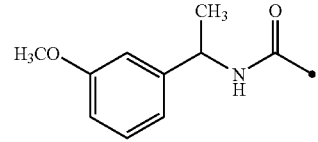 | 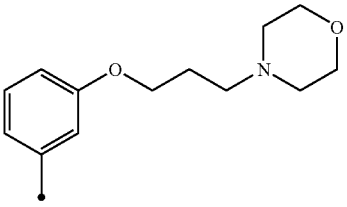 | 420.51 | 421 |
| 251 | (S)- | 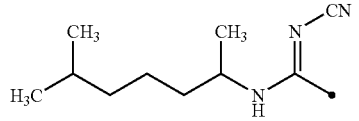 |  | 536.58 | 537 |
| 252 | (S)- | 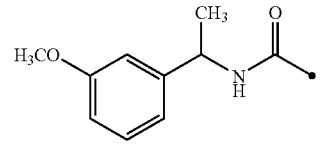 | 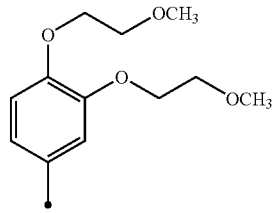 | 514.62 | 515 |
| 253 | (S)- | 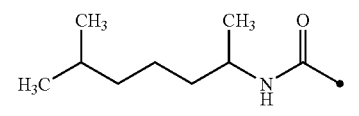 | 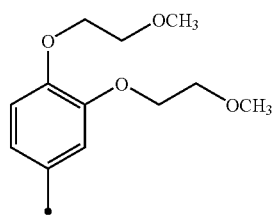 | 531.56 | 532 |

TABLE 5-continued
Structural formula
| Example No. | Absolute configuration | R | Ar | Molecular weight | Physicochemical data MS: m/z (M + H)+ |
|---|---|---|---|---|---|
| 254 | (S)- |  | 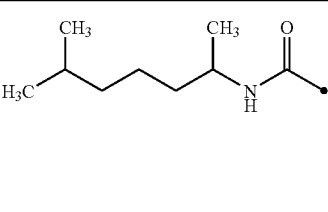 | 472.58 | 473 |
| 255 | (S)- | 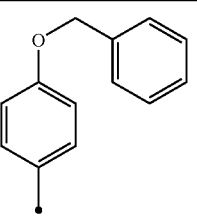 | 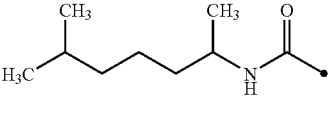 | 382.46 | 383 |
| 256 | (S)- | 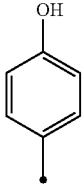 | 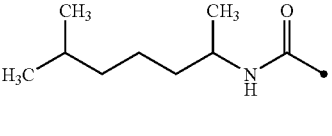 | 472.58 | 473 |
| 257 | (S)- | 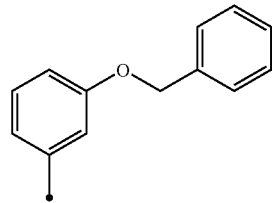 | 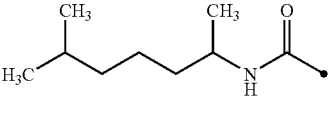 | 382.46 | 383 |
| 258 | (S)- | 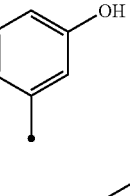 | 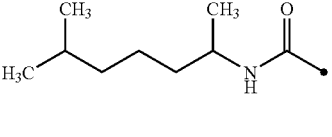 HCl | 532.08 | 496 |
| 259 | (S)- | 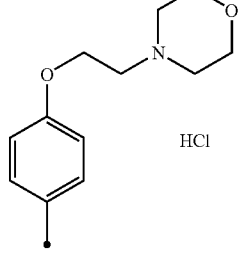 | 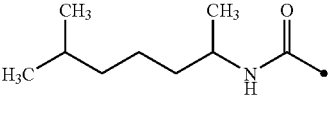 | 495.62 | 496 |

TABLE 5-continued

Structural formula

| Example No. | Absolute configuration | R | Ar | Molecular weight | MS: m/z (M + H)+ |
|---|---|---|---|---|---|
| 260 | (S)- | CH₃-CH(CH₃)-CH₂-CH₂-CH₂-CH(CH₃)-NH-C(=O)- | 3-(tetrahydrofuran-2-ylmethoxy)phenyl | 466.58 | 467 |
| 261 | (S)- | CH₃-CH(CH₃)-CH₂-CH₂-CH₂-CH(CH₃)-NH-C(=O)- | 3-(pyridin-3-ylmethoxy)phenyl | 473.57 | 474 |
| 262 | (S)- | CH₃-CH(CH₃)-CH₂-CH₂-CH₂-CH(CH₃)-NH-C(=O)- | 4-(2-methoxyethoxy)phenyl | 440.54 | 441 |
| 263 | (S)- | CH₃-CH(CH₃)-CH₂-CH₂-CH₂-CH(CH₃)-NH-C(=O)- | 4-(2-(2-(2-methoxyethoxy)ethoxy)ethoxy)phenyl | 528.64 | 529 |
| 264 | (S)- | CH₃-CH(CH₃)-CH₂-CH₂-CH₂-CH(CH₃)-NH-C(=O)- | 3-(2-methoxyethoxy)phenyl | 440.54 | 441 |
| 265 | (S)- | CH₃-CH(CH₃)-CH₂-CH₂-CH₂-CH(CH₃)-NH-C(=O)- | 3-(2-(2-(2-methoxyethoxy)ethoxy)ethoxy)phenyl | 528.64 | 529 |

TABLE 5-continued

Structural formula:

R-NH-[1,2,4]triazolo[1,5-a]pyrimidine-Ar

| Example No. | Absolute configuration | R | Ar | Molecular weight | MS: m/z (M + H)+ |
|---|---|---|---|---|---|
| 266 | (S)- | HO-C6H4-CH(CH3)-NH-C(O)- (3-hydroxyphenyl) | 4-hydroxyphenyl | 390.40 | 391 |
| 267 | (S)- | HO-C6H4-CH(CH3)-NH-C(O)- (3-hydroxyphenyl) | 3-hydroxyphenyl | 390.40 | 391 |
| 268 | (S)- | H3CO-C6H4-CH(CH3)-NH-C(O)- (3-methoxyphenyl) | 4-(1H-tetrazol-5-ylmethoxy)phenyl | 486.49 | 487 |
| 269 | (S)- | H3CO-C6H4-CH(CH3)-NH-C(O)- (3-methoxyphenyl) | 4-(2-morpholinoethoxy)phenyl | 517.58 | 518 |
| 270 | (S)- | H3CO-C6H4-CH(CH3)-NH-C(O)- (3-methoxyphenyl) | 4-(2-(2-(2-hydroxyethoxy)ethoxy)ethoxy)phenyl | 536.58 | 537 |
| 271 | (S)- | HO-C6H4-CH(CH3)-NH-C(O)- (3-hydroxyphenyl) | 4-(2-(2-(2-hydroxyethoxy)ethoxy)ethoxy)phenyl | 522.55 | 523 |

TABLE 5-continued

| Example No. | Absolute configuration | R | Ar | Molecular weight | MS: m/z (M + H)+ |
|---|---|---|---|---|---|
| 273 | | morpholine-C(O)-CH2CH2-CH(CH3)-NH-C(O)- | 4-OCH3-C6H4- | 453.49 | 454 |
| 274 | | H3C-CH2-O-CH2-CH(CH3)-NH-C(O)- | 4-OCH3-C6H4- | 384.43 | 385 |
| 275 | | morpholine-C(O)-CH2CH2CH2-CH(CH3)-NH-C(O)- | 4-OCH3-C6H4- | 467.52 | 468 |
| 276 | | H3C-CH2-O-CH2CH2CH2-CH(CH3)-NH-C(O)- | 4-OCH3-C6H4- | 398.46 | 399 |
| 277 | | (CH3)3C-O-C(O)-N(CH3)-CH2CH2-CH(CH3)-NH-C(O)- | 4-OCH3-C6H4- | 469.54 | 470 |
| 278 | | H3C-NH-CH2CH2-CH(CH3)-NH-C(O)- | 4-OCH3-C6H4- | 369.42 | 370 |

TABLE 5-continued

| Example No. | Absolute configuration | R | Ar | Molecular weight | MS: m/z (M + H)+ |
|---|---|---|---|---|---|
| 279 | | CH₃C(O)N(CH₃)CH₂CH₂CH(CH₃)NHC(O)- | 4-OCH₃-C₆H₄- | 411.46 | 412 |
| 280 | | morpholine-C(O)CH₂CH₂CH(CH₃)NHC(O)- | 3-pyridyl-CH₂- | 429.50 | 430 |
| 281 | | CH₃CH₂OCH₂CH₂CH(CH₃)NHC(O)- | 2-thienyl- | 360.43 | 361 |
| 282 | | (CH₃)₃COC(O)N(CH₃)CH₂CH₂CH₂CH(CH₃)NHC(O)- | 4-OCH₃-C₆H₄- | 483.56 | 484 |
| 283 | | CH₃C(O)N(CH₃)CH₂CH₂CH₂CH(CH₃)NHC(O)- | 4-OCH₃-C₆H₄- | 425.48 | 426 |
| 284 | | CH₃CH₂CH₂CH(CH₃)NHC(O)- | 2-thienyl- | 330.41 | 331 |
| 285 | | CH₃CH₂CH₂CH(CH₃)NHC(O)- | 4-OCH₃-C₆H₄- | 354.41 | 355 |

TABLE 5-continued

| Example No. | Absolute configuration | R | Ar | Molecular weight | MS: m/z (M + H)+ |
|---|---|---|---|---|---|
| 286 | | 1-methylbutyl-NHC(O)- | 4-(2-methoxyethoxy)phenyl | 398.46 | 399 |
| 287 | | 5-(morpholin-4-yl)-5-oxo-pentan-2-yl-NHC(O)- | thiophen-2-yl | 443.52 | 444 |
| 288 | (S)- | 5-methoxy-5-methylhexan-2-yl-NHC(O)- | thiophen-2-yl | 402.51 | 403 |
| 289 | (S)- | (E)-6-methoxyhex-3-en-2-yl-NHC(O)- | 4-methoxyphenyl | 396.44 | 397 |
| 290 | (S)- | (E)-6-methoxyhex-3-en-2-yl-NHC(O)- | thiophen-2-yl | 372.44 | 373 |
| 291 | | 5-methoxy-5-methylhexan-2-yl-NHC(O)- | phenyl | 382.46 | 383 |
| 292 | | 5-methoxy-5-methylhexan-2-yl-NHC(O)- | benzo[1,3]dioxol-5-yl | 426.47 | 427 |

TABLE 5-continued

| Example No. | Absolute configuration | R | Ar | Molecular weight | MS: m/z (M + H)+ |
|---|---|---|---|---|---|
| 293 | (S)- | 1-(3-methoxyphenyl)ethyl-NHC(O)- | 4-(4-piperidin-1-yl-piperidine-1-carbonyloxy)phenyl | 598.70 | 599 |
| 294 | | 1-(3,4-dimethoxy-5-methoxyphenyl)ethyl-NHC(O)- (3,4,5-trimethoxyphenyl) | thiophen-2-yl | 454.50 | 455 |
| 295 | | 1-(benzo[1,3]dioxol-5-yl)ethyl-NHC(O)- | thiophen-2-yl | 408.43 | 409 |
| 296 | | 1-(3,4,5-trimethoxyphenyl)ethyl-NHC(O)- | 4-methoxyphenyl | 478.50 | 479 |
| 297 | | 1-(benzo[1,3]dioxol-5-yl)ethyl-NHC(O)- | 4-methoxyphenyl | 432.43 | 433 |
| 298 | | CH3C(O)OC(CH3)2C(O)N(CH3)CH2CH2CH(CH3)NHC(O)- | 4-methoxyphenyl | 497.55 | 498 |

TABLE 5-continued

| Example No. | Absolute configuration | R | Ar | Molecular weight | MS: m/z (M + H)+ |
|---|---|---|---|---|---|
| 299 | | | thiophen-2-yl | 473.55 | 474 |
| 301 | | | benzo[1,3]dioxol-5-yl | 446.42 | 447 |
| 303 | (S)- | | 3-chlorophenyl | 422.87 | 423 |
| 304 | | | 3-chlorophenyl | 436.85 | 437 |
| 305 | | | 3-chlorophenyl | 482.92 | 483 |
| 306 | | | 3-(pyridin-3-ylmethoxy)phenyl | 509.52 | 510 |
| 307 | | | 3-(pyridin-3-ylmethoxy)phenyl | 555.58 | 556 |

TABLE 5-continued
Structural formula
| Example No. | Absolute configuration | R | Ar | Molecular weight | Physicochemical data MS: m/z (M + H)+ |
|---|---|---|---|---|---|
| 308 | (S)- | 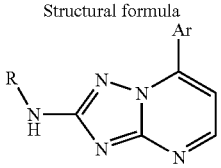 | 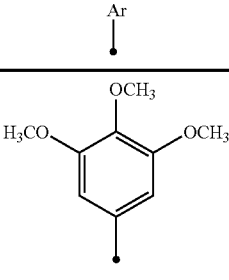 | 478.50 | 479 |
| 309 | | 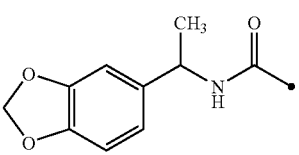 | 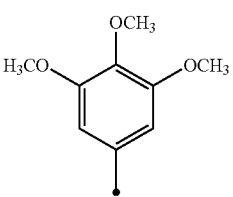 | 492.48 | 493 |
| 310 | | 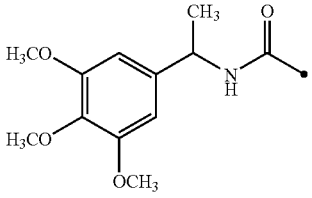 | 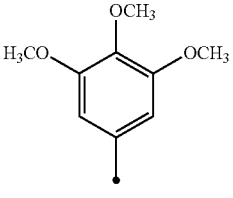 | 538.55 | 539 |
| 311 | | 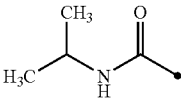 | 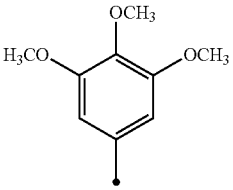 | 386.41 | 387 |
| 312 | | 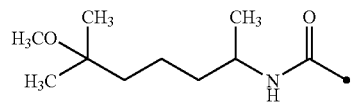 | 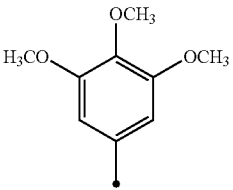 | 472.55 | 473 |
| 314 | | 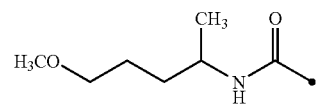 | 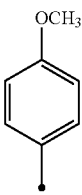 | 384.43 | 385 |
| 315 | | 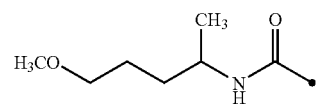 | 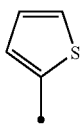 | 360.43 | 361 |

TABLE 5-continued

Structural formula

| Example No. | Absolute configuration | R | Ar | Molecular weight | Physicochemical data MS: m/z (M + H)⁺ |
|---|---|---|---|---|---|
| 316 | (S)- | 1-phenylethyl-NHC(O)- | pyridine N-oxide (3-yl) | 375.38 | 376 |
| 318 | | 5-hydroxy-5-methylhexan-2-yl-NHC(O)- | thiophen-2-yl | 374.47 | 375 |
| 320 | (R)- | 5-methoxy-5-methylhexan-2-yl-NHC(O)- | 4-methoxyphenyl | 412.50 | 413 |
| 321 | | 5-methoxy-5-methylhexan-2-yl-NHC(O)- | 4-(tetrahydropyran-4-ylmethoxy)phenyl | 496.61 | 497 |
| 322 | (S)- | 1-(3-methoxyphenyl)ethyl-NHC(O)- | 4-(tetrahydropyran-4-ylmethoxy)phenyl | 502.58 | 503 |
| 323 | | 1,3-dioxolan-2-yl derivative | 4-methoxyphenyl | 426.48 | 427 |
| 324 | | 5-methoxy-5-methylhexan-2-yl-NHC(O)- | 4-hydroxyphenyl | 398.47 | 399 |

TABLE 5-continued

| Example No. | Absolute configuration | R | Ar | Molecular weight | MS: m/z (M + H)+ |
|---|---|---|---|---|---|
| 325 | | tetrahydropyran-4-ylmethyl-O-CH(CH3)-CH2-NHC(O)- | 4-OCH3-C6H4- | 440.51 | 441 |
| 326 | | CH3C(O)-CH2-CH2-CH(CH3)-NHC(O)- | 4-OCH3-C6H4- | 382.43 | 383 |
| 328 | | H3C-CH2-O-CH2-CH2-CH(CH3)-NHC(O)- | 4-(tetrahydropyran-4-ylmethoxy)-C6H4- | 468.56 | 469 |
| 329 | | H3C-CH2-O-CH2-CH2-CH(CH3)-NHC(O)- | 4-OH-C6H4- | 370.41 | 371 |
| 330 | | (CH3)2C(OH)-CH2-CH2-CH(CH3)-NHC(O)- | benzo[1,3]dioxol-5-yl | 412.45 | 413 |
| 331 | | tetrahydropyran-4-ylmethyl-O-CH(CH3)-CH2-NHC(O)- | thiophen-2-yl | 416.51 | 417 |
| 332 | | H3CO-CH2-CH2-CH(CH3)-NHC(O)- | thiophen-2-yl | 346.41 | 347 |

TABLE 5-continued

Structural formula

[Core structure: Ar-substituted [1,2,4]triazolo[1,5-a]pyrimidine with R-NH- at 2-position]

| Example No. | Absolute configuration | R | Ar | Molecular weight | MS: m/z (M + H)⁺ |
|---|---|---|---|---|---|
| 333 | | H₃CO-CH₂CH₂-CH(CH₃)-NH-C(O)-CH₂-* | 4-OCH₃-phenyl | 370.41 | 371 |
| 334 | | (tetrahydropyran-4-yl)-CH₂CH₂-CH(CH₃)-NH-C(O)-CH₂-* | 1,3-benzodioxol-5-yl | 424.51 | 425 |
| 335 | | (tetrahydropyran-4-yl)-CH₂-O-CH₂-CH(CH₃)-NH-C(O)-CH₂-* | 1,3-benzodioxol-5-yl | 454.49 | 455 |
| 336 | | H₃CO-CH₂CH₂-CH(CH₃)-NH-C(O)-CH₂-* | 1,3-benzodioxol-5-yl | 384.40 | 385 |

TEST EXAMPLE 1

Effect on Expression of MHC Class I from T1 Cells (Human Lymphoma Cell Line 174×CEM.)

Using a 96-well flat bottom microplate, T1 cells ($5.7 \times 10^3$ cells/200 μl/well) were cultured in an RPMI 1640 medium (Iwaki Glass) containing 10% fetal bovine serum (hereinafter abbreviated as FBS; Iruvine Scientific) in an incubator containing 5% carbon dioxide at 37° C. for 3 days, in the presence of a test compound having each concentration obtained by dilution at a common ratio route of 10 from 400 μM. After completion of the culture, the cells were stained with fluoroisothiocyanate-labeled mouse anti-human MHC class I monoclonal antibody (an antibody produced from the cell line W6/32 (ATCC No. CRL 1991)). The mean fluorescence intensity of the stained cells (hereinafter referred to as MFI) was measured using flow cytometry FACScan (BD). The obtained value was defined as an expression level of MHC class I molecules. A test compound concentration necessary for suppressing 20% of the expression level of MHC class I molecules ($EC_{20}$ value) was calculated using the following formula (1). The results are shown in Tables 6 and 7.

$$MHC \text{ class I expression-inhibiting rate } (\%) = \left(1 - \frac{E \exp}{C \exp}\right) \times 100 \quad \text{Formula (1)}$$

Eexp: MFI of cultured cells containing test compound after being stained with antibody Cexp: MFI of cultured cells containing no test compounds after being stained with antibody

TABLE 6

| Example No. | $EC_{20}$, μM |
|---|---|
| 001 | 1.1 |
| 007 | 0.18 |

TABLE 6-continued

| Example No. | EC$_{20}$, μM |
|---|---|
| 013 | 0.48 |
| 014 | 0.57 |
| 015 | 0.045 |
| 016 | 0.73 |
| 017 | 0.22 |
| 018 | 0.052 |
| 019 | 1.1 |
| 023 | 0.43 |
| 024 | 0.24 |
| 025 | 0.5 |
| 026 | 0.9 |
| 027 | 0.067 |
| 028 | 0.152 |
| 029 | 0.234 |
| 030 | 0.4 |
| 031 | 0.4 |
| 032 | 0.25 |
| 035 | 0.38 |
| 037 | 0.2 |
| 039 | 0.3 |
| 044 | 0.48 |
| 045 | 0.03 |
| 046 | 0.34 |
| 049 | 0.23 |
| 050 | 0.33 |
| 053 | 0.37 |
| 054 | 0.63 |
| 055 | 0.69 |
| 056 | 0.55 |
| 059 | 0.23 |
| 064 | 0.67 |
| 065 | 0.35 |
| 066 | 0.72 |
| 067 | 0.3 |
| 068 | 0.14 |
| 069 | 0.41 |
| 070 | 0.48 |
| 071 | 0.53 |
| 074 | 0.55 |
| 077 | 0.54 |
| 078 | 0.67 |
| 079 | 0.97 |
| 080 | 0.71 |
| 083 | 0.87 |
| 084 | 0.42 |
| 085 | 0.4 |
| 086 | 0.34 |
| 087 | 0.78 |
| 088 | 0.15 |
| 089 | 0.21 |
| 090 | 0.4 |
| 091 | 0.21 |
| 092 | 0.2 |
| 093 | 0.7 |
| 094 | 0.2 |
| 095 | 0.63 |
| 096 | 0.55 |
| 097 | 0.47 |
| 098 | 0.14 |
| 099 | 0.44 |
| 100 | 0.32 |
| 101 | 0.21 |
| 102 | 0.19 |
| 103 | 0.62 |
| 104 | 0.43 |
| 106 | 0.51 |
| 108 | 0.13 |
| 109 | 0.11 |
| 110 | 0.79 |
| 112 | 0.85 |
| 115 | 0.6 |
| 116 | 0.57 |
| 117 | 0.19 |
| 118 | 0.61 |
| 119 | 0.21 |
| 120 | 0.25 |

TABLE 6-continued

| Example No. | EC$_{20}$, μM |
|---|---|
| 121 | 0.17 |
| 122 | 0.34 |
| 123 | 0.48 |
| 124 | 0.21 |
| 125 | 0.82 |
| 126 | 0.32 |
| 127 | 0.08 |
| 128 | 0.54 |
| 129 | 0.18 |
| 130 | 0.13 |
| 131 | 0.16 |
| 132 | 0.039 |
| 133 | 0.19 |
| 134 | 0.05 |
| 135 | 0.81 |
| 138 | 0.15 |
| 139 | 0.13 |
| 142 | 0.06 |
| 143 | 0.74 |
| 144 | 0.46 |
| 148 | 0.26 |
| 149 | 0.63 |
| 150 | 0.71 |
| 151 | 0.22 |
| 152 | 0.78 |
| 154 | 0.07 |
| 155 | 0.94 |
| 156 | 0.05 |
| 158 | 0.39 |
| 160 | 0.014 |
| 165 | 0.3 |
| 167 | 0.2 |
| 168 | 0.67 |
| 169 | 0.66 |
| 170 | 0.25 |
| 171 | 0.29 |
| 172 | 0.24 |
| 174 | 0.33 |
| 175 | 0.3 |
| 176 | 0.2 |
| 180 | 0.35 |
| 181 | 0.43 |
| 182 | 0.28 |
| 183 | 0.22 |
| 184 | 0.21 |
| 185 | 0.35 |
| 186 | 0.44 |
| 187 | 0.16 |
| 188 | 0.08 |
| 189 | 0.59 |
| 192 | 0.9 |

TABLE 7

| Example No. | EC$_{20}$, μM |
|---|---|
| 193 | 0.31 |
| 194 | 0.42 |
| 195 | 0.06 |
| 196 | 0.17 |
| 197 | 0.21 |
| 199 | 0.28 |
| 200 | 0.07 |
| 201 | 0.16 |
| 202 | 0.06 |
| 203 | 0.19 |
| 204 | 0.07 |
| 205 | 0.19 |
| 206 | 0.22 |
| 207 | 0.06 |
| 208 | 0.18 |
| 209 | 0.04 |

TABLE 7-continued

| Example No. | EC$_{20}$, μM |
|---|---|
| 210 | 0.13 |
| 211 | 0.06 |
| 212 | 0.18 |
| 213 | 0.15 |
| 214 | 0.42 |
| 215 | 0.15 |
| 216 | 0.16 |
| 217 | 0.32 |
| 218 | 0.18 |
| 219 | 0.05 |
| 220 | 0.72 |
| 221 | 0.12 |
| 222 | 0.1 |
| 223 | 0.014 |
| 224 | 0.09 |
| 225 | 0.05 |
| 226 | 0.05 |
| 227 | 0.07 |
| 229 | 0.69 |
| 230 | 0.22 |
| 231 | 0.05 |
| 232 | 0.04 |
| 233 | 0.04 |
| 234 | 0.22 |
| 235 | 0.59 |
| 236 | 0.08 |
| 237 | 0.25 |
| 238 | 0.015 |
| 239 | 0.11 |
| 244 | 0.019 |
| 245 | 0.18 |
| 246 | 0.05 |
| 247 | 0.037 |
| 248 | 0.014 |
| 249 | 0.07 |
| 251 | 0.06 |
| 252 | 0.05 |
| 253 | 0.27 |
| 254 | 0.23 |
| 255 | 0.0056 |
| 256 | 0.55 |
| 257 | 0.03 |
| 258 | 0.0087 |
| 259 | 0.06 |
| 260 | 0.06 |
| 261 | 0.08 |
| 262 | 0.03 |
| 263 | 0.0079 |
| 264 | 0.07 |
| 265 | 0.11 |
| 266 | 0.2 |
| 267 | 0.55 |
| 269 | 0.015 |
| 272 | 0.069 |
| 273 | 0.6 |
| 274 | 0.11 |
| 275 | 0.54 |
| 276 | 0.12 |
| 277 | 0.18 |
| 280 | 0.2 |
| 281 | 0.12 |
| 282 | 0.058 |
| 283 | 0.2 |
| 284 | 0.19 |
| 285 | 0.32 |
| 286 | 0.16 |
| 287 | 0.77 |
| 288 | 0.02 |
| 289 | 0.11 |
| 290 | 0.34 |
| 291 | 0.23 |
| 292 | 0.1 |
| 293 | 0.09 |
| 294 | 0.07 |
| 295 | 0.79 |
| 296 | 0.07 |
| 297 | 0.11 |
| 298 | 0.08 |
| 299 | 0.43 |
| 300 | 0.019 |
| 301 | 0.64 |
| 302 | 0.18 |
| 303 | 0.68 |
| 305 | 0.52 |
| 306 | 0.23 |
| 307 | 0.14 |
| 308 | 0.76 |
| 313 | 0.29 |
| 314 | 0.08 |
| 315 | 0.27 |
| 317 | 0.06 |
| 318 | 0.04 |
| 319 | 0.02 |
| 320 | 0.23 |
| 321 | 0.03 |
| 322 | 0.02 |
| 323 | 0.03 |
| 324 | 0.18 |
| 325 | 0.07 |
| 326 | 0.21 |
| 327 | 0.15 |
| 328 | 0.07 |
| 329 | 0.06 |
| 330 | 0.21 |
| 331 | 0.15 |
| 332 | 0.76 |
| 333 | 0.41 |
| 334 | 0.06 |
| 335 | 0.26 |

These results show that the compound of the present invention inhibits the expression of MHC class I from T1 cells.

TEST EXAMPLE 2

Effect on Expression of MHC Class I Molecules from Human Peripheral Blood-Derived Dendritic Cells Monocytes were isolated from human peripheral blood by the specific gravity centrifugation method. Thereafter, using mouse anti-human CD14 antibody-binding microbeads and a magnetic cell separation system (Miltenyi Biotec), CD14 positive cells were separated from the peripheral blood monocytes. The separated CD14 positive cells were suspended in an RPMI 1640 medium containing 10% FBS, and the suspension was then inoculated in a 6-well plate, resulting in a concentration of $1.0 \times 10^6$ cells/well. It was cultured at 37° C. for 20 minutes in an incubator containing 5% carbon dioxide. After completion of the culture, non-adhesive cells, which did not have adhesiveness and were suspending in the solution, were eliminated. Thereafter, RPMI 1640 containing a 500 U/ml human recombinant granulocyte colony-stimulating factor (hereinafter referred to as GM-CSF; Anapure Bioscientific), 50 ng/ml human recombinant interleukin 4 (hereinafter referred to as IL-4; Pepro Tech), and 10% FBS, was added to the remaining suspension at a concentration of 2 ml/well. The obtained mixture was then cultured at 37° C. in an incubator containing 5% carbon dioxide. When adhesive CD14 positive cells are cultured in the presence of GM-CSF and IL-4, the CD14 positive cells were differentiated into non-adhesive immature dendritic cells. After the cells had been cultured for 7 days, non-adhesive cells were recovered to obtain immature dendritic cells. Using a 6-well plate, the immature dendritic cells ($2.5 \times 10^5$ cells/well) were cultured in RPMI 1640 containing a 100 U/ml human recombinant tumor necrosis factor-α (hereinafter referred to as TNF-a; Pepro Tech), a test compound, and 10% FBS, at 37° C. for 3 days in an incubator containing 5% carbon dioxide. The dendritic cells became mature as a result of the presence of TNF-α, but in the present test, a test compound was allowed to simultaneously act on the cells. The mature dendritic cells were then stained with fluoroisothiocyanate-labeled mouse anti-human MHC class I monoclonal antibody (an antibody generated from the cell line W6/32 (ATCC No. CRL 1991)). The rate of the number of cells wherein MHC class I molecules were highly expressed to the total number of cells was measured by flow cytometry. The reduction rate of the number of cells wherein MHC class I molecules were highly expressed was calculated using the following formula (2), and the concentrations of test compounds necessary for reduction of 50% ($EC_{50}$ values) were obtained. The results are shown in Table 8.

Reduction rate of the number of cells wherein MHC class I molecules are highly expressed (%) = $\left(1 - \dfrac{E \exp}{C \exp}\right) \times 100$   Formula (2)

Eexp: (The number of cells, wherein MHC class I molecules are highly expressed, in cultured cells containing test compound)/(the total number of cells)

Cexp: (The number of cells, wherein MHC class I molecules are highly expressed, in cultured cells containing no test compounds)/(the total number of cells)

TABLE 8

| Example No. of test compound | $EC_{50}$ (μM) |
|---|---|
| 001 | 0.46 |
| 007 | 0.66 |
| 015 | 0.13 |
| 018 | 0.29 |
| 024 | 0.16 |
| 027 | 0.22 |
| 029 | 0.48 |
| 030 | 0.48 |
| 037 | 0.20 |
| 039 | 0.54 |
| 045 | 0.12 |
| 049 | 0.21 |
| 059 | 0.53 |
| 067 | 2.22 |
| 069 | 2.85 |
| 071 | 0.67 |
| 101 | 0.22 |

The results show that the compound of the present invention inhibits expression of MHC class I molecules from human peripheral blood-derived dendritic cells.

TEST EXAMPLE 3

Effect on the Ability of Human Dendritic Cells to Induce the Growth of Allogenic T Cells Immature dendritic cells were cultured with a test compound and TNF-α for 3 days by the same method as that described in Test Example 2. The obtained dendritic cells ($2.5 \times 10^3$ cells/50 μl/well) were cultured together with human allogenic T cells ($2.0 \times 10^5$ cells/150 μl/well) in a 96-well flat bottom plate at 37° C. for 5 days in an incubator containing 5% carbon dioxide. Thereafter, [$^3$H]-thymidine (Amersham Pharmacia Biotech) was added thereto at an amount of 1 μCi/10 μl/well, 16 hours before completion of the culture. After completion of the culture, cells were captured on a glass filter using a cell harvester (Skatron Instrument) and then dried. Thereafter, Scintillator ACS-II (Amersham Pharmacia Biotech) was added thereto, and the radioactivity of [$^3$H]-thymidine incorporated into the cells were then measured using a liquid scintillation counter. The inhibition rate of the DNA synthesis of lymphocytes was calculated using the following formula (3). Thereafter, the concentration of a test compound necessary for inhibition of 50% ($IC_{50}$ value) was obtained. The results are shown in Table 9.

Inhibition rate of DNA synthesis of lymphecytes (%) = $\left(1 - \dfrac{E \exp}{C \exp}\right) \times 100$   Formula (3)

Eexp: The amount of [$^3$H]-thymidine incorporated into cultured cells containing test compound Cexp: The amount of [$^3$H]-thymidine incorporated into cultured cells containing no test compounds

TABLE 9

| Example No. of test compound | $IC_{50}$ (μM) |
|---|---|
| 001 | 1.23 |
| 005 | 0.65 |
| 007 | 0.97 |
| 015 | 0.38 |
| 024 | 0.82 |
| 029 | 3.48 |
| 030 | 1.25 |
| 037 | 1.36 |
| 039 | 1.52 |
| 045 | 0.28 |
| 049 | 1.63 |
| 057 | 2.70 |
| 101 | 0.625 |
| 132 | 0.625 |
| 158 | 0.69 |
| 160 | 0.156 |

The results show that the compound of the present invention inhibits the ability of dendritic cells to induce the growth of lymphocytes.

TEST EXAMPLE 4

Effect on Mouse Plaque Forming Cells (PFCs)

Sheep erythrocytes (Nippon Seibutsu Zairyo Center, Co., Ltd.) were intraperitoneally administered to each of BALB/c mice (Charles River Japan, Inc.; female; 8-week-old) at an amount of $1.0 \times 10^8$ cells. Thereafter, a test compound was administered thereto twice a day for 4 days after the first administration (only once on the first day) (n=4). On the day subsequent to completion of the administration of the test compound, splenic cells were prepared from the mouse, and the number of PFCs to the sheep erythrocytes was counted by the method of Cunninham (Cunninham, A. J. et al., Immunology, vol. 14, p. 599 (1968)). The number of PFCs per number of splenic cells of $1.0 \times 10^6$ was obtained. The reduction rate of the number of PFC in the mouse to which the test compound had been administered, to the number of PFCs in a control mouse to which the test compound had not been administered but only a solvent had been administered, was calculated using the following formula (4). The results are shown in Table 10.

Reduction rate of the number of PFCs (%) =     Formula (4)

$$\left(1 - \frac{E \exp}{C \exp}\right) \times 100$$

Eexp: The number of PFCs per 1×10⁶ splenic cells of mouse to which test compound was administered Cexp: The number of PFCs per 1×10⁶ splenic cells of mouse to which solvent was administered

TABLE 10

| Example No. of test compound | Administration route | Dose (mg/kg/single administration) | Reduction rate (%) |
|---|---|---|---|
| 029 | Oral | 50 | 49.3 |
| 037 | Intraperitoneal | 25 | 31.2 |
| Control | Intraperitoneal | 0 | 0.0 |

The number of PFCs was reduced by administration of the test compound. The number of PFC indicates the number of splenic cells that produce antibodies reacting with sheep erythrocytes. Thus, it was revealed that the compound of the present invention inhibits generation of antibodies.

TEST EXAMPLE 5

Effect on Mouse Delayed-Type Hypersensitivity Reaction (DTH Reaction)

1.0×10⁵ sheep erythrocytes (Nippon Seibutsu Zairyo Center, Co., Ltd.) were administered to each of BALB/c mice (Charles River Japan, Inc.; female; 8-week-old) by intravenous injection for sensitization. From the day of administration of the sheep erythrocytes, a test compound was administered to the mouse. As a control, a 0.5% carboxymethyl cellulose (CMC)-Na solution and a normal saline solution used as solvents were administered to the same type of mouse via oral administration or intraperitoneal administration. Five days after the antigen sensitization, 1.0×10⁸ sheep erythrocytes were subcutaneously injected into the sole of the mouse. 24 hours later, the thickness of the sole was measured. The value obtained by subtracting the mean value of the thicknesses of the soles of mice, to which a normal saline solution had been administered instead of the sheep erythrocytes, from the above measurement value, was defined as swelling of the sole generated as a result of the DTH reaction. The inhibition rate of the swelling of the sole caused by the DTH reaction was calculated using the following formula (5). The amount of the test compound necessary for inhibition of 50% (ED$_{50}$ value) was obtained as the activity of the test compound to inhibit the DTH reaction. The results are shown in the following table. It is to be noted that cyclosporin A was used as a positive control.

Inhibition rate of DTH reaction     Formula (5)

(inhibition rate of swelling of sole) (%) =

$$\left(1 - \frac{E \exp}{C \exp}\right) \times 100$$

Eexp: Swelling of sole of mouse to which test compound was administered

Cexp: Swelling of sole of mouse to which solvent was administered

TABLE 11

| Example No. of test compound | Administration route | Administration period (days) | Dose (mg/kg/single administration) | Inhibition rate (%) |
|---|---|---|---|---|
| 029 | Oral | 7 | 50 | 37.0 |
|  |  | 7 | 100 | 49.5 |
|  |  | 8 | 50 × 2* | 80.0 |
| 135 | Intraperitoneal | 7 | 100 | 40.2 |
| Cyclosporin A | Oral | 8 | 50 | 59.1 |

*Test compound administered at a dose of 50 mg/kg, twice a day

It was revealed that the compound of the present invention inhibits the DTH reaction and that it has the effect of suppressing the type IV allergic reaction.

TEST EXAMPLE 6

Effect on Graft Versus Host (GVH) Reaction

The effect of the compound on the GVH reaction was determined in accordance with the spleen weight measurement method of Simonsen et al. (Simonsen et al., Annals of the New York Academy of Sciences, p. 73 (1978)). Splenic cells were prepared from C57BL/6 mice (Charles River Japan, Inc.; female; 10-week-old), and the cells (5.0×10⁶ cells) were transferred into the abdominal cavity of each of BDF1 mice (Charles River Japan; 7-day-old). From the day of transferring of the above cells, the test compound having each diluted concentration or a 5% glucose solution used as a solvent was subcutaneously administered to the BDF1 mice twice a day for 7 consecutive days. Eight days after the transferring of the above cells, the spleen weight of each of the BDF1 mice was measured. The reduction rate of the spleen weight was calculated using the following formula (6). The amount of the test compound necessary for reduction of 50% (ED$_{50}$ value) was obtained. The results are shown in the following table.

Inhibition rate of GVH reaction     Formula (6)

(reduction weight of spleen weight) (%) =

$$\left(1 - \frac{E \exp}{C \exp}\right) \times 100$$

Eexp: Spleen weight of mouse to which test compound was administered

Cexp: Spleen weight of mouse to which solvent was administered

TABLE 12

| Example No. of test compound | Dose (mg/kg/single administration) | Inhibition rate (%) |
|---|---|---|
| 039 | 25 × 2 | 14.1 |
|  | 50 × 2 | 29.5 |

The compound of the present invention has the effect of suppressing the GVH reaction, thereby suppressing rejection and graft versus host reaction occurring after transplantation.

TEST EXAMPLE 7

Life-Lengthening Effect on Graft Versus Host Disease (GVHD)

The present test was carried out by modification of the method of Jonathan et al. (Jonathan et al., Blood, p. 93 (1999)). First, 6.0 Gy X-ray was applied to (C57BL/6XB6. C—H2$^{bm1}$) F1 mice (produced by mating 6XB6.C—H2$^{bm1}$ mice (Jackson Laboratory) with C57BL/6 mice (Charles River Japan); female; 8 to 12-week-old). Thereafter, CD8 positive T cells (1.25×10$^6$ cells) prepared from the splenic cells of C57BL/6 mice (Charles River Japan; female; 8-week-old) were intravenously injected into the above (C57BL/6XB6. C—H2$^{bm1}$) F1 mice. From the day before the injection, the test compound having each diluted concentration or 0.5% carboxymethyl cellulose used as a solvent was orally administered to the mice once a day for 7 to 30 consecutive days. The day on which the transplantation was conducted was defined as day 0. Based on the median of the survival days of each group, the prolongation rate of such survival dates was calculated using the following formula (7). Thus, the effect of the test compound on GVHD was analyzed.

$$\text{Prolongation rate of survival days in mice suffering from } GVHD\ (\%) = \left(1 - \frac{E\ \exp}{C\ \exp}\right) \times 100 \qquad \text{Formula (7)}$$

Eexp: Median of survival days of test compound administration group

Cexp: Median of survival days of solvent administration group

The results are shown in Table 13. It was suggested hat the compound of the present invention has the effect of lengthening the survival days in mice suffering from GVHD and of suppressing rejection and graft versus host reaction occurring after transplantation.

TABLE 13

| Example No. of test compound | Dose (mg/kg/single administration) | Lengthening rate of survival days (%) |
|---|---|---|
| 029 | 25 | 75 |
|  | 100 | 200 |
| 132 | 100 | 200 |
| 219 | 25 | 200 |
| 274 | 100 | 55 |
| 300 | 10 | 100 |
| 317 | 30 | 24 |
| 319 | 10 | 200 |
|  | 50 | 200 |

TEST EXAMPLE 8

Effect on Autoimmune Disease Model SCG/kj Mice

Autoimmune disease model SCG/kj mice (Kaneshiro et al., Proceedings of National Academy of Sciences, Vol. 90, p. 3413 (1993)) were used to study the effect of the test compound on autoimmune disease. A test compound or solvent was orally administered to SCG/kj mice (bred by Nippon Kayaku Co., Ltd.; female; 8 to 10-week-old) at a dose of 100 mg/kg, once a day, for 59 consecutive days. Thereafter, the survival rate of the mice that survived for 60 days after the administration was obtained.

The survival rate after 60 days was found to be 80.0% in the test compound administration group, whereas it was found to be 42.1% in the solvent administration group. Since the compound of the present invention exhibited a clear life-lengthening effect on the SCG/kj mice (p <0.05; a significant difference found by a logrank test), it can be said that the present compound has the effect of suppressing the development of autoimmune disease.

TEST EXAMPLE 9

Inhibitory Action on Blastogenesis of Mouse Splenic Cells

The spleen was excised from each of BALB/c mice (Charles River Japan; female; 10-week-old), and it was allowed to pass through a mesh to obtain a single cell suspension. This single cell suspension was prepared to be 1.0×10$^6$ cells/ml. Thereafter, 200 µl of the suspension was fractionated into each well of a 96-well plate. Thereafter, as blastogenic stimulation, 5 µg/ml concanavalin A (Pharmacia) or 25 µg/ml *Escherichia coli*-derived lipopolysaccharide (DIFCO) was added to the well, and then, a solution containing a test compound with each different concentration was further added thereto at an amount of 20 µl/well. The obtained mixture was cultured at 37° C. for 72 hours in an incubator containing 5% carbon dioxide. Thereafter, a 1 µCi/10 µl/well [$^3$H]-thymidine solution was added thereto 64 hours after initiation of the culture. After completion of the culture (72 hours later), the cells were captured on a filter using a cell harvester, and they were then dried. Thereafter, scintillator was added thereto, and the radioactivity of [$^3$H]-thymidine incorporated into the cells was then measured using a liquid scintillation counter. The inhibition rate of the DNA synthesis was calculated using the aforementioned formula (3). Thereafter, the concentration of a test compound necessary for inhibition of 50% (IC$_{50}$ value) was obtained. The results are shown in Table 14.

TABLE 14

| Example No. of test compound | Lymphocyte blastogenesis IC$_{50}$ (µM) | |
|---|---|---|
| | ConA stimulation | LPS stimulation |
| 029 | 0.71 | 0.30 |
| 045 | 0.41 | 0.09 |
| 101 | 0.58 | 0.18 |
| 132 | 0.08 | 0.06 |
| 160 | 0.07 | 0.04 |
| 183 | 0.55 | 0.14 |
| 184 | 0.63 | 0.29 |
| Cyclosporin A (control) | 0.03 | 0.12 |

It was found that the compound of the present invention inhibits the blastogenesis of lymphocytes by mitogen stimulation and has action to directly suppress the growth of lymphocytes.

TEST EXAMPLE 10

Action on Expression of Antigen-Presenting Molecules and Costimulatory Molecules of Human Peripheral Blood-Derived Dendritic Cells The dendritic cells obtained by the same method as in Test Example 2 were suspended in RPMI 1640 comprising 10% FCS containing 500 U/ml GM-CSF, 50 ng/ml IL-4, and 100 U/ml human recombinant tumor necrosis factor ($2.5 \times 10^6$ cells/ml). Thereafter, the suspension was inoculated into a 6-well plate at an amount of 2.0 ml/well, and the test compound was then added thereto. The mixture was cultured at 37° C. for 3 days in an incubator containing 5% carbon dioxide. Thereafter, the suspended cells were recovered. The cells were then stained with fluoroisothiocyanate-labeled mouse monoclonal antibodies reacting with MHC class I (Bechman Coulter), CD1a (Immunotech), CD40 (Pharmingen), CD80 (Pharmingen), and CD83 (Immunotech). Thereafter, mean fluorescence intensity and the ratio of positive cells were measured by flow cytometry. The expression level was calculated by the formula "the mean fluorescence intensity x the ratio of positive cells," and the inhibition rate of the surface antigen expression level of dendritic cells was then obtained by the following formula (8). The results are shown in Table 15.

$$\text{Inhibition rate of surface antigen expression of dendritic cells (\%)} = \left(1 - \frac{E \exp}{C \exp}\right) \times 100 \quad \text{Formula (8)}$$

Eexp: Expression level of surface antigens of dendritic cells cultured in the presence of test compound
Cexp: Expression level of surface antigens of dendritic cells cultured in the absence of test compound

TABLE 15

| Example No. of test compound | Antigen presenting molecule and costimulatory molecule | Expression inhibition rate by test compound (%) | | |
|---|---|---|---|---|
| | | Analyte 1 | Analyte 2 | Analyte 3 |
| 029 | CD1a | 55.6 | n.t. | n.t. |
| | CD40 | 10.8 | −5.4 | 12.9 |
| | CD80 | 83.8 | 12.1 | 26.8 |
| | CD83 | 62.6 | 88.6 | 42.7 |
| | MHC class I | 72.3 | 63.9 | 72.6 |
| | MHC class II | 65.6 | 93.3 | 50.2 | n.t.: not tested

Specimens 1, 2, and 3 indicate dendritic cells separated from the peripheral bloods of different healthy subjects. The results show that the compound of the present invention suppresses not only the expression of CD1a and MHC class I molecules that are antigen-presenting molecules, but also the expression of CD40, CD80, and CD83 that are costimulatory molecules, and that it has action to induce immune tolerance.

In addition, CD83 is a marker molecule for the differentiation and maturation of dendritic cells. From the result that the expression of such CD83 was inhibited, it is considered that the compound of the present invention also suppresses the differentiation and maturation of dendritic cells.

TEXT EXAMPLE 11

Cytotoxic Effect on T1 Cells (Human Lymphoma Cell Line 174xCEM.)

Using a 96-well flat bottom microplate, T1 cells ($5.7 \times 10^3$ cells/200 μl/well) were cultured in an RPMI 1640 medium containing 10% FBS in an incubator containing 5% carbon dioxide at 37° C. for 3 days, in the presence of a test compound having each concentration obtained by dilution with a common ratio route of 10 from 400 μM. After completion of the culture, the cells that had been damaged by cytotoxicity were stained with propodium iodide. Using flow cytometry FACScan (BD), $IC_{50}$ was obtained from the ratio of the number of stained cells to the total cell number. The obtained value was defined as cytotoxic activity. The results are shown in Table 16.

TABLE 16

| Example No. of test compound | $IC_{50}$ (μM) |
|---|---|
| 010 | 0.2 |
| 101 | 1.2 |
| 137 | 0.9 |
| 223 | 1.2 |
| 238 | 0.7 |
| 244 | 0.5 |

Thus, it was revealed that the compound of the present invention exhibits cytotoxic action on T1 cells and has anticancer activity.

INDUSTRIAL APPLICABILITY

Taking into consideration the aforementioned physicochemical properties and biological properties, the [1,2,4]triazolo[1,5-a]pyrimidin-2-ylurea derivative represented by the formula (1) of the present invention or a pharmaceutically acceptable salt thereof is considered to be a novel compound. This compound exhibits antigen presentation inhibiting-activity and lymphocytic function-suppressing activity, and is useful as a therapeutic or preventive agent for autoimmune disease, graft rejection reaction, graft versus host reaction, allergic disease, or inflammatory disease. In addition, this compound also suppresses the expression of costimulatory molecules associated with antigen presentation, and is also useful as a pharmaceutical for immune tolerance induction. Moreover, it is also useful as a pharmaceutical for treatment of malignant tumors. The [1,2,4]triazolo[1,5-a]pyrimidin-2-ylurea derivative represented by the formula (1) of the present invention or a pharmaceutically acceptable salt thereof exhibited excellent activity in in vitro and in vivo immunosuppressive activity tests, and it is useful as a preventive and/or therapeutic agent for rejection and/or graft versus host reaction in organ and/or bone marrow transplantation, autoimmune disease, allergic disease, and/or inflammatory disease, as an anticancer drug, and as an immune tolerance inducer for transplanted organ and/or transplanted bone marrow.

The invention claimed is:

1. A compound of formula (1), or a pharmacologically acceptable salt thereof:

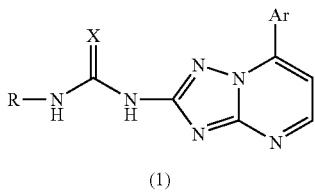

Formula 1

(1)

wherein Ar represents a phenyl group, which may have 1 to 4 identical or different substituents selected from the group consisting of a fluoro group, chloro group, hydroxyl group, methyl group, methoxy group, ethoxy group, isopropoxy group, isobutoxy group, benzyloxy group, methoxymethoxy group, 2-methoxyethoxy group, 2-methoxyethoxymethoxy group, 2-(2-methoxyethoxy)ethoxy group, 2-[2-(2-methoxyethoxy)ethoxy]ethoxy group, tetrahydrofuran-2-ylmethoxy group, tetrahydropyran-4-ylmethoxy group, 2-[1,3]dioxan-2-ylethoxy group, 2-dimethylaminoethoxy group, 3-dimethylaminopropoxy group, 2-diethylaminoethoxy group, 2-morpholin-4-yl-2-oxoethoxy group, 2-piperidin-1-ylethoxy group, 3-piperidin-1-ylpropoxy group, 2-morpholin-4-ylethoxy group, 3-morpholin-4-ylpropoxy group, pyridin-2-ylmethoxy group, pyridin-3-ylmethoxy group, pyridin-4-ylmethoxy group, amino group, dimethylamino group, diethylamino group, and methylenedioxy group; a 2,3-dihydrobenzofuran-5-yl group, or a thiophen-2-yl group; X represents O; and R represents a hydrogen atom or a group represented by any one of the following formulas (2) to (6):

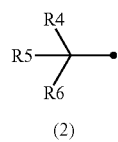

Formula 2

(2)

wherein R4 represents a hydrogen atom, a methyl group, an ethyl group, or an isopropyl group;
R5 represents a hydrogen atom or a methyl group; and
R6 represents a hydrogen atom, a methoxybutenyl group, or a (C1-C6) alkyl group, which may have 1 to 2 identical or different substituents selected from the group consisting of a cyclopentyl group, a cyclohexyl group, a morpholin-4-yl group, a hydroxyl group, a methoxy group, an ethoxy group, an n-propoxy group, an isopropoxy group, an isobutoxy group, a tert-butoxy group, an acetyl group, a propionyl group, a phenyl group, a halogenophenyl group, a pyridyl group, an imidazolyl group, a (C1-C6) alkyloxycarbonyl group, a phenylaminocarbonyl group, a tetrahydrofurfurylaminocarbonyl group, a morpholin-4-ylcarbonyl group, a 2-methyl[1,3]dioxolan-2-yl group, and a di(C1-C6)alkylamino group, which may be substituted with 1 to 2 identical or different substituents selected from a (C1-C6)alkyl group, a (C1-C6)acyl group, a (C1-C6)acyloxy(C1-C6)acyl group, and a (C1-C6)alkoxycarbonyl group,

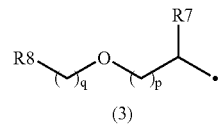

Formula 3

(3)

wherein R7 represents a hydrogen atom, a methyl group, or an ethyl group;
R8 represents a tetrahydrofuran-2-yl group or a tetrahydropyran-4-yl group; and
the sum of p and q is an integer of 4 or less,

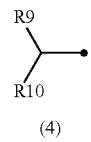

Formula 4

(4)

wherein R9 represents a hydrogen atom, a methyl group, or an ethyl group; and
R10 represents a phenyl group having 1 to 4 substituents selected from the group consisting of a hydroxy group, a (C1-C6)alkoxy group, a halogeno group, a (C1-C6) alkoxycarbonyl group, a nitro group, a methylenedioxy group, a benzyloxycarbonyloxy group, and a methanesulfonyloxy group; a naphthyl group, or a pyridyl group,

Formula 5

(5)

wherein Cy represents a phenyl group, a cyclopentyl group, a cyclohexyl group, an adamantyl group, a 1,2,3,4-tetrahydronaphthalen-1-yl group, or a piperadinyl group, which may be substituted with 1 to 4 identical or different groups selected from the group consisting of a hydroxyl group, a carboxyl group, a benzyl group, a (C1-C7)-acyl group, a (C1-C6)-alkoxycarbonyl group, an N—(C1-C6)-alkylcarbamoyl group, an N,N-di(C1-C6)alkylcarbamoyl group, and

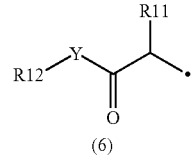

Formula 6

(6)

wherein Y represents a single bond;
R11 represents a hydrogen atom, a methyl group, an ethyl group, a n-propyl group, or an isopropyl group; and
R12 represents a hydroxyl group, a (C1-C6) alkoxyl group, an amino group, a (C1-C6) alkylamino group, which may be substituted with 1 to 2 identical or different substituents selected from the group consisting of a(C1-C6)alkoxyl group, a (C1-C6)alkoxycarbonyl group, a phenyl group, a pyridyl group, an amino group represented by the formula NR13R14 (wherein each of R13 and R14 independently represents a hydrogen atom or a (C1-C6)alkyl group), a piperidin-1-yl group, a morpholin-4-yl group, and a piperazinyl group which may be substituted with a (C1-C6) alkyl group, a di(C1-C6) alkylamino group, which may be substituted with 1 to 2 identical or different substituents selected from said substituent group [C], a cyclohexylmethylamino group, a phenylamino group, a tetrahydrofurfurylamino group, a piperidin-1-yl group, a morpholin-4-yl group, or a piperazinyl group which may be substituted with a (C1-C6) alkyl group.

2. The compound according to claim 1, or a pharmaceutically acceptable salt thereof,
wherein, in said general formula (1), Ar represents a 3-hydroxyphenyl group, a 3-methoxyphenyl group, a 4-hydroxyphenyl group, a 4-methoxyphenyl group, a 3,4-methylenedioxyphenyl group, a 3-(pyridin-3-ylmethoxy)phenyl group, a 4-(tetrahydropyran-4-ylmethoxy)phenyl group, or a thiophen-2-yl group; and R represents an isopropyl group, 2-methoxy-1-methylethyl group, 2-ethoxy-1-methylethyl group, 2-propoxy-1-methylethyl group, 3-methoxy-1-methylpropyl group, 3-ethoxy-1-methylpropyl group, 4-methoxy-1-methylbutyl group, 1-methyl-2-trifluoromethoxyethyl group, 1-methyl-2- (2,2,2-trifluoroethoxy)ethyl group, 1-methyl-3-trifluoromethoxypropyl group, 4-hydroxy-1,4-dimethylpentyl group, 5-hydroxy-1,5-dimethylhexyl group, 5-methoxy-1,5-dimethylhexyl group, 1-methyl-3-(tetrahydropyran-4-yl)propyl group, 1-methyl-2-(tetrahydropyran-4-yloxy)ethyl group, 1-methyl-2-(tetrahydropyran-4-ylmethoxy)ethyl group, 1-methyl-3(2-methyl[1,3]dioxolan-2-yl)propyl group, 1-methyl-4-oxopentyl group, 1-(3-hydroxyphenyl)ethyl group, 1-(3-methoxyphenyl)ethyl group, 1-(3,4-methylenedioxyphenyl)ethyl group, 1-(3,4,5-trimethoxyphenyl)ethyl group, or 1-(3-methanesulfonyloxyphenyl) ethyl group.

3. The compound according to claim 1, or a pharmaceutically acceptable salt thereof, wherein, R in said general formula (1) represents an isopropyl group, an (S)-2-methoxy-1-methylethyl group, an (S)-3-methoxy-1-methylpropyl group, an (S)-3-ethoxy-1-methylpropyl group, an (S)-4-methoxy-1-methylbutyl group, an (S)-4-hydroxy-1,4-dimethylpentyl group, an (S)-5-hydroxy-1,5-dimethylhexyl group, an (S)-1-(3-methoxyphenyl)ethyl group, an (S)-1-(3,4-methylenedioxyphenyl)ethyl group, or an (S)-1-(3,4,5-trimethoxyphenyl)ethyl group.

4. A medicine, which comprises, as an active ingredient, the compound according to claim 1, or a pharmaceutically acceptable salt thereof together with a pharmaceutically acceptable carrier.

5. A compound selected from the following:
1-isopropyl-3-(7-thiophen-2-yl[1,2,4]triazolo[1,5-a]pyrimidin-2-yl)urea;
(S)-1-(3-ethoxy-1-methylpropyl)-3-[7-(3,4-methylenedioxyphenyl)-[1,2,4]triazolo[1,5-a]pyrimidin-2-yl]urea;
(S)-1-(4-methoxy-1-methylbutyl)-3-[7-(4-methoxyphenyl)-[1,2,4]triazolo[1,5-a]pyrimidin-2-yl]urea;
(S)-1-(4-hydroxy-1,4-dimethylpentyl)-3-[7-(4-methoxyphenyl)-[1,2,4]triazolo[1,5-a]pyrimidin-2-yl]urea;
(S)-1-(5-hydroxy-1,5-dimethylhexyl)-3-[7-(4-methoxyphenyl)-[1,2,4]triazolo[1,5-a]pyrimidin-2-yl]urea;
(S)-1-(5-hydroxy-1,5-dimethylhexyl)-3-{7-[3-(pyridin-3-ylmethoxy)phenyl]-[1,2,4]triazolo[1,5-a]pyrimidin-2-yl}urea;
(S)-1-(5-hydroxy-1,5-dimethylhexyl)-3-(7-thiophen-2-yl[1,2,4]triazolo[1,5a]pyrimidin-2-yl)urea;
(S)-1-[1-(3-methoxyphenyl)ethyl]-3-[7-(4-methoxyphenyl)-[1,2,4]triazolo[1,5-a]pyrimidin-2-yl]urea;
(S-1-[7-(3,4-methylenedioxyphenyl)-[1,2,4]triazolo[1,5-a]pyrimidin-2-yl]-3-[1-(3-methoxyphenyl)ethyl]urea;
(S)-1-[7-(3,4-methylenedioxyphenyl)-[1,2,4]triazolo[1,5-a]pyrimidin-2-yl]-3-[1-(3,4,5-trimethoxyphenyl)ethyl]urea;
(S)-1-(7-thiophen-2-yl[1,2,4]triazolo[1,5-a]pyrimidin-2-yl)-3-[1-(3,4,5-trimethoxyphenyl)ethyl]urea;
(S)-1-[1-(3,4-methylenedioxyphenyl)ethyl]-3-{7-[3-(pyridin-3-ylmethoxy)phenyl]-[1,2,4]triazolo[1,5-a]pyrimidin-2-yl}urea;
or a pharmaceutically acceptable salt thereof.

* * * * *